(12) United States Patent
Muramoto et al.

(10) Patent No.: US 10,745,691 B2
(45) Date of Patent: Aug. 18, 2020

(54) POLYPEPTIDE FOR GENOME SHUFFLING IN PLANTS, AND USE THEREFOR

(71) Applicant: KABUSHIKI KAISHA TOYOTA CHUO KENKYUSHO, Nagakute-shi, Aichi (JP)

(72) Inventors: Nobuhiko Muramoto, Nagakute (JP); Tomoko Tanaka, Nagakute (JP); Hidenori Tanaka, Nagakute (JP); Ritsuko Yogo, Nagakute (JP); Hiroki Sugimoto, Nagakute (JP)

(73) Assignee: KABUSHIKI KAISHA TOYOTA CHUO KENKYUSHO, Nagakute-shi (JP)

( * ) Notice: Subject to any disclaimer, the term of this patent is extended or adjusted under 35 U.S.C. 154(b) by 117 days.

(21) Appl. No.: 15/837,313

(22) Filed: Dec. 11, 2017

(65) Prior Publication Data
US 2018/0305708 A1 Oct. 25, 2018

(30) Foreign Application Priority Data
Dec. 12, 2016 (JP) ................................ 2016-240714

(51) Int. Cl.
| | |
|---|---|
| *C12N 15/10* | (2006.01) |
| *C12N 15/82* | (2006.01) |
| *A01H 5/10* | (2018.01) |
| *A01H 5/02* | (2018.01) |
| *C07K 14/415* | (2006.01) |

(52) U.S. Cl.
CPC ........... *C12N 15/1027* (2013.01); *A01H 5/02* (2013.01); *A01H 5/10* (2013.01); *C07K 14/415* (2013.01); *C12N 15/8216* (2013.01); *C12N 15/8241* (2013.01); *C07K 2319/00* (2013.01)

(58) Field of Classification Search
None
See application file for complete search history.

(56) References Cited

U.S. PATENT DOCUMENTS
2008/0166809 A1 7/2008 Ohta et al.
2011/0277189 A1 11/2011 Kondo et al.

FOREIGN PATENT DOCUMENTS
| | | |
|---|---|---|
| JP | 2004-261122 A | 9/2004 |
| JP | 2006-141322 A | 6/2006 |
| JP | 4158920 B2 | 10/2008 |
| JP | 2011-160798 A | 8/2011 |
| JP | 2012-044883 A | 3/2012 |

OTHER PUBLICATIONS

Wigge (2011) Curr Biol 21:R373-78.*
Xoconostle-Cazares et al. (1999) Sci 283:94-98.*
Deom et al. (1992) Cell 69:221-24.*
Michel et al. (1997) EMBO J 16(2):430-38.*
Podevin et al. (2013) Trends Biotech 31(6):375-83.*
Turck et al. (2008) Annu Rev Plant Biol 59:573-94.*
Rhoads et al. (1998) J Biol Chem 273(46):30750-56.*
Hill & Preiss (1998) Biochem Biophys Res Commun 244(2):573-77.*
Whisstock & Lesk (2003) Q Rev Biophys. 36(3):307-40.*
Guo et al. (2004) Proc Natl Acad Sci USA 101:9205-10.*
Notaguchi et al; "Long-Distance, Graft-Transmissible Action of *Arabidopsis* Flowering Locus T Protein to Promote Flowering;" Plant Cell Physiol.; 2008; vol. 49; No. 11; pp. 1645-1658.
Corbesier et al; "FT Protein Movement Contributes to Long-Distance Signaling in Floral Induction of *Arabidopsis*;" Science; 2007; vol. 316; pp. 1030-1033.
Tamaki et al; "Hd3a Protein Is a Mobile Flowering Signal in Rice;" Science; 2007; vol. 316; pp. 1033-1036.
Mar. 12, 2019 Office Action issued in Japanese Patent Application No. 2016-240714.
Svitashev, Sergei et al., "Genome Editing in Maize Directed by Crispr-CAS9 Ribonucleoprotein Complexes", Nature Communications, 13274, vol. 7, (2016).
Woo, Je Wook et al., "DNA-Free Genome Editing in Plants With Preassembled Crispr-CAS9 Ribonucleoproteins", Nature Biotechnology, 3389, vol. 10, (2015).

* cited by examiner

*Primary Examiner* — Russell T Boggs
(74) *Attorney, Agent, or Firm* — Oliff PLC

(57) ABSTRACT

Provided is a genome shuffling technology suited to creating a useful next-generation plant body.

Genome shuffling is performed using a polypeptide comprising a first polypeptide region for double-stranded DNA breakage activity and a second polypeptide region for inter-tissue migration activity.

12 Claims, 15 Drawing Sheets

Specification includes a Sequence Listing.

FIG. 1A

01 Oryza brachyantha_XP_006655811.1
02 Oryza longistaminata_BAH30239.1
03 Oryza nivara_AFK31118.1
04 Oryza officinalis_AFK31122.1
05 Oryza glumipatula_BAH56285.1
06 Oryza rufipogon_BAG72293.1
07 Oryza sativa Japonica Group_BAO02906.1
08 Oryza sativa Indica Group_BAO03047.1
09 Oryza sativa_BAO03005.1
10 Setaria italica_XP_004964799.1
11 Brachypodium distachyon_XP_003564300.1
12 Festuca pratensis_CBN73209.1
13 Lolium temulentum_CBN73219.1
14 Lolium perenne_CBN73215.1
15 Hordeum vulgare subsp. vulgare_AAZ38709.1
16 Hordeum vulgare_ADW82821.1
17 Phalaenopsis hybrid cultivar_AGE45850.1
18 Aegilops tauschii_ABI34864.1
19 Phalaenopsis japonica_AHB86977.1
20 Triticum aestivum_AAW23034.1
21 Sorghum bicolor_XP_002436509.1
22 Zea mays_NP_001106252.1
23 Gypsophila paniculata_BAK23998.1
24 Beta vulgaris subsp. vulgaris_XP_010673871.1
25 Cymbidium faberi_ADW76861.1
26 Cymbidium goeringii_ADI58462.1
27 Persea americana var. americana_AIG92770.1
28 Eucalyptus grandis_XP_010038569.1
29 Nelumbo nucifera_XP_010268289.1
30 Sesamum indicum_XP_011084685.1
31 Litchi chinensis_AEU08964.1
32 Vitis labrusca x Vitis vinifera_ABN46891.1
33 Vitis vinifera_ABF56526.1
34 Paeonia x lemoinei_AKS43551.1
35 Jatropha curcas_NP_001295681.1
36 Cucurbita moschata_ABR20499.1
37 Cucumis sativus_NP_001292686.1
38 Populus nigra_BAD02371.1
39 Populus trichocarpa_XP_002311264.1
40 Shorea beccariana_BAN89456.1
41 Solanum tuberosum_XP_006352146.1
42 Nicotiana tomentosiformis_XP_009599213.1
43 Nicotiana sylvestris_XP_009776089.1
44 Camellia sinensis_AGD93126.1
45 Populus tomentosa_AFU08240.1
46 Prunus persica_XP_007206002.1
47 Prunus mume_BAH82787.1
48 Prunus pseudocerasus_AIW39809.1
49 Eriobotrya deflexa_AMB72867.1
50 Pyrus x bretschneideri_NP_001289254.1
51 Malus domestica_NP_001280810.1
52 Carica papaya_ACX85427.1
53 Betula platyphylla_AFR31531.1
54 Betula luminifera_AFK91525.1
55 Gossypium hirsutum_XP_016714962.1
56 Gossypium raimondii_XP_012476940.1
57 Fagus crenata_BAP28173.1
58 Theobroma cacao_XP_007028083.1
59 Ficus carica_BAI60052.1
60 Ziziphus jujuba_XP_015873598.1
61 Tarenaya hassleriana_XP_010551361.1
62 Arabis alpina_KFK41391.1
63 Arabidopsis thaliana_NP_176726.1
64 Arabidopsis lyrata subsp. petraea_AKX67445.1
65 Arabidopsis halleri subsp. gemmifera_BAJ08316.1
66 Arabidopsis lyrata subsp. lyrata_XP_002886920.1
67 Capsella rubella_XP_006300555.1
68 Camelina sativa_XP_010511444.1
69 Boechera stricta_AIU56794.1
70 Cardamine hirsuta_AKC05615.1
71 Brassica oleracea_ACH86033.1
72 Brassica oleracea var. oleracea_XP_013590834.1
73 Sinapis alba_ACM69283.1
74 Brassica carinata_AFS51665.1
75 Brassica napus_XP_013699257.1
76 Brassica juncea_AFS51654.1
77 Brassica rapa_XP_009127403.1
78 Eutrema japonicum_ADV18466.1
79 Eutrema salsugineum_XP_006391553.1

| # | | | | |
|---|---|---|---|---|
| 01 | 151 | ELYNLGSPIAAVYFNCQREAGSGGRR | IYN-- | 179 |
| 02 | 150 | ELYNIGSPVATVYFNCQREAGSGGRR | VYP-- | 178 |
| 03 | 151 | ELYNLGSPVAAVYFNCQREAGSGGRR | VYN-- | 179 |
| 04 | 151 | ELYNLGSPVAAVYFNCQREAGSGGRR | VYN-- | 179 |
| 05 | 151 | ELYNLGSPVAAVYFNCQREAGSGGRR | IYP-- | 179 |
| 06 | 151 | ELYNLGSPVAAVYFNCQREAGSGGRR | IYP-- | 179 |
| 07 | 151 | ELYNLGSPVAAAYFNCQREAGSGGRR | VYP-- | 179 |
| 08 | 151 | ELYNLGSPVAAVYFNCQREAGSGGRR | VYP-- | 179 |
| 09 | 151 | ELYNLGSPVAAVYFNCQREAGSGGRR | VYP-- | 179 |
| 10 | 150 | ELYNLGPPVAAVYFNCQREAGSGGRR | MYP-- | 178 |
| 11 | 149 | ELYNLGPPAVAAVYFNCQREAAGSGGRR | MYP-- | 177 |
| 12 | 149 | ELYNLGPPVAAVYFNCQREAGSGGRR | MYN-- | 177 |
| 13 | 149 | ELYNLGPPVAAVYFNCQREAGSGGRR | MYN-- | 177 |
| 14 | 149 | ELYNLGPPVAAVYFNCQREAGSGGRR | MYN-- | 177 |
| 15 | 149 | ELYNLGQPVAAVYFNCQREAGSGGRR | MYN-- | 174 |
| 16 | 149 | ELYNLGQPVAAVYFNCQREAGSGGRR | MY--- | 177 |
| 17 | 149 | ELYNLGPPVAAVYFNCQREAGSGGRR | MYN-- | 177 |
| 18 | 149 | ELYNLGPPVAAVYFNCQREAGSGGRR | MYN-- | 177 |
| 19 | 149 | ELYNLGPPVAAVYFNCQREAGSGGRR | MYN-- | 179 |
| 20 | 149 | ELYNLGPPVAAVYFNCQREAGSGGRR | MYS-- | 177 |
| 21 | 151 | ELYNLGPPVAAVYFNCQREGGSGGRR | LRD-- | 177 |
| 22 | 149 | ELYNLGPPVAAVYNCQREGGSGGRR | L---- | 175 |
| 23 | 149 | ELYNLGLPVAAVYFNCQREAGSGGRR | MQD-- | 176 |
| 24 | 149 | ELYNLGLPVAAVYFNCQREAGSGGRR | MQD-- | 176 |
| 25 | 148 | ELYNLGSPVAALYCNCQREAGSGGRR | R---- | 174 |
| 26 | 148 | ELYNLGLPVAALYFNCQREAGSGGRR | R---- | 175 |
| 27 | 148 | ELYNLGLPVAAVYFNCQRESGSGGRR | R---- | 174 |
| 28 | 149 | ELYNLGLPVAAVYNCQRESGSGGRR | R---- | 175 |
| 29 | 148 | ELYNLGSPVAAVYFNCQRESGTGGRR | R---- | 174 |
| 30 | 148 | ELYNLGSPVAAVYFNCQRESGSGGRR | R---- | 174 |
| 31 | 148 | ELYNLGLPVAAVYFNCQREGGSGGRR | R---- | 174 |
| 32 | 148 | ELYNLGLPVAAVYFNCQREGGSGGRR | S---- | 174 |
| 33 | 148 | ELYNLGLPVAAVYFNCQREGGSGGRR | S---- | 174 |
| 34 | 148 | ELYNLGLPVAAVYFNCQREAGSGGRR | R---- | 173 |
| 35 | 150 | ELYNLGLPVAAVYFNCQRERGSGGRR | R---- | 176 |
| 36 | 148 | ELYNLGLPVAAVYFNCQRESGSGGRR | RSQDF | 179 |
| 37 | 148 | ELYNLGLPVAAVYFNCQRESGTGGRR | RDDDY | 179 |
| 38 | 148 | ELYNLGLPVAAVYFNCQRESGSGGRR | RVQDI | 174 |
| 39 | 148 | ELYNLGSPVAAVYFNCQRESGSGGRR | R---- | 174 |
| 40 | 149 | EVYNLGSPVAAVYFNCQRETGTGGRR | G---- | 175 |

Results of a Homology Analysis for Amino Acid Sequence of Rice Florigen Protein Hd3a (Accession No. BAO03005.1)

| | Score | Expect | Identities | Positives | Gaps |
|---|---|---|---|---|---|
| Oryza brachyantha_XP_006655811.1 | 340 bits(871) | 5.00E-118 | 159/178(89%) | 169/178(94%) | 0/178(0%) |
| Oryza longistaminata_BAH30239.1 | 334 bits(856) | 1.00E-115 | 159/179(89%) | 169/179(94%) | 1/179(0%) |
| Oryza officinalis_AFK31122.1 | 367 bits(943) | 6.00E-129 | 177/178(99%) | 177/178(99%) | 0/178(0%) |
| Oryza nivara_AFK31118.1 | 369 bits(947) | 2.00E-129 | 177/178(99%) | 178/178(100%) | 0/178(0%) |
| Oryza glumipatula_BAH56285.1 | 369 bits(947) | 1.00E-129 | 177/179(99%) | 178/179(99%) | 0/179(0%) |
| Oryza rufipogon_BAG72293.1 | 372 bits(954) | 1.00E-130 | 177/179(99%) | 179/179(100%) | 0/179(0%) |
| Oryza sativa Japonica Group_BAO02906.1 | 371 bits(953) | 2.00E-130 | 178/179(99%) | 178/179(99%) | 0/179(0%) |
| Setaria italica_XP_004964799.1 | 335 bits(860) | 2.00E-116 | 157/179(88%) | 172/179(96%) | 1/179(0%) |
| Brachypodium distachyon_XP_003564300.1 | 342 bits(878) | 4.00E-119 | 160/176(91%) | 171/176(97%) | 0/176(0%) |
| Lolium temulentum_CBN73219.1 | 337 bits(865) | 4.00E-117 | 158/175(90%) | 168/175(96%) | 0/175(0%) |
| Festuca pratensis_CBN73209.1 | 336 bits(862) | 1.00E-116 | 158/175(90%) | 167/175(95%) | 0/175(0%) |
| Lolium perenne_CBN73215.1 | 339 bits(869) | 1.00E-117 | 159/175(91%) | 168/175(96%) | 0/175(0%) |
| Hordeum vulgare subsp. vulgare_AAZ38709.1 | 337 bits(865) | 4.00E-117 | 158/175(90%) | 167/175(95%) | 0/175(0%) |
| Hordeum vulgare_ADW82821.1 | 334 bits(857) | 7.00E-116 | 157/173(91%) | 165/173(95%) | 0/173(0%) |
| Phalaenopsis japonica_AHB86977.1 | 336 bits(861) | 2.00E-116 | 158/175(90%) | 167/175(95%) | 0/175(0%) |
| Aegilops tauschii_ABI34864.1 | 338 bits(866) | 3.00E-117 | 158/175(90%) | 168/175(96%) | 0/175(0%) |
| Phalaenopsis hybrid cultivar_AGE45850.1 | 336 bits(861) | 1.00E-116 | 158/175(90%) | 167/175(95%) | 0/175(0%) |
| Triticum aestivum_AAW23034.1 | 338 bits(866) | 2.00E-117 | 159/175(91%) | 168/175(96%) | 0/175(0%) |
| Sorghum bicolor_XP_002436509.1 | 335 bits(860) | 2.00E-116 | 158/178(89%) | 170/178(95%) | 0/178(0%) |
| Zea mays_NP_001106252.1 | 335 bits(860) | 3.00E-116 | 157/175(90%) | 168/175(96%) | 0/175(0%) |

FIG. 2B

Results of a Homology Analysis for Amino Acid Sequence of Arabidopsis Thaliana Florigen Protein FT (Accession No. NP_176726.1)

| | Score | Expect | Identities | Positives | Gaps |
|---|---|---|---|---|---|
| Gypsophila paniculata BAK23998.1 | 291 bits(746) | 4.00E-99 | 133/170(78%) | 153/170(90%) | 0/170(0%) |
| Beta vulgaris subsp. vulgaris XP_010673871.1 | 291 bits(746) | 5.00E-99 | 131/170(77%) | 152/170(89%) | 0/170(0%) |
| Cymbidium faberi ADW76861.1 | 288 bits(738) | 9.00E-98 | 131/170(77%) | 150/170(88%) | 0/170(0%) |
| Cymbidium goeringii ADI58462.1 | 289 bits(739) | 5.00E-98 | 131/170(77%) | 151/170(88%) | 0/170(0%) |
| Persea americana var. americana AIG92770.1 | 288 bits(737) | 9.00E-98 | 137/169(81%) | 149/169(88%) | 0/169(0%) |
| Eucalyptus grandis XP_010038569.1 | 291 bits(746) | 5.00E-99 | 132/174(76%) | 155/174(89%) | 0/174(0%) |
| Nelumbo nucifera XP_010268289.1 | 292 bits(747) | 3.00E-99 | 135/169(80%) | 153/169(90%) | 0/169(0%) |
| Sesamum indicum XP_011084685.1 | 290 bits(741) | 3.00E-98 | 133/169(79%) | 150/169(88%) | 0/169(0%) |
| Litchi chinensis AEU08964.1 | 288 bits(738) | 8.00E-98 | 129/169(76%) | 151/169(89%) | 0/169(0%) |
| Vitis labrusca x Vitis vinifera ABN46891.1 | 291 bits(745) | 7.00E-99 | 136/169(80%) | 152/169(89%) | 0/169(0%) |
| Vitis vinifera ABF56526.1 | 293 bits(749) | 1.00E-99 | 137/169(81%) | 152/169(89%) | 0/169(0%) |
| Paeonia x lemoinei AKS43551.1 | 288 bits(738) | 8.00E-98 | 134/169(79%) | 151/169(89%) | 0/169(0%) |
| Jatropha curcas NP_001295681.1 | 289 bits(739) | 6.00E-98 | 134/171(78%) | 152/171(88%) | 0/171(0%) |
| Cucurbita moschata ABR20499.1 | 288 bits(737) | 1.00E-97 | 130/169(77%) | 152/169(89%) | 0/169(0%) |
| Cucumis sativus NP_001292686.1 | 290 bits(743) | 1.00E-98 | 133/169(79%) | 153/169(90%) | 0/169(0%) |
| Populus nigra BAD02371.1 | 293 bits(751) | 7.00E-100 | 135/169(80%) | 151/169(89%) | 0/169(0%) |
| Populus trichocarpa XP_002311264.1 | 292 bits(748) | 2.00E-99 | 134/169(79%) | 151/169(89%) | 0/169(0%) |
| Shorea beccariana BAN89456.1 | 288 bits(737) | 1.00E-97 | 131/168(78%) | 152/168(90%) | 0/168(0%) |
| Solanum tuberosum XP_006352146.1 | 287 bits(734) | 2.00E-97 | 133/169(79%) | 152/169(89%) | 0/169(0%) |
| Nicotiana sylvestris XP_009776089.1 | 290 bits(742) | 2.00E-98 | 134/169(79%) | 152/169(89%) | 0/169(0%) |
| Nicotiana tomentosiformis XP_009599213.1 | 288 bits(738) | 8.00E-98 | 134/169(79%) | 151/169(89%) | 0/169(0%) |
| Camellia sinensis AGD93126.1 | 288 bits(737) | 1.00E-97 | 132/169(78%) | 152/169(89%) | 0/169(0%) |
| Populus tomentosa AFU08240.1 | 289 bits(739) | 5.00E-98 | 133/169(79%) | 151/169(89%) | 0/169(0%) |
| Eriobotrya deflexa AMB72867.1 | 289 bits(739) | 6.00E-98 | 132/169(78%) | 153/169(90%) | 0/169(0%) |
| Pyrus x bretschneideri NP_001289254.1 | 290 bits(741) | 2.00E-98 | 132/169(78%) | 152/169(89%) | 0/169(0%) |
| Malus domestica NP_001280810.1 | 290 bits(742) | 2.00E-98 | 132/169(78%) | 153/169(90%) | 0/169(0%) |

FIG. 2C

Results of a Homology Analysis for Amino Acid Sequence of Arabidopsis Thaliana Florigen Protein FT (Accession No. NP_176726.1)

| | Score | Expect | Identities | Positives | Gaps |
|---|---|---|---|---|---|
| Prunus mume_BAH82787.1 | 289 bits(740) | 3.00E-98 | 132/169(78%) | 152/169(89%) | 0/169(0%) |
| Prunus persica_XP_007206002.1 | 287 bits(734) | 2.00E-97 | 130/169(77%) | 151/169(89%) | 0/169(0%) |
| Carica papaya_ACX85427.1 | 291 bits(744) | 9.00E-99 | 134/169(79%) | 153/169(90%) | 0/169(0%) |
| Betula platyphylla_AFR31531.1 | 288 bits(737) | 1.00E-97 | 133/169(79%) | 152/169(89%) | 0/169(0%) |
| Betula luminifera_AFK91525.1 | 291 bits(744) | 1.00E-98 | 133/169(79%) | 153/169(90%) | 0/169(0%) |
| Gossypium hirsutum_XP_016714962.1 | 295 bits(754) | 3.00E-100 | 134/169(79%) | 155/169(91%) | 0/169(0%) |
| Gossypium raimondii_XP_012476940.1 | 295 bits(756) | 1.00E-100 | 134/169(79%) | 156/169(92%) | 0/169(0%) |
| Fagus crenata_BAP28173.1 | 292 bits(747) | 3.00E-99 | 134/169(79%) | 152/169(89%) | 0/169(0%) |
| Theobroma cacao_XP_007028083.1 | 291 bits(745) | 6.00E-99 | 133/169(79%) | 154/169(91%) | 0/169(0%) |
| Ficus carica_BAI60052.1 | 291 bits(746) | 4.00E-99 | 133/169(79%) | 153/169(90%) | 0/169(0%) |
| Ziziphus jujuba_XP_015873598.1 | 291 bits(746) | 4.00E-99 | 133/169(79%) | 154/169(91%) | 0/169(0%) |
| Tarenaya hassleriana_XP_010551361.1 | 307 bits(786) | 5.00E-105 | 144/170(85%) | 157/170(92%) | 1/170(0%) |
| Arabis alpina_KFK41391.1 | 312 bits(799) | 4.00E-107 | 159/174(91%) | 166/174(95%) | 0/174(0%) |
| Arabidopsis lyrata subsp. petraea_AKX67445.1 | 352 bits(903) | 5.00E-123 | 168/175(96%) | 173/175(98%) | 0/175(0%) |
| Arabidopsis halleri subsp. gemmifera_BAJ08316.1 | 354 bits(908) | 8.00E-124 | 169/175(97%) | 174/175(99%) | 0/175(0%) |
| Arabidopsis lyrata subsp. lyrata_XP_002886920.1 | 353 bits(907) | 1.00E-123 | 169/175(97%) | 174/175(99%) | 0/175(0%) |
| Camelina sativa_XP_010511444.1 | 351 bits(901) | 3.00E-122 | 166/174(95%) | 171/174(98%) | 0/174(0%) |
| Capsella rubella_XP_006300555.1 | 344 bits(883) | 5.00E-120 | 164/174(94%) | 170/174(97%) | 0/174(0%) |
| Boechera stricta_AIU56794.1 | 343 bits(881) | 1.00E-119 | 165/174(95%) | 169/174(97%) | 0/174(0%) |
| Cardamine hirsuta_AKC05615.1 | 346 bits(887) | 2.00E-120 | 164/175(94%) | 172/175(98%) | 0/175(0%) |
| Brassica oleracea_ACH86033.1 | 307 bits(786) | 4.00E-105 | 144/175(82%) | 159/175(90%) | 0/175(0%) |
| Brassica oleracea var. oleracea_XP_013590834.1 | 306 bits(784) | 7.00E-105 | 143/174(82%) | 158/174(90%) | 0/174(0%) |
| Sinapis alba_ACM69283.1 | 304 bits(779) | 4.00E-104 | 141/174(81%) | 159/174(91%) | 0/174(0%) |
| Brassica juncea_AFS51654.1 | 314 bits(804) | 6.00E-108 | 149/174(86%) | 160/174(91%) | 0/174(0%) |
| Brassica napus_XP_013699257.1 | 315 bits(807) | 3.00E-108 | 150/174(86%) | 160/174(91%) | 0/174(0%) |
| Brassica carinata_AFS51665.1 | 316 bits(809) | 1.00E-108 | 151/174(87%) | 160/174(91%) | 0/174(0%) |
| Brassica rapa_XP_009127403.1 | 315 bits(808) | 2.00E-108 | 150/174(86%) | 160/174(91%) | 0/174(0%) |
| Eutrema japonicum_ADV18466.1 | 313 bits(802) | 1.00E-107 | 149/174(86%) | 161/174(92%) | 0/174(0%) |
| Eutrema salsugineum_XP_006391553.1 | 311 bits(798) | 4.00E-107 | 148/171(87%) | 159/171(92%) | 0/171(0%) |

**Phenotypes of *nle* Mutant Strains**

Plant Bodies 21 days after Sowing (A), Cotyledons Thereof (B), 1st Leaves of True Leaves Thereof (C), and 3rd Leaves of True Leaves Thereof (D).
Bar = 10mm (A), 1mm (B-D)

Col-0    *nle-m* Mutant Strain    *nle-r* Mutant Strain

Col-0    *nle-m* Mutant Strain    *nle-r* Mutant Strain

Col-0    *nle-m* Mutant Strain    *nle-r* Mutant Strain

Col-0    *nle-m* Mutant Strain    *nle-r* Mutant Strain

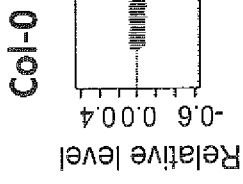
FIG. 5A Col-0
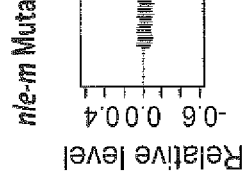
FIG. 5B nle-m Mutant Strain
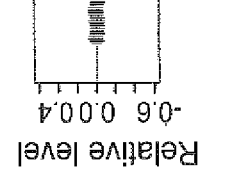
FIG. 5C nle-r Mutant Strain

SEQUENCE LISTING

```
<160> NUMBER OF SEQ ID NOS: 97

<210> SEQ ID NO 1
<211> LENGTH: 175
<212> TYPE: PRT
<213> ORGANISM: Arabidopsis thaliana

<400> SEQUENCE: 1

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110
```

```
Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 2
<211> LENGTH: 528
<212> TYPE: DNA
<213> ORGANISM: Arabidopsis thaliana

<400> SEQUENCE: 2
atgtctataa atataagaga ccctcttata gtaagcagag ttgttggaga cgttcttgat     60
ccgtttaata gatcaatcac tctaaaggtt acttatggcc aaagagaggt gactaatggc    120
ttggatctaa ggccttctca ggttcaaaac aagccaagtt tgagattgg tggagaagac    180 ctcaggaact tctatacttt ggttatggtg gatccagatg ttccaagtcc tagcaaccct    240
cacctccgag aatatctcca ttggttggtg actgatatcc ctgctacaac tggaacaacc    300
tttggcaatg agattgtgtg ttacgaaaat ccaagtccca ctgcaggaat tcatcgtgtc    360
gtgtttatat tgtttcgaca gcttggcagg caaacagtgt atgcaccagg tggcgccag    420 aacttcaaca ctcgcgagtt tgctgagatc tacaatctcg gccttcccgt ggccgcagtt    480
ttctacaatt gtcagaggga gagtggctgc ggaggaagaa gactttag               528

<210> SEQ ID NO 3
<211> LENGTH: 179
<212> TYPE: PRT
<213> ORGANISM: Oryza sativa

<400> SEQUENCE: 3

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175
```

Val Tyr Pro

<210> SEQ ID NO 4
<211> LENGTH: 540
<212> TYPE: DNA
<213> ORGANISM: Oryza sativa

<400> SEQUENCE: 4

| | | | | | |
|---|---|---|---|---|---|
| atggccggaa | gtggcaggga | cagggaccct | cttgtggttg | gtagggttgt | gggtgatgtg | 60 |
| ctggacgcgt | tcgtccggag | caccaacctc | aaggtcacct | atggctccaa | gaccgtgtcc | 120 |
| aatggctgcg | agctcaagcc | gtccatggtc | acccaccagc | ctagggtcga | ggtcggcggc | 180 |
| aatgacatga | ggacattcta | cacccttgtg | atggtagacc | cagatgcacc | aagcccaagt | 240 |
| gaccctaacc | ttagggagta | tctacattgg | ttggtcactg | atattcctgg | tactactgca | 300 |
| gcgtcatttg | gcaagaggt | gatgtgctac | gagagcccaa | ggccaaccat | ggggatccac | 360 |
| cggctggtgt | tcgtgctgtt | ccagcagctg | gggcgtcaga | cagtgtacgc | gcccgggtgg | 420 |
| cgtcagaact | tcaacaccaa | ggacttcgcc | gagctctaca | acctcggctc | gccggtcgcc | 480 |
| gccgtctact | tcaactgcca | gcgcgaggca | ggctccggcg | gcaggagggt | ctaccccag | 540 |

<210> SEQ ID NO 5
<211> LENGTH: 27
<212> TYPE: DNA
<213> ORGANISM: Artificial
<220> FEATURE:
<223> OTHER INFORMATION: Primer

<400> SEQUENCE: 5
actcgagtct ggtggtttca acttggg                                        27

<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6
aggatccgtc gactgttcgt tgcttttcgg gag                                 33

<210> SEQ ID NO 7
<211> LENGTH: 44
<212> TYPE: DNA
<213> ORGANISM: Artificial
<220> FEATURE:
<223> OTHER INFORMATION: Primer

<400> SEQUENCE: 7
agggccccat atggtcgaca tgtctataaa tataagagac cctc                     44

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
aggtaccaag tcttcttcct ccgcagc                                        27

<210> SEQ ID NO 9
<211> LENGTH: 42

<210> SEQ ID NO 9
<211> LENGTH: 42
<212> TYPE: DNA
<213> ORGANISM: Artificial
<220> FEATURE:
<223> OTHER INFORMATION: Primer

<400> SEQUENCE: 9
aggtaccgga ggtggaggtg caatggcccc tacacaagcc ca            42

<210> SEQ ID NO 10
<211> LENGTH: 31
<212> TYPE: DNA
<213> ORGANISM: Artificial
<220> FEATURE:
<223> OTHER INFORMATION: Primer

<400> SEQUENCE: 10
agagctctgt acctcacggg ccggtgaggg c                        31

<210> SEQ ID NO 11
<211> LENGTH: 51
<212> TYPE: DNA
<213> ORGANISM: Artificial
<220> FEATURE:
<223> OTHER INFORMATION: Priemr

<400> SEQUENCE: 11
aattactatt tacaattaca gtcgacatgt ctataaatat aagagaccct c   51

<210> SEQ ID NO 12
<211> LENGTH: 50
<212> TYPE: DNA
<213> ORGANISM: Artificial
<220> FEATURE:
<223> OTHER INFORMATION: Primer

<400> SEQUENCE: 12
agccgggcgg ccgctttact tgtacatgta cctcacgggc cggtgagggc     50

<210> SEQ ID NO 13
<211> LENGTH: 179
<212> TYPE: PRT
<213> ORGANISM: Oryza brachyantha

<400> SEQUENCE: 13

Met Ala Gly Ser Gly Ser Gly Arg Asp Pro Leu Val Val Gly Arg Val
1               5                   10                  15

Val Gly Asp Val Leu Asp Gln Phe Thr Arg Thr Thr Asn Leu Arg Val
            20                  25                  30

Ser Tyr Gly Ala Arg Thr Val Ser Asn Gly Cys Glu Leu Lys Pro Ser
        35                  40                  45

Met Val Thr Gln Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Thr Glu Tyr Leu His Trp Leu Val Thr Asp Ile Pro
                85                  90                  95

Gly Thr Thr Gly Ala Ala Phe Gly Gln Glu Val Met Cys Tyr Glu Ser
            100                 105                 110

Pro Arg Pro Ile Met Gly Ile His Arg Leu Val Phe Val Leu Phe Gln
        115                 120                 125

Gln Leu Arg Arg Gln Thr Val Phe Ala Pro Gly Trp Arg Gln Asn Phe
    130                 135                 140

Asn Thr Arg Asp Phe Ala Glu Leu Tyr Asn Leu Gly Ser Pro Ile Ala
145                 150                 155                 160

Ala Val Tyr Phe Asn Cys Gln Arg Glu Ala Gly Ser Gly Gly Arg Arg
                165                 170                 175

Ile Tyr Asn

<210> SEQ ID NO 14
<211> LENGTH: 178
<212> TYPE: PRT
<213> ORGANISM: Oryza longistaminata

<400> SEQUENCE: 14

Met Ala Gly Ser Gly Arg Asp Asp Pro Leu Val Val Gly Arg Ile Val
1               5                   10                  15

Gly Asp Val Leu Asp Pro Phe Val Arg Ile Thr Asn Leu Ser Val Ser
                20                  25                  30

Tyr Gly Ala Arg Ile Val Ser Asn Gly Cys Glu Leu Lys Pro Ser Met
            35                  40                  45

Val Thr Gln Gln Pro Arg Val Val Gly Gly Asn Asp Met Arg Thr
    50                  55                  60

Phe Tyr Thr Leu Val Met Val Asp Pro Asp Ala Pro Ser Pro Ser Asn
65                  70                  75                  80

Pro Asn Leu Arg Glu Tyr Leu His Trp Leu Val Thr Asp Ile Pro Gly
                85                  90                  95

Thr Thr Gly Thr Thr Phe Gly Gln Glu Val Met Cys Tyr Glu Ser Pro
            100                 105                 110

Arg Pro Thr Met Gly Ile His Arg Leu Val Phe Val Leu Phe Gln Gln
        115                 120                 125

Leu Gly Arg Gln Thr Val Tyr Ala Pro Gly Trp Arg Gln Asn Phe Ser
    130                 135                 140

Thr Arg Asn Phe Ala Glu Leu Tyr Asn Ile Gly Ser Pro Val Ala Thr
145                 150                 155                 160

Val Tyr Phe Asn Cys Gln Arg Glu Ala Gly Ser Gly Gly Arg Arg Val
                165                 170                 175

Tyr Pro

<210> SEQ ID NO 15
<211> LENGTH: 179
<212> TYPE: PRT
<213> ORGANISM: Oryza nivara

<400> SEQUENCE: 15

Met Ala Gly Ser Gly Arg Asp Arg Asp Pro Leu Val Val Gly Arg Val
1               5                   10                  15

Val Gly Asp Val Leu Asp Ala Phe Val Gln Ser Thr Asn Leu Lys Val
                20                  25                  30

Thr Tyr Gly Ser Lys Thr Val Ser Asn Gly Cys Glu Leu Lys Pro Ser
            35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser

```
                100                 105                 110
Pro Arg Pro Thr Met Gly Ile His Arg Leu Val Phe Val Leu Phe Gln
            115                 120                 125

Gln Leu Gly Arg Gln Thr Val Tyr Ala Pro Gly Trp Arg Gln Asn Phe
        130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Asn

<210> SEQ ID NO 16
<211> LENGTH: 179
<212> TYPE: PRT
<213> ORGANISM: Oryza officinalis

<400> SEQUENCE: 16

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Gly Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Asn

<210> SEQ ID NO 17
<211> LENGTH: 179
<212> TYPE: PRT
<213> ORGANISM: Oryza glumipatula

<400> SEQUENCE: 17

Met Ala Arg Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60
```

```
Thr Phe Tyr Thr Leu Val Met Val Asp Pro Asp Ala Pro Ser Pro Ser
 65                  70                  75                  80

Asp Pro Asn Leu Arg Glu Tyr Leu His Trp Leu Val Thr Asp Ile Pro
                 85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Ile Tyr Pro

<210> SEQ ID NO 18
<211> LENGTH: 179
<212> TYPE: PRT
<213> ORGANISM: Oryza rufipogon

<400> SEQUENCE: 18

Met Ala Gly Ser Gly Arg Asp Arg Asp Pro Leu Val Ile Gly Arg Val
  1               5                  10                  15

Val Gly Asp Val Leu Asp Ala Phe Val Arg Ser Thr Asn Leu Lys Val
                 20                  25                  30

Thr Tyr Gly Ser Lys Thr Val Ser Asn Gly Cys Glu Leu Lys Pro Ser
             35                  40                  45

Met Val Thr His Gln Pro Arg Val Glu Val Gly Gly Asn Asp Met Arg
         50                  55                  60

Thr Phe Tyr Thr Leu Val Met Val Asp Pro Asp Ala Pro Ser Pro Ser
 65                  70                  75                  80

Asp Pro Asn Leu Arg Glu Tyr Leu His Trp Leu Val Thr Asp Ile Pro
                 85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Ile Tyr Pro

<210> SEQ ID NO 19
<211> LENGTH: 179
<212> TYPE: PRT
<213> ORGANISM: Oryza sativa Japonica Group

<400> SEQUENCE: 19

Met Ala Gly Ser Gly Arg Asp Arg Asp Pro Leu Val Val Gly Arg Val
  1               5                  10                  15

Val Gly Asp Val Leu Asp Ala Phe Val Arg Ser Thr Asn Leu Lys Val
                 20                  25                  30
```

```
Thr Tyr Gly Ser Lys Thr Val Ser Asn Gly Cys Glu Leu Lys Pro Ser
            35                  40                  45

Met Val Thr His Gln Pro Arg Val Glu Val Gly Gly Asn Asp Met Arg
 50                  55                  60

Thr Phe Tyr Thr Leu Val Met Val Asp Pro Asp Ala Pro Ser Pro Ser
 65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
                100                 105                 110

Pro Arg Pro Thr Met Gly Ile His Arg Leu Val Phe Val Leu Phe Gln
                115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Ala Tyr Phe Asn Cys Gln Arg Glu Ala Gly Ser Gly Gly Arg Arg
                165                 170                 175

Val Tyr Pro

<210> SEQ ID NO 20
<211> LENGTH: 179
<212> TYPE: PRT
<213> ORGANISM: Oryza sativa Indica Group

<400> SEQUENCE: 20

Met Ala Gly Ser Gly Arg Asp Arg Asp Pro Leu Val Val Gly Arg Val
 1               5                  10                  15

Val Gly Asp Val Leu Asp Ala Phe Val Arg Ser Thr Asn Leu Lys Val
                20                  25                  30

Thr Tyr Gly Ser Lys Thr Val Ser Asn Gly Cys Glu Leu Lys Pro Ser
            35                  40                  45

Met Val Thr His Gln Pro Arg Val Glu Val Gly Gly Asn Asp Met Arg
 50                  55                  60

Thr Phe Tyr Thr Leu Val Met Val Asp Pro Asp Ala Pro Ser Pro Ser
 65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
                100                 105                 110

Pro Arg Pro Thr Met Gly Ile His Arg Leu Val Phe Val Leu Phe Gln
                115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro

<210> SEQ ID NO 21
<211> LENGTH: 179
<212> TYPE: PRT
<213> ORGANISM: Oryza sativa
```

<400> SEQUENCE: 21

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro

<210> SEQ ID NO 22
<211> LENGTH: 178
<212> TYPE: PRT
<213> ORGANISM: Setaria italica

<400> SEQUENCE: 22

Met Ala Gly Gly Arg Asp Arg Asp Pro Leu Val Val Gly Arg Val Val
1               5                   10                  15

Gly Asp Val Leu Asp Pro Phe Thr Arg Thr Thr Asn Leu Arg Val Ser
            20                  25                  30

Phe Gly Ala Arg Thr Ile Ala Asn Gly Cys Glu Leu Lys Pro Ser Met
        35                  40                  45

Val Ser His Gln Pro Arg Val Asp Val Gly Gly Pro Asp Met Arg Thr
    50                  55                  60

Phe Tyr Thr Leu Val Met Val Asp Pro Asp Ala Pro Ser Pro Ser Asp
65                  70                  75                  80

Pro Asn Leu Arg Glu Tyr Leu His Trp Leu Val Thr Asp Ile Pro Gly
                85                  90                  95

Ser Thr Gly Ala Ala Phe Gly Gln Glu Val Met Cys Tyr Glu Asn Pro
            100                 105                 110

Arg Pro Thr Met Gly Ile His Arg Phe Val Phe Val Leu Phe Gln Gln
        115                 120                 125

Leu Gly Arg Gln Thr Val Tyr Ala Pro Gly Trp Arg Gln Asn Phe Asn
130                 135                 140

Thr Arg Asp Phe Ala Glu Leu Tyr Asn Leu Gly Pro Pro Val Ala Ala
145                 150                 155                 160

Val Tyr Phe Asn Cys Gln Arg Glu Ala Gly Ser Gly Gly Arg Arg Met
                165                 170                 175

Tyr Pro

<210> SEQ ID NO 23
<211> LENGTH: 177
<212> TYPE: PRT
<213> ORGANISM: Brachypodium distachyon

<400> SEQUENCE: 23

```
Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Ser Phe
            20                  25                  30

Gly Asn Arg Asn Val Ser Asn Gly Cys Glu Leu Lys Pro Ser Met Val
        35                  40                  45

Thr His Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Ser Met Gly Ile His Arg Phe Val Phe Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Gly Arg Arg Met Tyr
                165                 170                 175

Pro
```

<210> SEQ ID NO 24
<211> LENGTH: 177
<212> TYPE: PRT
<213> ORGANISM: Festuca pratensis

<400> SEQUENCE: 24

```
Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
            20                  25                  30

Gly Asn Arg Ala Val Ser Asn Gly Cys Glu Leu Lys Pro Ser Met Val
        35                  40                  45

Thr His Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140
```

Arg Asp Phe Ala Glu Leu Tyr Asn Leu Gly Pro Val Ala Ala Val
145                 150                 155                 160

Tyr Phe Asn Cys Gln Arg Glu Ala Gly Ser Gly Gly Arg Met Tyr
                165                 170                 175

Asn

<210> SEQ ID NO 25
<211> LENGTH: 177
<212> TYPE: PRT
<213> ORGANISM: Lolium temulentum

<400> SEQUENCE: 25

Met Ala Gly Arg Asp Arg Glu Pro Leu Val Val Gly Arg Val Val Gly
1               5                   10                  15

Asp Val Leu Asp Pro Phe Val Arg Thr Thr Asn Leu Arg Val Thr Phe
                20                  25                  30

Gly Asn Arg Ala Val Ser Asn Gly Cys Glu Leu Lys Pro Ser Met Val
            35                  40                  45

Thr His Gln Pro Arg Val Glu Val Gly Gly Asn Glu Met Arg Thr Phe
        50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 26
<211> LENGTH: 177
<212> TYPE: PRT
<213> ORGANISM: Lolium perenne

<400> SEQUENCE: 26

Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
                20                  25                  30

Gly Asn Arg Ala Val Ser Asn Gly Cys Glu Leu Lys Pro Ser Met Val
            35                  40                  45

Thr His Gln Pro Arg Val Glu Val Gly Gly Asn Glu Met Arg Thr Phe
        50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

```
Pro Asn Met Gly Ile His Arg Phe Val Leu Val Leu Phe Gln Gln Leu
            115                 120                 125

Gly Arg Gln Thr Val Tyr Ala Pro Gly Trp Arg Gln Asn Phe Asn Thr
        130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 27
<211> LENGTH: 177
<212> TYPE: PRT
<213> ORGANISM: Hordeum vulgare subsp. Vulgare

<400> SEQUENCE: 27

Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
            20                  25                  30

Gly Asn Arg Ala Val Ser Asn Gly Cys Glu Leu Lys Pro Ser Met Val
        35                  40                  45

Ala Gln Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Thr Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Gln Pro Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 28
<211> LENGTH: 174
<212> TYPE: PRT
<213> ORGANISM: Hordeum vulgare

<400> SEQUENCE: 28

Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
            20                  25                  30

Gly Asn Arg Ala Val Ser Asn Gly Cys Glu Leu Lys Pro Ser Met Val
        35                  40                  45

Ala Gln Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80
```

```
                65                  70                  75                  80
Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Thr Met Gly Ile His Arg Phe Val Leu Val Leu Phe Gln Gln Leu
            115                 120                 125

Gly Arg Gln Thr Val Tyr Ala Pro Gly Trp Arg Gln Asn Phe Asn Thr
        130                 135                 140

Arg Asp Phe Ala Glu Leu Tyr Asn Leu Gly Gln Pro Val Ala Ala Val
145                 150                 155                 160

Tyr Phe Asn Cys Gln Arg Glu Ala Gly Ser Gly Arg Arg
                165                 170
```

<210> SEQ ID NO 29
<211> LENGTH: 177
<212> TYPE: PRT
<213> ORGANISM: Phalaenopsis hybrid cultivar

<400> SEQUENCE: 29

```
Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
            20                  25                  30

Gly Asn Arg Thr Val Ser Asn Gly Cys Glu Leu Lys Pro Ser Met Val
        35                  40                  45

Ala Gln Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Thr Met Gly Ile His Arg Phe Val Leu Val Leu Leu Gln Gln Leu
            115                 120                 125

Gly Arg Gln Thr Val Tyr Ala Pro Gly Trp Arg Gln Asn Phe Asn Thr
        130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Arg Arg Met Tyr
                165                 170                 175

Asn
```

<210> SEQ ID NO 30
<211> LENGTH: 177
<212> TYPE: PRT
<213> ORGANISM: Aegilops tauschii

<400> SEQUENCE: 30

```
Met Ala Gly Arg Asp Arg Asp Pro Leu Val Val Gly Arg Val Val Gly
1               5                   10                  15

Asp Val Leu Asp Pro Phe Ile Arg Thr Thr Asn Leu Arg Val Thr Phe
            20                  25                  30

Gly Asn Arg Thr Val Ser Asn Gly Cys Glu Leu Lys Pro Ser Met Val
        35                  40                  45
```

Ala Gln Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Thr Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 31
<211> LENGTH: 177
<212> TYPE: PRT
<213> ORGANISM: Phalaenopsis japonica

<400> SEQUENCE: 31

Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
                20                  25                  30

Gly Asn Arg Thr Val Ser Asn Gly Cys Glu Leu Lys Pro Ser Met Val
            35                  40                  45

Ala Gln Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Pro Phe Gly Gln Glu Val Met Cys Tyr Glu Ser Pro Arg
            100                 105                 110

Pro Thr Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 32
<211> LENGTH: 177
<212> TYPE: PRT
<213> ORGANISM: Triticum aestivum

<400> SEQUENCE: 32

Met Ala Gly Arg Asp Arg Asp Pro Leu Val Val Gly Arg Val Val Gly

```
1               5                   10                  15
Asp Val Leu Asp Pro Phe Val Arg Thr Thr Asn Leu Arg Val Thr Phe
                20                  25                  30
Gly Asn Arg Thr Val Ser Asn Gly Cys Glu Leu Lys Pro Ser Met Val
            35                  40                  45
Ala Gln Gln Pro Arg Val Glu Val Gly Gly Asn Glu Met Arg Thr Phe
        50                  55                  60
Tyr Thr Leu Val Met Val Asp Pro Asp Ala Pro Ser Pro Ser Asp Pro
65                  70                  75                  80
Asn Leu Arg Glu Tyr Leu His Trp Leu Val Thr Asp Ile Pro Gly Thr
                85                  90                  95
Thr Gly Ala Ser Phe Gly Gln Glu Val Met Cys Tyr Glu Ser Pro Arg
                100                 105                 110
Pro Thr Met Gly Ile His Arg Phe Val Leu Val Leu Phe Gln Gln Leu
                115                 120                 125
Gly Arg Gln Thr Val Tyr Ala Pro Gly Trp Arg Gln Asn Phe Asn Thr
            130                 135                 140
Arg Asp Phe Ala Glu Leu Tyr Asn Leu Gly Pro Pro Val Ala Ala Val
145                 150                 155                 160
Tyr Phe Asn Cys Gln Arg Glu Ala Gly Ser Gly Gly Arg Arg Met Tyr
                165                 170                 175
Asn
```

<210> SEQ ID NO 33
<211> LENGTH: 179
<212> TYPE: PRT
<213> ORGANISM: Sorghum bicolor

<400> SEQUENCE: 33

```
Met Ala Gly Ser Gly Arg Glu Arg Glu Thr Leu Val Val Gly Arg Val
1               5                   10                  15
Val Gly Asp Val Leu Asp Pro Phe Val Arg Thr Thr Asn Leu Arg Val
                20                  25                  30
Ser Tyr Gly Thr Arg Thr Val Ser Asn Gly Cys Glu Leu Lys Pro Ser
            35                  40                  45
Met Val Val Asn Gln Pro Arg Val Glu Val Gly Gly Pro Asp Met Arg
        50                  55                  60
Thr Phe Tyr Thr Leu Val Met Val Asp Pro Asp Ala Pro Ser Pro Ser
65                  70                  75                  80
Asp Pro Asn Leu Arg Glu Tyr Leu His Trp Leu Val Thr Asp Ile Pro
                85                  90                  95
Gly Thr Thr Gly Ala Ala Phe Gly Gln Glu Val Ile Cys Tyr Glu Ser
                100                 105                 110
Pro Arg Pro Thr Met Gly Ile His Arg Phe Val Leu Val Leu Phe Gln
                115                 120                 125
Gln Leu Gly Arg Gln Thr Val Tyr Ala Pro Gly Trp Arg Gln Asn Phe
            130                 135                 140
Asn Thr Arg Asp Phe Ala Glu Leu Tyr Asn Leu Gly Pro Pro Val Ala
145                 150                 155                 160
Ala Val Tyr Phe Asn Cys Gln Arg Glu Ala Gly Ser Gly Gly Arg Arg
                165                 170                 175
Met Tyr Ser
```

<210> SEQ ID NO 34

<211> LENGTH: 177
<212> TYPE: PRT
<213> ORGANISM: Zea mays

<400> SEQUENCE: 34

Met Ala Gly Arg Asp Arg Glu Pro Leu Val Val Gly Arg Val Val Gly
1               5                   10                  15

Asp Val Leu Asp Pro Phe Val Arg Thr Thr Asn Leu Arg Val Ser Tyr
            20                  25                  30

Gly Ala Arg Thr Val Ser Asn Gly Cys Glu Leu Lys Pro Ser Met Val
        35                  40                  45

Val His Gln Pro Arg Val Glu Val Gly Gly Pro Asp Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ala Phe Gly Gln Glu Val Ile Cys Tyr Glu Ser Pro Arg
            100                 105                 110

Pro Thr Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Val Ala Ala Val
145                 150                 155                 160

Tyr Phe Asn Cys Gln Arg Glu Ala Gly Ser Gly Gly Arg Arg Met Tyr
                165                 170                 175

Ser

<210> SEQ ID NO 35
<211> LENGTH: 177
<212> TYPE: PRT
<213> ORGANISM: Gypsophila paniculata

<400> SEQUENCE: 35

Met Pro Arg Val Pro Arg Asp Pro Leu Val Val Gly Arg Val Ile Gly
1               5                   10                  15

Asp Val Leu Asp Pro Phe Asn Arg Ser Val Thr Leu Arg Val Thr Tyr
            20                  25                  30

Asn Gly Arg Asp Val Asn Asn Gly Cys Glu Phe Arg Pro Ser Gln Leu
        35                  40                  45

Val Asn His Pro Arg Val Glu Ile Gly Gly Asp Asp Leu Arg Ser Phe
    50                  55                  60

Tyr Thr Leu Val Met Ala Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Thr Ser Phe Gly Gln Glu Val Val Cys Tyr Glu Ser Pro Arg
            100                 105                 110

Pro Ser Val Gly Ile His Arg Phe Ile Phe Val Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Leu Pro Val Ala Ala Val
145                 150                 155                 160

Tyr Tyr Asn Cys Gln Arg Glu Gly Gly Ser Gly Gly Arg Arg Leu Arg
                165                 170                 175

Asp

<210> SEQ ID NO 36
<211> LENGTH: 175
<212> TYPE: PRT
<213> ORGANISM: Beta vulgaris subsp. Vulgaris

<400> SEQUENCE: 36

Met Pro Arg Ala Pro Arg Asp Pro Leu Val Val Gly Arg Val Ile Gly
1               5                   10                  15

Asp Val Leu Asp Pro Phe Ser Arg Thr Val Asn Leu Arg Val Ser Tyr
                20                  25                  30

Ser Asn Arg Asp Val Asn Asn Gly Cys Glu Leu Arg Pro Ser Gln Val
            35                  40                  45

Val Asn Gln Pro Arg Val Glu Val Gly Gly Asp Asp Leu Arg Thr Phe
        50                  55                  60

Tyr Thr Leu Val Met Val Asp Pro Asp Ala Pro Ser Pro Ser Asn Pro
65                  70                  75                  80

His Leu Arg Glu Tyr Leu His Trp Leu Val Thr Asp Ile Pro Gly Thr
                85                  90                  95

Thr Gly Ala Ser Phe Gly Gln Glu Val Val Cys Tyr Glu Asn Pro Arg
            100                 105                 110

Pro Ser Val Gly Ile His Arg Phe Ile Leu Val Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Leu Pro Val Ala Ala Val
145                 150                 155                 160

Tyr Phe Asn Cys Gln Arg Glu Gly Gly Ser Gly Gly Arg Arg Leu
                165                 170                 175

<210> SEQ ID NO 37
<211> LENGTH: 176
<212> TYPE: PRT
<213> ORGANISM: Cymbidium faberi

<400> SEQUENCE: 37

Met Asn Arg Glu Arg Asp Ser Leu Ile Val Gly Arg Val Ile Gly Asp
1               5                   10                  15

Val Leu Asp Pro Phe Thr Arg Arg Val Ala Leu Arg Val Thr Tyr Ser
                20                  25                  30

Ser Arg Asp Val Thr Asn Gly Leu Glu Leu Lys Pro Ser Ala Val Val
            35                  40                  45

Glu Gln Pro Arg Val Glu Val Gly Gly Asn Asp Leu Arg Thr Phe Tyr
        50                  55                  60

Thr Leu Val Met Val Asp Pro Asp Ala Pro Ser Pro Ser Asp Pro His
65                  70                  75                  80

Leu Arg Glu Tyr Leu His Trp Leu Val Thr Asp Ile Pro Ala Thr Thr
                85                  90                  95

Gly Ala Thr Phe Gly Ser Glu Ile Val Cys Tyr Glu Ser Pro Arg Pro
            100                 105                 110

Ser Leu Gly Ile His Arg Phe Val Phe Val Leu Phe His Gln Leu Gly
        115                 120                 125

Arg Gln Thr Val Tyr Ala Pro Gly Trp Arg Gln Asn Phe Asn Thr Arg

```
            130                 135                 140
Asp Phe Ala Glu Leu Tyr Asn Leu Gly Ser Pro Val Ala Ala Val Tyr
145                 150                 155                 160

Phe Asn Cys Gln Arg Glu Ala Gly Ser Gly Gly Arg Arg Met Gln Asp
                165                 170                 175
```

<210> SEQ ID NO 38
<211> LENGTH: 176
<212> TYPE: PRT
<213> ORGANISM: Cymbidium goeringii

<400> SEQUENCE: 38

```
Met Asn Arg Glu Arg Asp Ser Leu Ile Val Gly Arg Val Ile Gly Asp
1               5                   10                  15

Val Leu Asp Pro Phe Thr Arg Val Ser Leu Arg Val Thr Tyr Ser
                20                  25                  30

Ser Arg Asp Val Thr Asn Gly Leu Glu Leu Lys Pro Ser Ala Val Val
                35                  40                  45

Glu Gln Pro Arg Val Glu Val Gly Gly Asn Asp Leu Arg Thr Phe Tyr
            50                  55                  60

Thr Leu Val Met Val Asp Pro Asp Ala Pro Ser Pro Ser Asp Pro His
65                  70                  75                  80

Leu Arg Glu Tyr Leu His Trp Leu Val Thr Asp Ile Pro Ala Thr Thr
                85                  90                  95

Gly Ala Thr Phe Gly Ser Glu Ile Val Cys Tyr Glu Ser Pro Arg Pro
                100                 105                 110

Ser Leu Gly Ile His Arg Phe Val Phe Val Leu Phe His Gln Leu Gly
                115                 120                 125

Arg Gln Thr Val Tyr Ala Pro Gly Trp Arg Gln Asn Phe Asn Thr Arg
            130                 135                 140

Asp Phe Ala Glu Leu Tyr Asn Leu Gly Ser Pro Val Ala Ala Val Tyr
145                 150                 155                 160

Phe Asn Cys Gln Arg Glu Ala Gly Ser Gly Gly Arg Arg Met Gln Asp
                165                 170                 175
```

<210> SEQ ID NO 39
<211> LENGTH: 174
<212> TYPE: PRT
<213> ORGANISM: Persea americana var. americana

<400> SEQUENCE: 39

```
Met Ala Arg Glu Arg Asp Pro Leu Ile Val Gly Arg Val Ile Gly Asp
1               5                   10                  15

Val Leu Asp Pro Phe Asn Arg Ser Ile Pro Leu Arg Val Thr Phe Asn
                20                  25                  30

Asn Arg Glu Val Thr Asn Gly Cys Asp Leu Arg His Ser His Val Ala
            35                  40                  45

Asn Gln Pro Arg Val Glu Ile Gly Gly Asn Asp Leu Arg Thr Phe Tyr
            50                  55                  60

Thr Leu Val Met Val Asp Pro Asp Ala Pro Ser Pro Ser Asp Pro Thr
65                  70                  75                  80

Leu Arg Glu Tyr Leu His Trp Leu Val Thr Asp Ile Pro Ala Thr Thr
                85                  90                  95

Glu Ala Ser Phe Gly Gln Glu Ile Val Cys Tyr Glu Ser Pro Arg Pro
                100                 105                 110

Thr Val Gly Ile His Arg Leu Val Phe Ala Leu Phe Arg Gln Leu Gly
```

```
            115                 120                 125
Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Leu Tyr
145                 150                 155                 160

Cys Asn Cys Gln Arg Glu Ser Gly Ser Gly Gly Arg Arg Arg
                165                 170
```

```
<210> SEQ ID NO 40
<211> LENGTH: 175
<212> TYPE: PRT
<213> ORGANISM: Eucalyptus grandis

<400> SEQUENCE: 40

Met Ser Met Ser Thr Arg Asp Pro Leu Val Val Gly Arg Val Ile Gly
1               5                   10                  15

Asp Val Leu Asp Ala Phe Thr Arg Ser Ile Ser Leu Arg Val Ile Tyr
                20                  25                  30

Asn Asn Arg Glu Val Ser Asn Ser Cys Glu Leu Lys Pro Ser Gln Val
            35                  40                  45

Val Asn Gln Pro Arg Ile Glu Ile Gly Gly Asp Asp Leu Arg Thr Phe
        50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Ala Thr
                85                  90                  95

Thr Gly Ala Ser Phe Gly Gln Glu Ile Val Cys Tyr Glu Ser Pro Arg
            100                 105                 110

Pro Ser Met Gly Ile His Arg Phe Val Phe Val Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Ser Pro Val Ala Ala Leu
145                 150                 155                 160

Tyr Phe Asn Cys Gln Arg Glu Ser Gly Ser Gly Gly Arg Arg Arg
                165                 170                 175
```

```
<210> SEQ ID NO 41
<211> LENGTH: 174
<212> TYPE: PRT
<213> ORGANISM: Nelumbo nucifera

<400> SEQUENCE: 41

Met Pro Arg Glu Arg Asp Pro Leu Val Val Gly Arg Val Ile Gly Asp
1               5                   10                  15

Val Leu Asp His Phe Asn Lys Ser Ile Ser Leu Arg Val Thr Tyr Asn
                20                  25                  30

Ser Arg Asp Val Thr Asn Gly Cys Glu Phe Lys Pro Ser Leu Val Ile
            35                  40                  45

Asn Gln Pro Arg Val Glu Ile Gly Gly Asp Asp Leu Arg Thr Phe Tyr
        50                  55                  60

Thr Leu Val Met Val Asp Pro Asp Ala Pro Ser Pro Ser Asn Pro Asn
65                  70                  75                  80

Leu Lys Glu Tyr Leu His Trp Leu Val Thr Asp Ile Pro Ala Thr Thr
                85                  90                  95

Gly Ala Ser Phe Gly Gln Glu Ile Val Cys Tyr Glu Ser Pro Arg Pro
```

```
            100                 105                 110
Thr Ile Gly Ile His Arg Phe Val Phe Val Leu Phe Arg Gln Leu Gly
            115                 120                 125
Arg Gln Thr Val Tyr Ala Pro Gly Trp Arg Gln Asn Phe Asn Thr Arg
        130                 135                 140
Asp Phe Ala Glu Leu Tyr Asn Leu Gly Leu Pro Val Ala Ala Val Tyr
145                 150                 155                 160
Tyr Asn Cys Gln Arg Glu Ser Gly Ser Gly Gly Arg Arg Arg
                    165                 170
```

<210> SEQ ID NO 42
<211> LENGTH: 174
<212> TYPE: PRT
<213> ORGANISM: Sesamum indicum

<400> SEQUENCE: 42

```
Met Pro Arg Asp Arg Asp Pro Leu Val Val Gly Arg Val Gly Asp
1               5                   10                  15
Val Leu Asp Pro Phe Thr Arg Ser Val Gly Leu Arg Val Ile Tyr Ser
                20                  25                  30
Ser Arg Glu Val Ser Asn Gly Cys Glu Phe Arg Pro Ser Gln Val Leu
            35                  40                  45
Asn Gln Pro Arg Val Asp Val Gly Gly Asp Leu Arg Thr Phe Phe
        50                  55                  60
Thr Leu Val Met Val Asp Pro Asp Ala Pro Ser Pro Ser Asp Pro Ser
65                  70                  75                  80
Leu Arg Glu Tyr Leu His Trp Leu Val Thr Asp Ile Pro Ala Thr Thr
                85                  90                  95
Gly Ala Ser Phe Gly Gln Glu Ile Val Cys Tyr Glu Asn Pro Arg Pro
            100                 105                 110
Ser Met Gly Ile His Arg Phe Val Phe Val Leu Phe Arg Gln Leu Gly
        115                 120                 125
Arg Gln Thr Val Tyr Ala Pro Gly Trp Arg Gln Asn Phe Asn Thr Arg
        130                 135                 140
Asp Phe Ala Glu Leu Tyr Asn Leu Gly Ser Pro Val Ala Ala Val Tyr
145                 150                 155                 160
Tyr Asn Cys Gln Arg Glu Ser Gly Thr Gly Gly Arg Arg Arg
                    165                 170
```

<210> SEQ ID NO 43
<211> LENGTH: 174
<212> TYPE: PRT
<213> ORGANISM: Litchi chinensis

<400> SEQUENCE: 43

```
Met Pro Arg Asp Arg Asp Pro Leu Val Val Gly Arg Val Ile Gly Asp
1               5                   10                  15
Val Leu Asn Pro Phe Thr Lys Ser Ile Ser Leu Thr Val Ser Tyr Asn
                20                  25                  30
Asn Arg Glu Ile Asn Asn Gly Cys Glu Leu Lys Pro Ser Gln Ile Ala
            35                  40                  45
Asn Gln Pro Arg Val Asp Ile Gly Gly Asp Leu Arg Thr Phe Tyr
        50                  55                  60
Thr Leu Val Met Val Asp Pro Asp Ala Pro Ser Pro Ser Glu Pro Arg
65                  70                  75                  80
Leu Arg Glu Tyr Leu His Trp Leu Val Thr Asp Ile Pro Ala Thr Thr
```

```
                 85                  90                  95

Gly Ala Thr Phe Gly Gln Glu Val Val Cys Tyr Glu Ser Pro Arg Pro
            100                 105                 110

Thr Ser Gly Ile His Arg Phe Ile Phe Val Leu Phe Arg Gln Leu Gly
            115                 120                 125

Arg Gln Thr Val Tyr Ala Pro Gly Trp Arg Gln Asn Phe Asn Thr Lys
        130                 135                 140

Glu Phe Ala Glu Leu Tyr Asn Leu Gly Ser Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 44
<211> LENGTH: 174
<212> TYPE: PRT
<213> ORGANISM: Vitis labrusca x Vitis vinifera

<400> SEQUENCE: 44

Met Pro Arg Glu Arg Asp Pro Leu Val Val Gly Arg Val Val Gly Asp
1               5                   10                  15

Val Leu Asp Pro Phe Leu Arg Ser Ile Thr Leu Arg Val Thr Tyr Asn
            20                  25                  30

Asn Arg Glu Val Ala Asn Gly Cys Glu Phe Arg Pro Ser Gln Leu Val
        35                  40                  45

Ser Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asn Pro Asn
65                  70                  75                  80

Leu Arg Glu Tyr Leu His Trp Leu Val Thr Asp Ile Pro Ala Thr Thr
                85                  90                  95

Gly Ala Asn Phe Gly Gln Glu Ile Val Cys His Glu Ser Pro Arg Pro
            100                 105                 110

Thr Ala Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
        130                 135                 140

Asp Phe Ala Glu Leu Tyr Asn Leu Gly Leu Pro Val Ala Ala Val Tyr
145                 150                 155                 160

Phe Asn Cys Gln Arg Glu Gly Gly Ser Gly Gly Arg Arg Ser
                165                 170

<210> SEQ ID NO 45
<211> LENGTH: 174
<212> TYPE: PRT
<213> ORGANISM: Vitis vinifera

<400> SEQUENCE: 45

Met Pro Arg Glu Arg Asp Pro Leu Val Val Gly Arg Val Val Gly Asp
1               5                   10                  15

Val Leu Asp Pro Phe Leu Arg Ser Ile Thr Leu Arg Val Thr Tyr Asn
            20                  25                  30

Asn Arg Glu Val Ala Asn Gly Cys Glu Phe Arg Pro Ser Gln Leu Val
        35                  40                  45

Ser Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asn Pro Asn
```

```
                65                  70                  75                  80
Leu Arg Glu Tyr Leu His Trp Leu Val Thr Asp Ile Pro Ala Thr Thr
                    85                  90                  95

Gly Ala Asn Phe Gly Gln Glu Ile Val Cys Tyr Glu Ser Pro Arg Pro
                    100                 105                 110

Thr Ala Gly Ile His Arg Phe Val Phe Val Leu Phe Arg Gln Leu Gly
                    115                 120                 125

Arg Gln Thr Val Tyr Ala Pro Gly Trp Arg Gln Asn Phe Asn Thr Arg
            130                 135                 140

Asp Phe Ala Glu Leu Tyr Asn Leu Gly Leu Pro Val Ala Ala Val Tyr
145                 150                 155                 160

Phe Asn Cys Gln Arg Glu Gly Gly Ser Gly Gly Arg Arg Ser
                    165                 170

<210> SEQ ID NO 46
<211> LENGTH: 173
<212> TYPE: PRT
<213> ORGANISM: Paeonia x lemoinei

<400> SEQUENCE: 46

Met Pro Arg Asn Arg Asp Pro Leu Val Val Gly Arg Val Val Gly Asp
1               5                   10                  15

Val Leu Asp Pro Phe Thr Arg Thr Ile Ser Leu Arg Val Thr Tyr Thr
                20                  25                  30

Ser Arg Glu Val Ser Asn Gly Cys Glu Leu Lys Pro Ser Gln Val Val
            35                  40                  45

Asn Gln Pro Arg Val Asp Ile Gly Gly Asp Asp Leu Arg Thr Phe Tyr
        50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                    85                  90                  95

Gly Ala Asn Phe Gly Gln Glu Ile Val Cys Tyr Glu Ser Pro Arg Pro
                    100                 105                 110

Thr Ala Gly Ile His Arg Phe Cys Phe Ile Leu Phe Arg Gln Leu Gly
                    115                 120                 125

Arg Gln Thr Val Tyr Thr Pro Gly Trp Arg Gln Asn Phe Asn Thr Arg
            130                 135                 140

Asp Phe Ala Glu Leu Tyr Asn Leu Gly Ser Pro Val Ala Ala Val Tyr
145                 150                 155                 160

Phe Asn Cys Gln Arg Glu Arg Gly Ser Gly Gly Arg Arg
                    165                 170

<210> SEQ ID NO 47
<211> LENGTH: 176
<212> TYPE: PRT
<213> ORGANISM: Jatropha curcas

<400> SEQUENCE: 47

Met Pro Arg Asp Gln Phe Arg Asp Pro Leu Val Val Gly Arg Val Ile
1               5                   10                  15

Gly Asp Val Leu Asp Pro Phe Thr Lys Ser Ile Ser Leu Gln Val Thr
                20                  25                  30

Tyr Asn His Arg Glu Val Asn Asn Gly Cys Glu Leu Lys Pro Ser Gln
            35                  40                  45

Val Val Asn Gln Pro Arg Val Asp Ile Gly Gly Asp Asp Leu Arg Thr
```

```
            50                  55                  60
Phe Tyr Thr Leu Val Met Val Asp Pro Asp Ala Pro Ser Pro Ser Asp
 65                  70                  75                  80

Pro Asn Leu Arg Glu Tyr Leu His Trp Leu Val Thr Asp Ile Pro Ala
                 85                  90                  95

Thr Thr Gly Val Thr Phe Gly Gln Glu Ile Val Cys Tyr Glu Ser Pro
            100                 105                 110

Arg Pro Ser Leu Gly Ile His Arg Phe Val Phe Ile Leu Phe Arg Gln
        115                 120                 125

Leu Gly Arg Gln Thr Val Tyr Pro Pro Gly Trp Arg Gln Asn Phe Asn
    130                 135                 140

Thr Arg Asp Phe Ala Glu Leu Tyr Asn Leu Gly Ser Pro Val Ala Ala
145                 150                 155                 160

Val Tyr Phe Asn Cys Gln Arg Glu Ser Gly Thr Gly Arg Arg Arg
                165                 170                 175

<210> SEQ ID NO 48
<211> LENGTH: 179
<212> TYPE: PRT
<213> ORGANISM: Cucurbita moschata

<400> SEQUENCE: 48

Met Pro Arg Asp Arg Asp Pro Leu Val Ile Gly Arg Val Ile Gly Asp
 1               5                  10                  15

Val Ile Asp Ser Phe Thr Arg Ser Ile Ser Ile Arg Ala Thr Tyr Asn
                20                  25                  30

Asn Arg Glu Ile Ser Asn Gly Cys Glu Leu Lys Pro Ser Gln Val Val
             35                  40                  45

Asn Gln Pro Arg Val Glu Ile Gly Gly Thr Asp Leu Arg Thr Phe Phe
         50                  55                  60

Thr Leu Val Met Val Asp Pro Asp Ala Pro Ser Pro Ser Asp Pro Asn
 65                  70                  75                  80

Leu Arg Glu Tyr Leu His Trp Leu Val Thr Asp Ile Pro Ala Thr Thr
                 85                  90                  95

Gly Ala Thr Phe Gly Gln Glu Ile Val Cys Tyr Glu Ser Pro Arg Pro
            100                 105                 110

Thr Val Gly Ile His Arg Leu Val Leu Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg Ser Gln
                165                 170                 175

Asp Asp Phe

<210> SEQ ID NO 49
<211> LENGTH: 179
<212> TYPE: PRT
<213> ORGANISM: Cucumis sativus

<400> SEQUENCE: 49

Met Pro Arg Asp Arg Asp Pro Leu Val Val Gly Arg Val Ile Gly Asp
 1               5                  10                  15

Val Val Asp Pro Phe Ser Arg Ser Ile Ser Ile Arg Val Thr Tyr Ser
                20                  25                  30
```

```
Thr Lys Glu Val Asn Asn Gly Cys Glu Leu Lys Pro Ser Gln Val Val
         35                  40                  45

Asn Gln Pro Arg Val Glu Ile Gly Gly Thr Asp Leu Arg Thr Phe Phe
 50                      55                  60

Thr Leu Val Met Val Asp Pro Asp Ala Pro Ser Pro Ser Asp Pro Asn
 65                  70                  75                  80

Leu Arg Glu Tyr Leu His Trp Leu Val Thr Asp Ile Pro Ala Thr Thr
                 85                  90                  95

Gly Ala Thr Phe Gly Gln Glu Ile Val Cys Tyr Glu Ser Pro Arg Pro
                100                 105                 110

Thr Val Gly Ile His Arg Phe Val Leu Val Leu Phe Arg Gln Leu Gly
             115                 120                 125

Arg Gln Thr Val Tyr Ala Pro Gly Trp Arg Gln Asn Phe Asn Thr Arg
130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Arg Arg Val Gln
                165                 170                 175

Asp Asp Tyr

<210> SEQ ID NO 50
<211> LENGTH: 174
<212> TYPE: PRT
<213> ORGANISM: Populus nigra

<400> SEQUENCE: 50

Met Ser Arg Asp Arg Asp Pro Leu Ser Val Gly Arg Val Ile Gly Asp
 1               5                  10                  15

Val Leu Asp Pro Phe Thr Lys Ser Ile Ser Leu Arg Val Thr Tyr Ser
                 20                  25                  30

Ser Arg Glu Val Asn Asn Gly Cys Glu Leu Lys Pro Ser Gln Val Ala
         35                  40                  45

Asn Gln Pro Arg Val Asp Ile Gly Gly Glu Asp Leu Arg Thr Phe Tyr
 50                      55                  60

Thr Leu Val Met Val Asp Pro Asp Ala Pro Ser Pro Ser Asp Pro Ser
 65                  70                  75                  80

Leu Arg Glu Tyr Leu His Trp Leu Val Thr Asp Ile Pro Ala Thr Thr
                 85                  90                  95

Gly Ala Ser Phe Gly His Glu Thr Val Cys Tyr Glu Asn Pro Arg Pro
                100                 105                 110

Thr Met Gly Ile His Arg Phe Val Phe Val Leu Phe Arg Gln Leu Gly
             115                 120                 125

Arg Gln Thr Val Tyr Ala Pro Gly Trp Arg Gln Asn Phe Asn Thr Arg
130                 135                 140

Asp Phe Ala Glu Val Tyr Asn Leu Gly Ser Pro Val Ala Ala Val Tyr
145                 150                 155                 160

Phe Asn Cys Gln Arg Glu Ser Gly Ser Gly Gly Arg Arg
                165                 170

<210> SEQ ID NO 51
<211> LENGTH: 174
<212> TYPE: PRT
<213> ORGANISM: Populus trichocarpa

<400> SEQUENCE: 51
```

Met Ser Arg Asp Arg Asp Pro Leu Ser Val Gly Arg Val Ile Gly Asp
1               5                   10                  15

Val Leu Asp Pro Phe Thr Lys Ser Ile Ser Leu Arg Val Thr Tyr Ser
            20                  25                  30

Ser Arg Glu Val Asn Asn Gly Cys Glu Leu Lys Pro Ser Gln Val Ala
        35                  40                  45

Asn Gln Pro Arg Val Asp Ile Gly Gly Glu Asp Leu Arg Thr Phe Tyr
    50                  55                  60

Thr Leu Val Met Val Asp Pro Asp Ala Pro Ser Pro Ser Asp Pro Ser
65                  70                  75                  80

Leu Arg Glu Tyr Leu His Trp Leu Val Thr Asp Ile Pro Ala Thr Thr
                85                  90                  95

Gly Ala Ser Phe Gly His Glu Thr Val Cys Tyr Glu Ser Pro Arg Pro
            100                 105                 110

Thr Met Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Val Tyr Asn Leu Gly Ser Pro Val Ala Ala Val Tyr
145                 150                 155                 160

Phe Asn Cys Gln Arg Glu Ser Gly Ser Gly Gly Arg Arg
                165                 170

<210> SEQ ID NO 52
<211> LENGTH: 175
<212> TYPE: PRT
<213> ORGANISM: Shorea beccariana

<400> SEQUENCE: 52

Met Pro Arg Asp Arg Leu Asp Pro Leu Val Val Gly Arg Val Val Gly
1               5                   10                  15

Asp Val Leu Asp Pro Phe Thr Arg Ser Ile Ser Leu Arg Val Ser Tyr
            20                  25                  30

Asn Asn Arg Glu Val Thr Asn Gly Cys Glu Phe Arg Pro Ser Gln Leu
        35                  40                  45

Val Asn Gln Pro Arg Val Asp Ile Gly Gly Asp Asp Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Ala Thr
                85                  90                  95

Thr Gly Ala Ser Phe Gly Gln Glu Val Val Cys Tyr Glu Asn Pro Gly
            100                 105                 110

Pro Ser Ile Gly Ile His Arg Phe Val Phe Val Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Ser Pro Val Ala Ala Val
145                 150                 155                 160

Tyr Phe Asn Cys Gln Arg Glu Thr Gly Thr Gly Arg Arg Gly
                165                 170                 175

<210> SEQ ID NO 53
<211> LENGTH: 177
<212> TYPE: PRT
<213> ORGANISM: Solanum tuberosum

<400> SEQUENCE: 53

Met Pro Arg Glu Arg Asp Pro Leu Val Val Gly Arg Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Val
            35                  40                  45

Asn Gln Pro Arg Val Glu Val Gly Gly Glu Asp Leu Arg Thr Phe Phe
        50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
            100                 105                 110

Ser Met Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
130                 135                 140

Asp Phe Ala Glu Leu Tyr Asn Leu Gly Leu Pro Val Ala Ala Val Tyr
145                 150                 155                 160

Phe Asn Cys Gln Arg Glu Thr Gly Ser Gly Gly Arg Arg Ser Ala
                165                 170                 175

Asp

<210> SEQ ID NO 54
<211> LENGTH: 177
<212> TYPE: PRT
<213> ORGANISM: Nicotiana tomentosiformis

<400> SEQUENCE: 54

Met Pro Arg Glu Arg Glu Pro Leu Val Val Gly Arg Val Ile Gly Asp
1               5                   10                  15

Val Leu Asp Pro Phe Thr Arg Ser Ile Gly Leu Gly Val Ile Tyr Arg
            20                  25                  30

Asp Arg Glu Val Asn Asn Gly Cys Glu Leu Arg Pro Ser Gln Val Ile
            35                  40                  45

Asn Gln Pro Arg Val Glu Val Gly Gly Asp Asp Leu Arg Thr Phe Tyr
        50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Ile Val Cys Tyr Glu Ser Pro Arg Pro
            100                 105                 110

Thr Met Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Lys
130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Ser Ala
                165                 170                 175

Asp

<210> SEQ ID NO 55
<211> LENGTH: 177
<212> TYPE: PRT
<213> ORGANISM: Nicotiana sylvestris

<400> SEQUENCE: 55

Met Pro Arg Glu Arg Glu Pro Leu Val Val Gly Arg Val Ile Gly Asp
1               5                   10                  15

Val Leu Asp Pro Phe Thr Arg Ser Ile Gly Leu Arg Val Ile Tyr Arg
            20                  25                  30

Asp Arg Glu Val Asn Asn Gly Cys Glu Leu Arg Pro Ser Gln Val Val
        35                  40                  45

Asn Gln Pro Arg Val Glu Val Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Ile Val Cys Tyr Glu Ser Pro Arg Pro
            100                 105                 110

Thr Met Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Lys
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Ser Ala
                165                 170                 175

Asp

<210> SEQ ID NO 56
<211> LENGTH: 174
<212> TYPE: PRT
<213> ORGANISM: Camellia sinensis

<400> SEQUENCE: 56

Met Pro Arg Asp Arg Asp Pro Leu Val Val Gly Arg Val Ile Gly Asp
1               5                   10                  15

Val Leu Asp Pro Phe Thr Arg Ser Ile Ser Leu Arg Val Thr Tyr Ser
            20                  25                  30

Ser Arg Glu Val Thr Asn Gly Cys Glu Leu Arg Pro Ser Gln Val Val
        35                  40                  45

Ile Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Val Cys Tyr Glu Ser Pro Arg Pro
            100                 105                 110

Ser Met Gly Ile His Arg Phe Val Leu Val Leu Phe Arg Gln Leu Gly
        115                 120                 125

Arg Gln Thr Val Tyr Ala Pro Gly Trp Arg Gln Asn Phe Asn Thr Arg
    130                 135                 140

```
Asp Phe Ala Glu Leu Tyr Asn Leu Gly Ser Pro Val Ala Ala Val Tyr
145                 150                 155                 160

Phe Asn Cys Gln Arg Glu Thr Gly Ser Gly Gly Arg Arg Arg
                165                 170
```

<210> SEQ ID NO 57
<211> LENGTH: 174
<212> TYPE: PRT
<213> ORGANISM: Populus tomentosa

<400> SEQUENCE: 57

```
Met Pro Arg Asp Arg Glu Pro Leu Ser Val Gly Arg Val Ile Gly Asp
1               5                   10                  15

Val Leu Asp Pro Phe Thr Arg Ser Val Ser Leu Arg Val Ser Tyr Asn
                20                  25                  30

Ser Arg Glu Val Asn Asn Gly Cys Glu Leu Lys Pro Ser His Val Val
            35                  40                  45

Asn Gln Pro Arg Val Asp Ile Gly Gly Glu Asp Leu Arg Thr Phe Tyr
        50                  55                  60

Thr Leu Val Met Val Asp Pro Asp Ala Pro Ser Pro Ser Asn Pro Asn
65                  70                  75                  80

Leu Arg Glu Tyr Leu His Trp Leu Val Thr Asp Ile Pro Ala Thr Thr
                85                  90                  95

Gly Ala Asn Phe Gly Gln Glu Val Val Cys Tyr Glu Ser Pro Arg Pro
            100                 105                 110

Thr Ala Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
130                 135                 140

Asp Phe Ala Glu Leu Tyr Asn Leu Gly Ser Pro Val Ala Ala Val Tyr
145                 150                 155                 160

Phe Asn Cys Gln Arg Glu Ser Gly Ser Gly Gly Arg Arg Pro
                165                 170
```

<210> SEQ ID NO 58
<211> LENGTH: 174
<212> TYPE: PRT
<213> ORGANISM: Prunus persica

<400> SEQUENCE: 58

```
Met Pro Arg Asp Arg Asp Pro Leu Val Val Gly Arg Val Val Gly Asp
1               5                   10                  15

Val Leu Asp Pro Phe Thr Arg Ser Val Ser Leu Arg Val Thr Tyr Gly
                20                  25                  30

Met Lys Glu Val Asn Asn Gly Cys Glu Leu Lys Pro Ser Gln Val Val
            35                  40                  45

Gln Gln Pro Arg Val Asp Thr Gly Gly Asp Asp Leu Arg Thr Phe Tyr
        50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110

Thr Val Gly Ile His Arg Phe Val Leu Val Leu Phe Arg Gln Leu Gly
        115                 120                 125
```

```
Arg Gln Thr Val Tyr Ala Pro Gly Trp Arg Gln Asn Phe Asn Thr Arg
            130                 135                 140

Asp Phe Ala Glu Leu Tyr Asn Leu Gly Leu Pro Val Ser Ala Val Tyr
145                 150                 155                 160

Phe Asn Cys Gln Arg Glu Ser Gly Ser Gly Gly Arg Arg Arg
                165                 170

<210> SEQ ID NO 59
<211> LENGTH: 174
<212> TYPE: PRT
<213> ORGANISM: Prunus mume

<400> SEQUENCE: 59

Met Pro Arg Asp Arg Asp Pro Leu Val Val Gly Arg Val Val Gly Asp
1               5                   10                  15

Val Leu Asp Pro Phe Thr Arg Ser Val Ser Leu Arg Val Thr Tyr Gly
            20                  25                  30

Leu Lys Glu Val Asn Asn Gly Cys Glu Leu Lys Pro Ser Gln Val Val
        35                  40                  45

Gln Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110

Thr Val Gly Ile His Arg Phe Val Leu Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 60
<211> LENGTH: 173
<212> TYPE: PRT
<213> ORGANISM: Prunus pseudocerasus

<400> SEQUENCE: 60

Met Pro Arg Asp Arg Asp Pro Leu Val Val Gly Arg Val Val Gly Asp
1               5                   10                  15

Val Leu Asp Pro Phe Thr Arg Ser Val Ser Leu Arg Val Thr Tyr Gly
            20                  25                  30

Val Lys Glu Val Asn Asn Gly Cys Glu Leu Lys Pro Ser Gln Val Val
        35                  40                  45

His Gln Pro Arg Val Asp Thr Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110
```

Thr Val Gly Ile His Arg Phe Val Leu Val Phe Arg Gln Leu Gly
            115                 120                 125

Arg Gln Thr Val Tyr Ala Pro Gly Trp Arg Gln Asn Phe Asn Thr Arg
        130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg
                165                 170

<210> SEQ ID NO 61
<211> LENGTH: 174
<212> TYPE: PRT
<213> ORGANISM: Eriobotrya deflexa

<400> SEQUENCE: 61

Met Pro Arg Asp Arg Asp Pro Leu Val Val Gly Arg Val Gly Asp
1               5                   10                  15

Val Leu Asp Pro Phe Thr Arg Ser Val Ser Leu Arg Val Thr Tyr Gly
                20                  25                  30

Asn Lys Glu Val Asn Asn Gly Cys Glu Leu Lys Pro Ser Gln Val Val
            35                  40                  45

His Gln Pro Arg Val Asp Thr Gly Gly Asp Leu Arg Ile Phe Tyr
        50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110

Thr Val Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
        130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg
                165                 170

<210> SEQ ID NO 62
<211> LENGTH: 174
<212> TYPE: PRT
<213> ORGANISM: Pyrus x bretschneideri

<400> SEQUENCE: 62

Met Pro Arg Asp Arg Asp Pro Leu Val Val Gly Arg Val Val Gly Asp
1               5                   10                  15

Val Leu Asp Pro Phe Thr Arg Ser Val Ser Leu Arg Val Thr Tyr Gly
                20                  25                  30

Asn Lys Glu Val Asn Asn Gly Cys Glu Leu Lys Pro Ser Gln Val Val
            35                  40                  45

Gln Gln Pro Arg Val Asp Thr Gly Gly Asp Leu Arg Thr Phe Tyr
        50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

```
Ala Ala Ser Phe Gly Gln Glu Ile Val Cys Tyr Glu Ser Pro Arg Pro
            100                 105                 110

Thr Val Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 63
<211> LENGTH: 174
<212> TYPE: PRT
<213> ORGANISM: Malus domestica

<400> SEQUENCE: 63

Met Pro Arg Asp Arg Asp Pro Leu Val Val Gly Arg Val Gly Asp
1               5                   10                  15

Val Leu Asp Pro Phe Thr Arg Ser Val Ser Leu Arg Val Thr Tyr Gly
                20                  25                  30

Asn Lys Glu Val Asn Asn Gly Cys Glu Leu Lys Pro Ser Gln Val Val
            35                  40                  45

His Gln Pro Arg Val Asp Thr Gly Gly Asp Asp Leu Arg Thr Phe Tyr
        50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110

Thr Val Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 64
<211> LENGTH: 174
<212> TYPE: PRT
<213> ORGANISM: Carica papaya

<400> SEQUENCE: 64

Met Thr Arg Asp Arg Asp Pro Leu Val Val Gly Arg Val Ile Gly Asp
1               5                   10                  15

Val Leu Asp Pro Phe Ile Arg Ser Ile Ser Leu Arg Val Asn Tyr Asn
                20                  25                  30

Ser Arg Glu Val Asn Asn Gly Cys Glu Leu Lys Pro Ser Gln Val Val
            35                  40                  45

Ser Gln Pro Arg Val Asp Ile Gly Gly Asp Asp Leu Arg Thr Phe Tyr
        50                  55                  60

Thr Leu Val Met Val Asp Pro Asp Ala Pro Ser Pro Ser Asp Pro Asn
65                  70                  75                  80
```

```
Leu Arg Glu Tyr Leu His Trp Leu Val Thr Asp Ile Pro Ala Thr Thr
                85                  90                  95

Gly Ala Ser Phe Gly Gln Glu Ile Val Cys Tyr Glu Asn Pro Arg Pro
            100                 105                 110

Thr Val Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ser Val Tyr
145                 150                 155                 160

Phe Asn Cys Gln Arg Glu Ser Gly Ser Gly Gly Arg Arg Arg
                165                 170
```

<210> SEQ ID NO 65
<211> LENGTH: 174
<212> TYPE: PRT
<213> ORGANISM: Betula platyphylla

<400> SEQUENCE: 65

```
Met Pro Arg Glu Arg Asp Pro Leu Ala Val Gly Arg Val Ile Gly Asp
1               5                   10                  15

Val Leu Glu Pro Phe Thr Arg Ser Ile Ser Leu Arg Val Thr Tyr Asn
            20                  25                  30

Asn Arg Glu Val Asn Asn Gly Cys Glu Leu Lys Pro Ser Gln Val Val
        35                  40                  45

Asn Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Val Val Cys Tyr Glu Ser Pro Leu Pro
            100                 105                 110

Thr Val Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Gly Phe Ala Glu Leu Tyr Asn Leu Gly Leu Pro Val Ala Ala Leu Tyr
145                 150                 155                 160

Phe Asn Cys Gln Arg Glu Ser Gly Ser Gly Gly Arg Arg Arg
                165                 170
```

<210> SEQ ID NO 66
<211> LENGTH: 174
<212> TYPE: PRT
<213> ORGANISM: Betula luminifera

<400> SEQUENCE: 66

```
Met Pro Arg Glu Arg Asp Pro Leu Ala Val Gly Arg Val Ile Gly Asp
1               5                   10                  15

Val Leu Glu Pro Phe Thr Arg Ser Ile Ser Leu Arg Val Thr Tyr Asn
            20                  25                  30

Ser Arg Glu Val Asn Asn Gly Cys Glu Leu Lys Pro Ser Gln Val Val
        35                  40                  45

Asn Gln Pro Arg Val Asp Ile Gly Gly Asp Asp Leu Arg Thr Phe Tyr
    50                  55                  60
```

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Val Val Cys Tyr Glu Ser Pro Arg Pro
            100                 105                 110

Thr Val Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Leu Tyr
145                 150                 155                 160

Phe Asn Cys Gln Arg Glu Ser Gly Ser Gly Gly Arg Arg Arg
                165                 170

<210> SEQ ID NO 67
<211> LENGTH: 174
<212> TYPE: PRT
<213> ORGANISM: Gossypium hirsutum

<400> SEQUENCE: 67

Met Pro Arg Asp Arg Asp Pro Leu Val Val Gly Arg Val Ile Gly Asp
1               5                   10                  15

Val Leu Asp Pro Phe Thr Arg Ser Ile Ser Leu Arg Val Thr Tyr Ala
            20                  25                  30

Thr Arg Asp Val Asn Asn Gly Val Glu Leu Lys Pro Ser Gln Val Val
        35                  40                  45

Asn Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Val Val Cys Tyr Glu Ser Pro Arg Pro
            100                 105                 110

Thr Val Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Thr
                165                 170

<210> SEQ ID NO 68
<211> LENGTH: 174
<212> TYPE: PRT
<213> ORGANISM: Gossypium raimondii

<400> SEQUENCE: 68

Met Pro Arg Asp Arg Asp Pro Leu Val Val Gly Arg Val Ile Gly Asp
1               5                   10                  15

Val Leu Asp Pro Phe Thr Arg Ser Ile Ser Leu Arg Val Thr Tyr Ala
            20                  25                  30

Thr Arg Asp Val Ser Asn Gly Val Glu Leu Lys Pro Ser Gln Val Val
        35                  40                  45

Asn Gln Pro Arg Val Asp Ile Gly Gly Asp Leu Arg Thr Phe Tyr
            50                  55                  60

Thr Leu Val Met Val Asp Pro Asp Ala Pro Ser Pro Ser Asp Pro Asn
 65                  70                  75                  80

Leu Arg Glu Tyr Leu His Trp Leu Val Thr Asp Ile Pro Ala Thr Thr
                    85                  90                  95

Gly Ala Ser Phe Gly Gln Glu Val Val Cys Tyr Glu Ser Pro Arg Pro
                100                 105                 110

Thr Val Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
            130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Thr
                165                 170

<210> SEQ ID NO 69
<211> LENGTH: 174
<212> TYPE: PRT
<213> ORGANISM: Fagus crenata

<400> SEQUENCE: 69

Met Pro Arg Asp Arg Asp Pro Leu Val Val Gly Arg Val Ile Gly Asp
 1               5                  10                  15

Val Leu Asp Pro Phe Thr Arg Ser Ile Ser Leu Arg Ala Asn Tyr Asn
                20                  25                  30

Asn Arg Glu Val Asn Asn Gly Cys Glu Leu Lys Pro Ser Gln Val Val
            35                  40                  45

Asn Gln Pro Arg Val Asp Ile Gly Gly Glu Asp Leu Arg Thr Phe Tyr
            50                  55                  60

Thr Leu Val Met Val Asp Pro Asp Ala Pro Ser Pro Ser Asp Pro Asn
 65                  70                  75                  80

Leu Arg Glu Tyr Leu His Trp Leu Val Thr Asp Ile Pro Ala Thr Thr
                    85                  90                  95

Gly Ala Ser Phe Gly Gln Glu Val Val Cys Tyr Glu Ser Pro Arg Pro
                100                 105                 110

Thr Val Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
            130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 70
<211> LENGTH: 174
<212> TYPE: PRT
<213> ORGANISM: Theobroma cacao

<400> SEQUENCE: 70

Met Pro Arg Glu Arg Asp Pro Leu Val Val Gly Arg Val Ile Gly Asp
 1               5                  10                  15

Val Leu Asp Pro Phe Thr Arg Ser Ile Ser Leu Arg Val Thr Phe Ala
                20                  25                  30

```
Cys Arg Glu Val Asn Asn Gly Cys Glu Leu Lys Pro Ser Gln Val Val
            35                  40                  45

Asn Gln Pro Arg Val Asp Ile Gly Gly Asp Asp Leu Arg Thr Phe Tyr
     50                  55                  60

Thr Leu Val Met Val Asp Pro Asp Ala Pro Ser Pro Ser Asp Pro Asn
 65                  70                  75                  80

Leu Arg Glu Tyr Leu His Trp Leu Val Thr Asp Ile Pro Ala Thr Thr
                 85                  90                  95

Gly Ala Ser Phe Gly Gln Glu Val Val Cys Tyr Glu Ser Pro Arg Pro
                100                 105                 110

Thr Val Gly Ile His Arg Phe Leu Phe Val Leu Phe Arg Gln Leu Gly
                115                 120                 125

Arg Gln Thr Val Tyr Ala Pro Gly Trp Arg Gln Asn Phe Asn Thr Arg
        130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 71
<211> LENGTH: 174
<212> TYPE: PRT
<213> ORGANISM: Ficus carica

<400> SEQUENCE: 71

Met Pro Arg Glu Arg Asp Pro Leu Val Val Gly Arg Val Ile Gly Asp
 1               5                  10                  15

Val Leu Asp Gln Phe Thr Arg Ser Ile Ser Leu Arg Val Thr Tyr Gly
                 20                  25                  30

Asn Lys Glu Val Asn Asn Gly Cys Glu Leu Lys Pro Ser Gln Val Val
            35                  40                  45

Ser Gln Pro Arg Val Asp Ile Gly Gly Asp Asp Leu Arg Thr Phe Tyr
     50                  55                  60

Thr Leu Val Met Val Asp Pro Asp Ala Pro Ser Pro Ser Asp Pro Ser
 65                  70                  75                  80

Leu Arg Glu Tyr Leu His Trp Leu Val Thr Asp Ile Pro Ala Thr Thr
                 85                  90                  95

Gly Ala Ser Phe Gly Gln Glu Val Val Cys Tyr Glu Ser Pro Arg Pro
                100                 105                 110

Thr Val Gly Ile His Arg Phe Val Phe Val Leu Phe Arg Gln Leu Gly
                115                 120                 125

Arg Gln Thr Val Tyr Ala Pro Gly Trp Arg Gln Asn Phe Asn Thr Lys
        130                 135                 140

Asp Phe Ala Glu Leu Tyr Asn Leu Gly Leu Pro Val Ala Ala Val Tyr
145                 150                 155                 160

Tyr Asn Cys Gln Arg Glu Ser Gly Ser Gly Gly Arg Arg Arg
                165                 170

<210> SEQ ID NO 72
<211> LENGTH: 174
<212> TYPE: PRT
<213> ORGANISM: Ziziphus jujuba

<400> SEQUENCE: 72

Met Pro Arg Glu Arg Asp Pro Leu Val Val Gly Arg Val Ile Gly Asp
 1               5                  10                  15
```

-continued

Val Leu Asp Pro Phe Thr Arg Ser Ile Ser Leu Arg Val Ser Tyr Gly
            20                  25                  30

Asn Arg Glu Val Asn Asn Gly Cys Glu Leu Lys Pro Ser His Val Val
        35                  40                  45

Ser Gln Pro Arg Val Asp Ile Gly Gly Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ala Ser Phe Gly Gln Glu Val Val Cys Tyr Glu Ser Pro Arg Pro
            100                 105                 110

Thr Val Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 73
<211> LENGTH: 181
<212> TYPE: PRT
<213> ORGANISM: Tarenaya hassleriana

<400> SEQUENCE: 73

Met Arg Gly Ser Ile Asp Gln Asn Met Thr Val Val Arg Asp Pro Leu
1               5                   10                  15

Val Val Gly Arg Val Val Gly Asp Val Leu Asp Pro Phe Thr Arg Ser
            20                  25                  30

Ile Ser Leu Arg Val Thr Tyr Gln Arg Glu Val Ser Asn Gly Cys Asp
        35                  40                  45

Leu Arg Pro Ser His Val Leu His Lys Pro Arg Val Asp Ile Gly Gly
    50                  55                  60

Asp Asp Leu Arg Thr Phe Tyr Thr Leu Val Met Val Asp Pro Asp Ala
65                  70                  75                  80

Pro Ser Pro Ser Asn Pro His Leu Arg Glu Tyr Leu His Trp Leu Val
                85                  90                  95

Thr Asp Ile Pro Ala Thr Thr Gly Ala Asn Phe Gly Asn Glu Val Val
            100                 105                 110

Cys Tyr Glu Asn Pro Arg Pro Thr Ser Gly Ile His Arg Phe Val Leu
            115                 120                 125

Ile Leu Phe Arg Gln Leu Gly Arg Gln Thr Val Tyr Ala Pro Gly Trp
    130                 135                 140

Arg Gln Asn Phe Asn Thr Arg Glu Phe Ala Glu Leu Tyr Asn Leu Gly
145                 150                 155                 160

Leu Pro Val Ala Ala Val Tyr Phe Asn Cys Gln Arg Glu Ser Gly Cys
                165                 170                 175

Gly Gly Arg Arg Thr
            180

<210> SEQ ID NO 74
<211> LENGTH: 175
<212> TYPE: PRT

<213> ORGANISM: Arabis alpina

<400> SEQUENCE: 74

Met Ser Ile Ser Pro Arg Asp Pro Leu Val Gly Val Val Gly
1               5                  10                  15

Asp Val Leu Asp Ala Phe Thr Arg Ser Ile Ser Leu Arg Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ser Gly Ile His Arg Ile Val Leu Ile Leu Phe Arg Gln Leu
        115                 120                 125

Gly Arg Gln Thr Val Tyr Ala Pro Gly Trp Arg Gln Gln Phe Asn Thr
    130                 135                 140

Arg Glu Phe Ala Glu Ile Tyr Asn Leu Gly His Pro Val Ala Ala Val
145                 150                 155                 160

Phe Phe Asn Cys Gln Arg Glu Ser Gly Cys Gly Gly Arg Arg Ser
                165                 170                 175

<210> SEQ ID NO 75
<211> LENGTH: 175
<212> TYPE: PRT
<213> ORGANISM: Arabidopsis thaliana

<400> SEQUENCE: 75

Met Ser Ile Asn Ile Arg Asp Pro Leu Ile Val Ser Arg Val Val Gly
1               5                  10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

```
<210> SEQ ID NO 76
<211> LENGTH: 175
<212> TYPE: PRT
<213> ORGANISM: Arabidopsis lyrata subsp. Petraea

<400> SEQUENCE: 76
```

| Met | Ser | Ile | Asn | Ile | Arg | Glu | Pro | Leu | Ile | Val | Ser | Arg | Val | Val | Gly |
|---|---|---|---|---|---|---|---|---|---|---|---|---|---|---|---|
| 1 | | | | 5 | | | | | 10 | | | | | 15 | |

Asp Ile Leu Asp Pro Phe Asn Arg Ser Ile Ser Leu Arg Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Ile Val Leu Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Ile
                165                 170                 175

```
<210> SEQ ID NO 77
<211> LENGTH: 175
<212> TYPE: PRT
<213> ORGANISM: Arabidopsis halleri subsp. Gemmifera

<400> SEQUENCE: 77
```

Met Ser Ile Asn Ile Arg Asp Pro Leu Ile Val Ser Arg Val Val Gly
1               5                   10                  15

Asp Ile Leu Asp Pro Phe Asn Arg Ser Ile Ser Leu Arg Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Ile Val Leu Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Ile

```
                165             170             175

<210> SEQ ID NO 78
<211> LENGTH: 175
<212> TYPE: PRT
<213> ORGANISM: Arabidopsis lyrata subsp. Lyrata

<400> SEQUENCE: 78

Met Ser Ile Asn Ile Arg Asp Pro Leu Ile Val Ser Arg Val Val Gly
1               5                   10                  15

Asp Ile Leu Asp Pro Phe Asn Arg Ser Ile Ser Leu Arg Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Ile Val Val Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Ile
                165                 170                 175

<210> SEQ ID NO 79
<211> LENGTH: 175
<212> TYPE: PRT
<213> ORGANISM: Capsella rubella

<400> SEQUENCE: 79

Met Thr Ser Asn Val Arg Asp Pro Leu Ile Val Ser Arg Val Val Gly
1               5                   10                  15

Asp Val Leu Asp Pro Phe Asn Arg Ser Ile Ser Leu Arg Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Ser Ala Gly Ile His Arg Val Val Met Thr Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Thr Glu Ile Tyr Asn Leu Gly Leu Pro Val Ala Ala Val
```

```
                145                 150                 155                 160
Phe Phe Asn Cys Gln Arg Glu Ser Gly Cys Gly Gly Arg Arg Ser
                    165                 170                 175

<210> SEQ ID NO 80
<211> LENGTH: 204
<212> TYPE: PRT
<213> ORGANISM: Camelina sativa

<400> SEQUENCE: 80

Met Ile Arg Ala Glu Thr Lys Thr Gln Ser Lys Thr Lys Lys Gln Glu
1               5                   10                  15

Gln Leu Ile Gln Lys Pro Pro Val Cys Leu Arg Leu Lys Met Ser Thr
                20                  25                  30

Thr Val Arg Asp Pro Leu Ile Val Ser Arg Val Val Gly Asp Val Leu
            35                  40                  45

Asp Pro Phe Asn Arg Ser Ile Ser Leu Arg Val Thr Tyr Gly Gln Arg
        50                  55                  60

Glu Val Thr Asn Gly Leu Asp Leu Arg Pro Ser Gln Val Gln Asn Lys
65                  70                  75                  80

Pro Arg Val Glu Ile Gly Gly Glu Asp Leu Arg Asn Phe Tyr Thr Leu
                85                  90                  95

Val Met Val Asp Pro Asp Val Pro Ser Pro Ser Asn Pro His Leu Arg
            100                 105                 110

Glu Tyr Leu His Trp Leu Val Thr Asp Ile Pro Ala Thr Thr Gly Thr
        115                 120                 125

Thr Phe Gly Asn Glu Ile Val Cys Tyr Glu Asn Pro Ser Pro Ser Ala
130                 135                 140

Gly Ile His Arg Val Val Met Ile Leu Phe Arg Gln Leu Gly Arg Gln
145                 150                 155                 160

Thr Val Tyr Ala Pro Gly Trp Arg Gln Asn Phe Asn Thr Arg Glu Phe
                165                 170                 175

Ala Glu Ile Tyr Asn Leu Gly Leu Pro Val Ala Ala Val Phe Phe Asn
            180                 185                 190

Cys Gln Arg Glu Ser Gly Cys Gly Gly Arg Arg Thr
        195                 200

<210> SEQ ID NO 81
<211> LENGTH: 175
<212> TYPE: PRT
<213> ORGANISM: Boechera stricta

<400> SEQUENCE: 81

Met Ser Ile Asn Val Arg Asp Pro Leu Ile Val Ser Arg Val Val Gly
1               5                   10                  15

Asp Val Leu Asp Pro Phe Thr Arg Ser Ile Ser Leu Arg Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Thr Asp Leu Arg Asn Phe
        50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Asn Phe Gly Asn Glu Ile Val Cys Tyr Glu Asn Pro Ser
```

```
              100                 105                 110
Pro Tyr Ala Gly Ile His Arg Val Val Met Ile Leu Phe Arg Gln Leu
              115                 120                 125
Gly Arg Gln Thr Val Tyr Ala Pro Gly Trp Arg Gln Asn Phe Asn Thr
              130                 135                 140
Arg Glu Phe Ala Glu Ile Tyr Asn Leu Gly Leu Pro Val Ala Ala Val
145                 150                 155                 160
Phe Phe Asn Cys Gln Arg Glu Ser Gly Cys Gly Gly Arg Arg Asn
              165                 170                 175
```

<210> SEQ ID NO 82
<211> LENGTH: 175
<212> TYPE: PRT
<213> ORGANISM: Cardamine hirsuta

<400> SEQUENCE: 82

```
Met Ser Ile Asn Val Arg Asp Pro Leu Leu Val Ser Arg Val Val Gly
1               5                   10                  15
Asp Val Leu Asp Pro Phe Asn Arg Ser Ile Ser Leu Arg Val Thr Tyr
              20                  25                  30
Gly Gln Arg Glu Val Thr Asn Gly Leu Asp Leu Arg Pro Ser Gln Val
              35                  40                  45
Gln Asn Lys Pro Arg Val Glu Ile Gly Gly Glu Asp Leu Arg Asn Phe
          50                  55                  60
Tyr Thr Leu Val Met Val Asp Pro Asp Val Pro Ser Pro Ser Asn Pro
65                  70                  75                  80
His Leu Arg Glu Tyr Leu His Trp Leu Val Thr Asp Ile Pro Ala Thr
              85                  90                  95
Thr Gly Thr Asn Phe Gly Asn Glu Ile Val Cys Tyr Glu Asn Pro Arg
              100                 105                 110
Pro Ser Ser Gly Ile His Arg Val Val Leu Ile Leu Phe Arg Gln Leu
              115                 120                 125
Gly Arg Gln Thr Val Tyr Ala Pro Gly Trp Arg Gln Asn Phe Asn Thr
              130                 135                 140
Arg Glu Phe Ala Glu Ile Tyr Asn Leu Gly Leu Pro Val Ala Ala Val
145                 150                 155                 160
Phe Phe Asn Cys Gln Arg Glu Ser Gly Cys Gly Gly Arg Arg Ile
              165                 170                 175
```

<210> SEQ ID NO 83
<211> LENGTH: 175
<212> TYPE: PRT
<213> ORGANISM: Brassica oleracea

<400> SEQUENCE: 83

```
Met Ser Ile Asn Ile Arg Asp Pro Leu Val Val Gly Gly Val Ile Gly
1               5                   10                  15
Asp Val Leu Glu Gln Phe Thr Arg Ser Ile Asp Leu Arg Val Thr Tyr
              20                  25                  30
Gly Gln Arg Glu Val Thr Asn Gly Leu Asp Ile Arg Pro Ser Gln Ile
              35                  40                  45
Leu Asn Lys Pro Arg Val Glu Ile Gly Gly Asp Asp Leu Arg Asn Phe
          50                  55                  60
Tyr Thr Leu Val Met Val Asp Pro Asp Val Pro Ser Pro Ser Asn Pro
65                  70                  75                  80
His Leu Arg Glu Tyr Leu His Trp Leu Val Thr Asp Ile Pro Ala Thr
```

```
                    85                  90                  95

Thr Gly Thr Asn Phe Gly Asn Glu Ile Val Ser Tyr Glu Asn Pro Arg
                100                 105                 110

Pro Thr Ser Gly Ile His Arg Ile Val Leu Val Leu Phe Arg Gln Leu
                115                 120                 125

Gly Arg Gln Thr Val Tyr Glu Pro Gly Trp Arg Pro Gln Phe Asn Thr
            130                 135                 140

Arg Glu Phe Ala Ala Leu Tyr Asn Leu Gly Leu Pro Ala Ala Ala Val
145                 150                 155                 160

Tyr Phe Asp Cys Gln Arg Asp Ser Gly Cys Gly Gly Arg Arg Leu
                165                 170                 175

<210> SEQ ID NO 84
<211> LENGTH: 175
<212> TYPE: PRT
<213> ORGANISM: Brassica oleracea var. oleracea

<400> SEQUENCE: 84

Met Ser Val Asn Asn Arg Asp Pro Leu Val Gly Gly Val Ile Gly
1               5                   10                  15

Asp Val Leu Glu Arg Phe Thr Arg Ser Ile Asp Leu Arg Val Thr Tyr
                20                  25                  30

Gly Gln Arg Glu Val Thr Asn Gly Leu Asp Ile Arg Pro Ser Gln Ile
            35                  40                  45

Leu Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Asn Phe Gly Asn Glu Ile Val Ser Tyr Glu Asn Pro Arg
                100                 105                 110

Pro Thr Ser Gly Ile His Arg Ile Val Leu Val Leu Phe Arg Gln Leu
                115                 120                 125

Gly Arg Gln Thr Val Tyr Glu Pro Gly Trp Arg Pro Gln Phe Asn Thr
            130                 135                 140

Arg Glu Phe Ala Ala Leu Tyr Asn Leu Gly Leu Pro Ala Ala Ala Val
145                 150                 155                 160

Tyr Phe Asn Cys Gln Arg Asp Asn Gly Cys Gly Gly Arg Arg Ser
                165                 170                 175

<210> SEQ ID NO 85
<211> LENGTH: 175
<212> TYPE: PRT
<213> ORGANISM: Sinapis alba

<400> SEQUENCE: 85

Met Ser Val Asn His Arg Asp Pro Leu Val Val Gly Gly Val Ile Gly
1               5                   10                  15

Asp Val Leu Glu Arg Phe Thr Arg Ser Ile Asp Leu Arg Val Thr Tyr
                20                  25                  30

Gly Gln Arg Glu Val Ser Asn Gly Leu Asp Ile Arg Pro Ser Gln Ile
            35                  40                  45

Leu Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asp Pro
```

```
            65                  70                  75                  80
His Leu Arg Glu Tyr Leu His Trp Leu Val Thr Asp Ile Pro Ala Thr
                85                  90                  95

Thr Gly Thr Asn Phe Gly Asn Glu Val Val Ser Tyr Glu Asn Pro Arg
            100                 105                 110

Pro Thr Ser Gly Ile His Arg Ile Val Met Val Leu Phe Arg Gln Leu
        115                 120                 125

Gly Arg Gln Thr Val Tyr Glu Pro Gly Trp Arg Pro Gln Phe Asn Thr
    130                 135                 140

Arg Glu Phe Ala Ala Leu Tyr Asn Leu Gly Leu Pro Val Ala Ala Val
145                 150                 155                 160

Tyr Phe Asn Cys Gln Arg Asp Asn Gly Cys Gly Gly Arg Arg Ser
                165                 170                 175

<210> SEQ ID NO 86
<211> LENGTH: 175
<212> TYPE: PRT
<213> ORGANISM: Brassica carinata

<400> SEQUENCE: 86

Met Ser Leu Ser Asn Arg Asp Pro Leu Val Val Gly Arg Val Val Gly
1               5                   10                  15

Asp Val Leu Glu Cys Phe Thr Arg Ser Ile Asp Leu Arg Val Thr Tyr
            20                  25                  30

Gly Gln Arg Glu Val Thr Asn Gly Leu Asp Leu Arg Pro Ser Gln Val
        35                  40                  45

Leu Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Asn Phe Gly Asn Glu Ile Val Ser Tyr Glu Ser Pro Arg
            100                 105                 110

Pro Asn Ser Gly Ile His Arg Ile Val Leu Ile Leu Phe Arg Gln Leu
        115                 120                 125

Gly Arg Gln Thr Val Tyr Glu Pro Gly Trp Arg Gln Gln Phe Asn Thr
    130                 135                 140

Arg Glu Phe Ala Ser Leu Tyr Asn Leu Gly Leu Pro Val Ala Ala Val
145                 150                 155                 160

Phe Tyr Asn Cys Gln Arg Glu Ser Gly Cys Gly Gly Arg Arg Ser
                165                 170                 175

<210> SEQ ID NO 87
<211> LENGTH: 175
<212> TYPE: PRT
<213> ORGANISM: Brassica napus

<400> SEQUENCE: 87

Met Ser Leu Ser Asn Arg Asp Pro Leu Val Val Gly Arg Val Val Gly
1               5                   10                  15

Asp Val Leu Glu Cys Phe Thr Arg Ser Ile Asp Leu Arg Val Thr Tyr
            20                  25                  30

Gly Gln Arg Glu Val Thr Asn Gly Leu Asp Leu Arg Pro Ser Gln Val
        35                  40                  45

Ile Asn Lys Pro Arg Val Glu Ile Gly Gly Glu Asp Leu Arg Asn Phe
```

```
Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Asn Phe Gly Asn Glu Ile Val Ser Tyr Glu Ser Pro Arg
                100                 105                 110

Pro Asn Ser Gly Ile His Arg Ile Val Leu Val Leu Phe Arg Gln Leu
            115                 120                 125

Gly Arg Gln Thr Val Tyr Glu Pro Gly Trp Arg Gln Gln Phe Asn Thr
        130                 135                 140

Arg Glu Phe Ala Ser Leu Tyr Asn Leu Gly Leu Pro Val Ala Ala Val
145                 150                 155                 160

Phe Tyr Asn Cys Gln Arg Glu Ser Gly Cys Gly Gly Arg Arg Ser
                165                 170                 175
```

<210> SEQ ID NO 88
<211> LENGTH: 175
<212> TYPE: PRT
<213> ORGANISM: Brassica juncea

<400> SEQUENCE: 88

```
Met Ser Leu Ser Asn Arg Asp Pro Leu Val Val Gly Arg Val Val Gly
  1               5                  10                  15

Asp Val Leu Glu Cys Phe Thr Arg Ser Ile Asp Leu Arg Val Thr Tyr
             20                  25                  30

Gly Gln Arg Glu Val Thr Asn Gly Leu Asp Leu Arg Pro Ser Gln Val
         35                  40                  45

Leu Asn Lys Pro Arg Val Glu Ile Gly Gly Glu Asp Leu Arg Asn Phe
     50                  55                  60

Tyr Thr Leu Val Met Val Asp Pro Asp Val Pro Ser Pro Ser Pro
 65                  70                  75                  80

His Leu Arg Glu Tyr Leu His Trp Leu Val Thr Asp Ile Pro Ala Thr
                 85                  90                  95

Thr Gly Thr Asn Phe Gly Asn Glu Ile Val Ser Tyr Glu Ser Pro Arg
                100                 105                 110

Pro Asn Ser Gly Ile His Arg Ile Val Leu Val Leu Phe Arg Gln Leu
            115                 120                 125

Gly Arg Gln Thr Val Tyr Glu Pro Gly Trp Arg Gln Gln Phe Asn Thr
        130                 135                 140

Arg Glu Phe Ala Ser Leu Tyr Asn Leu Gly Leu Pro Val Ala Ala Val
145                 150                 155                 160

Phe Tyr Asn Cys Gln Arg Glu Ser Gly Cys Gly Gly Arg Arg Ser
                165                 170                 175
```

<210> SEQ ID NO 89
<211> LENGTH: 175
<212> TYPE: PRT
<213> ORGANISM: Brassica rapa

<400> SEQUENCE: 89

```
Met Ser Leu Ser Asn Arg Asp Pro Leu Val Val Gly Arg Val Val Gly
  1               5                  10                  15

Asp Val Leu Glu Cys Phe Thr Arg Ser Ile Asp Leu Arg Val Thr Tyr
             20                  25                  30

Gly Gln Arg Glu Val Thr Asn Gly Leu Asp Leu Arg Pro Ser Gln Val
```

```
                35                  40                  45
Leu Asn Lys Pro Arg Val Glu Ile Gly Gly Glu Asp Leu Arg Asn Phe
 50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Asn Phe Gly Asn Glu Ile Val Ser Tyr Glu Ser Pro Arg
                100                 105                 110

Pro Asn Ser Gly Ile His Arg Ile Val Leu Val Leu Phe Arg Gln Leu
                115                 120                 125

Gly Arg Gln Thr Val Tyr Glu Pro Gly Trp Arg Gln Gln Phe Asn Thr
                130                 135                 140

Arg Glu Phe Ala Ser Leu Tyr Asn Leu Gly Leu Pro Val Ala Ala Val
145                 150                 155                 160

Phe Tyr Asn Cys Gln Arg Glu Ser Gly Cys Gly Gly Arg Arg Ser
                165                 170                 175
```

<210> SEQ ID NO 90
<211> LENGTH: 175
<212> TYPE: PRT
<213> ORGANISM: Eutrema japonicum

<400> SEQUENCE: 90

```
Met Ser Ile Ser Pro Arg Asp Pro Leu Val Val Gly Arg Val Val Thr
 1               5                  10                  15

Asp Val Leu Glu Pro Phe Thr Arg Ser Ile Ser Leu Arg Val Thr Tyr
                20                  25                  30

Val Gln Arg Val Val Thr Asn Gly Leu Asp Leu Arg Pro Ser Gln Leu
                35                  40                  45

Leu Asn Lys Pro Arg Val Glu Ile Gly Gly Glu Asp Leu Arg Asn Phe
 50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Asn Phe Gly Asn Glu Ile Val Ser Tyr Glu Ser Pro Arg
                100                 105                 110

Pro Thr Ser Gly Ile His Arg Ile Val Leu Val Leu Phe Arg Gln Leu
                115                 120                 125

Gly Arg Gln Thr Val Tyr Glu Pro Gly Trp Arg Gln His Phe Asn Thr
                130                 135                 140

Arg Glu Phe Ala Ala Ile Tyr Asn Leu Gly Leu Pro Val Ala Ala Val
145                 150                 155                 160

Phe Phe Asn Cys Gln Arg Glu Ser Gly Cys Gly Gly Arg Arg Ser
                165                 170                 175
```

<210> SEQ ID NO 91
<211> LENGTH: 174
<212> TYPE: PRT
<213> ORGANISM: Eutrema salsugineum

<400> SEQUENCE: 91

```
Met Ser His Ala Arg Asp Pro Leu Val Val Gly Arg Val Val Pro Asp
 1               5                  10                  15

Val Leu Glu Leu Phe Thr Arg Ser Ile Ser Leu Arg Val Thr Tyr Gly
```

```
                    20                  25                  30
Gln Arg Glu Val Thr Asn Gly Leu Asp Leu Arg Pro Ser Gln Val Leu
         35                  40                  45

Asn Lys Pro Arg Val Asp Ile Gly Gly Glu Asp Leu Arg Asn Phe Tyr
 50                  55                  60

Thr Leu Val Met Val Asp Pro Asp Val Pro Ser Pro Ser Asn Pro His
 65                  70                  75                  80

Leu Arg Glu Tyr Leu His Trp Leu Val Thr Asp Ile Pro Ala Thr Thr
             85                  90                  95

Gly Thr Asn Phe Gly Asn Glu Ile Val Ser Tyr Glu Ser Pro Arg Pro
            100                 105                 110

Thr Ser Gly Ile His Arg Ile Val Leu Val Leu Phe Arg Gln Leu Gly
            115                 120                 125

Arg Gln Thr Val Tyr Glu Pro Gly Trp Arg Gln Asn Phe Asn Thr Arg
        130                 135                 140

Glu Phe Ala Ala Ile Tyr Asn Leu Gly Leu Pro Val Ala Ala Val Phe
145                 150                 155                 160

Phe Asn Cys Gln Arg Glu Ser Gly Cys Gly Gly Arg Arg Ser
                165                 170
```

<210> SEQ ID NO 92
<211> LENGTH: 20
<212> TYPE: DNA
<213> ORGANISM: Artificial sequence
<220> FEATURE:
<223> OTHER INFORMATION: Primer

<400> SEQUENCE: 92
ccatgatccg aagagactat                                                 20

<210> SEQ ID NO 93
<211> LENGTH: 20
<212> TYPE: DNA
<213> ORGANISM: Artificial sequence
<220> FEATURE:
<223> OTHER INFORMATION: Primer

<400> SEQUENCE: 93
atgttgagta ctgcctttag                                                 20

<210> SEQ ID NO 94
<211> LENGTH: 21
<212> TYPE: DNA
<213> ORGANISM: Artificial sequence
<220> FEATURE:
<223> OTHER INFORMATION: Primer

<400> SEQUENCE: 94
atggagaagc ttacactgat c                                               21

<210> SEQ ID NO 95
<211> LENGTH: 21
<212> TYPE: DNA
<213> ORGANISM: Artificial sequence
<220> FEATURE:
<223> OTHER INFORMATION: Primer

<400> SEQUENCE: 95
tggatttctt cctctcttca c                                               21

<210> SEQ ID NO 96

```
<211> LENGTH: 23
<212> TYPE: DNA
<213> ORGANISM: Artificial sequence
<220> FEATURE:
<223> OTHER INFORMATION: Primer

<400> SEQUENCE: 96
acttactcgg tgcgtttctg ttg                                              23

<210> SEQ ID NO 97
<211> LENGTH: 24
<212> TYPE: DNA
<213> ORGANISM: Artificial sequence
<220> FEATURE:
<223> OTHER INFORMATION: Primer

<400> SEQUENCE: 97
atacatcccc ctcgactcca atta                                             24
```

US 10,745,691 B2

POLYPEPTIDE FOR GENOME SHUFFLING IN PLANTS, AND USE THEREFOR

TECHNICAL FIELD

The present Description relates to a polypeptide for genome shuffling in plants, and to a use therefor.

DESCRIPTION OF RELATED ART

Increasing plant biomass is considered effective not only for increasing food production, but also for conserving the global environment, preventing global warming and reducing production of greenhouse gasses. Consequently, techniques for increasing production of plant biomass are of great industrial importance.

Properties associated with improving productivity and stress resistance in plants are quantitative traits that are influenced by expression of multiple genes rather than a single gene. Conventionally, modification of traits that are influenced by multiple genes has been accomplished by repeated mutagenesis over many generations. However, it is difficult to modify multiple traits simultaneously because the changes obtained by a single mutation are small when base substitution or deletion is induced by ordinary means. Moreover, multiple unnecessary mutations are known to accumulate at the same time as the useful mutations, and necessary traits are often lost in the process. There is therefore demand for the development of methods that can efficiently achieve massive reorganization among genomes in order to modify traits that are controlled by multiple genes. In plant and fungal cells, in fact, methods have already been reported for artificially inducing genetic recombination of genome DNA and obtaining various mutations by causing restriction enzymes to be expressed in living organisms (Japanese Patent No. 4158920, Japanese Patent Application Laid-open No. 2011-160798, Japanese Patent Application Laid-open No. 2012-44883). With these techniques, it is possible to efficiently obtain mutations through genome DNA reorganization by artificially inducing so-called genome shuffling in plant cells and fungal cells.

The florigen protein is known as a protein that is associated with plant flowering. Functional analysis of the florigen protein has been done using a fused protein comprising the florigen protein with a GFP protein or T7 tag, but no other reports are known (Notaguchi, M. et al., Plant Cell Physiol., 49, 1645-165J. C.; Corbesier, L. et al., Science, 316, 1030-1033J. C.; Tamaki, S. et al., Science, 316, 1033-1036).

CITATION LIST

Patent Literature

PTL 1 Japanese Patent No. 4158920
PTL 2 Japanese Patent Application publication No. 2011-160798
PTL 3 Japanese Patent Application publication No. 2012-44883

Non-Patent Literature

NPTL 1 Notaguchi, M. et al., Plant Cell Physiol., 49, 1645-165J. C.
NPTL 2 Corbesier, L. et al., Science, 316, 1030-1033J. C.
NPTL3 Tamaki, S. et al., Science, 316, 1033-1036.

BRIEF SUMMARY

In the techniques disclosed in the patent documents above, a frequent restriction enzyme gene such as the TaqI gene is introduced into plant cells and transiently activated so that it acts on the genome. Fundamentally, however, causing a restriction enzyme to act in vivo not only induces DNA mutation by genome shuffling, but also threatens cell survival at the same time. Consequently, there is a need to reduce the effects of restriction enzymes on cell survival in vivo.

The present Description provides a genome shuffling technique suited to creating a useful next generation plant.

(1) A polypeptide comprising a first polypeptide region for double-stranded DNA breakage activity, and a second polypeptide region for intertissue migration activity.

(2) The polypeptide according to (1), wherein the destination of the intertissue migration activity is a reproductive tissue or organ or a precursor tissue or organ thereof.

(3) The polypeptide according to (2), wherein the second polypeptide region has a polypeptide for the intertissue migration activity of a florigen protein.

(4) The polypeptide according to (3), wherein the florigen protein is derived from a plant in the Brassicaceae family.

(5) The polypeptide according to (4), wherein the plant in the Brassicaceae family is *Arabidopsis thaliana*.

(6) The polypeptide according to any of (1) to (5), wherein the first polypeptide region has frequent restriction enzyme activity.

(7) A genome shuffling agent containing the polypeptide according to any of (1) to (6).

(8) A polynucleotide coding for the polypeptide according to any of (1) to (6).

(9) A genome shuffling agent containing the polynucleotide according to (8).

(10) An expression vector comprising the polynucleotide according to (8).

(11) A plant body having the polypeptide according to any of (1) to (6) or a polynucleotide coding for that polypeptide.

(12) A method for genome shuffling in plants, comprising a step of introducing the polypeptide according to any of (1) to (6) into a plant body, and causing the intertissue migration activity and the double-stranded DNA breakage activity to act within the plant body.

BRIEF DESCRIPTION OF DRAWINGS

Figure 1B:
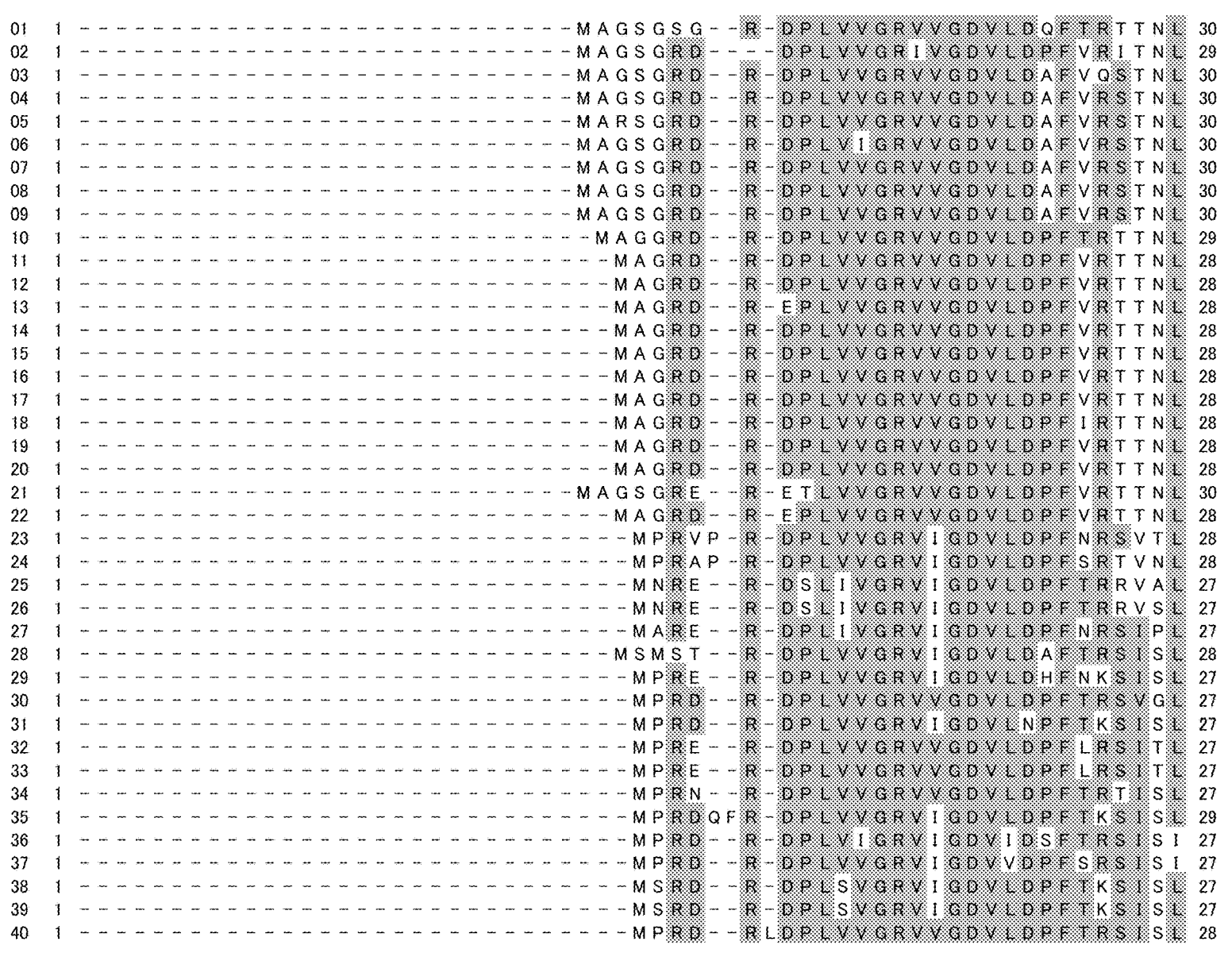
Figure 1C:
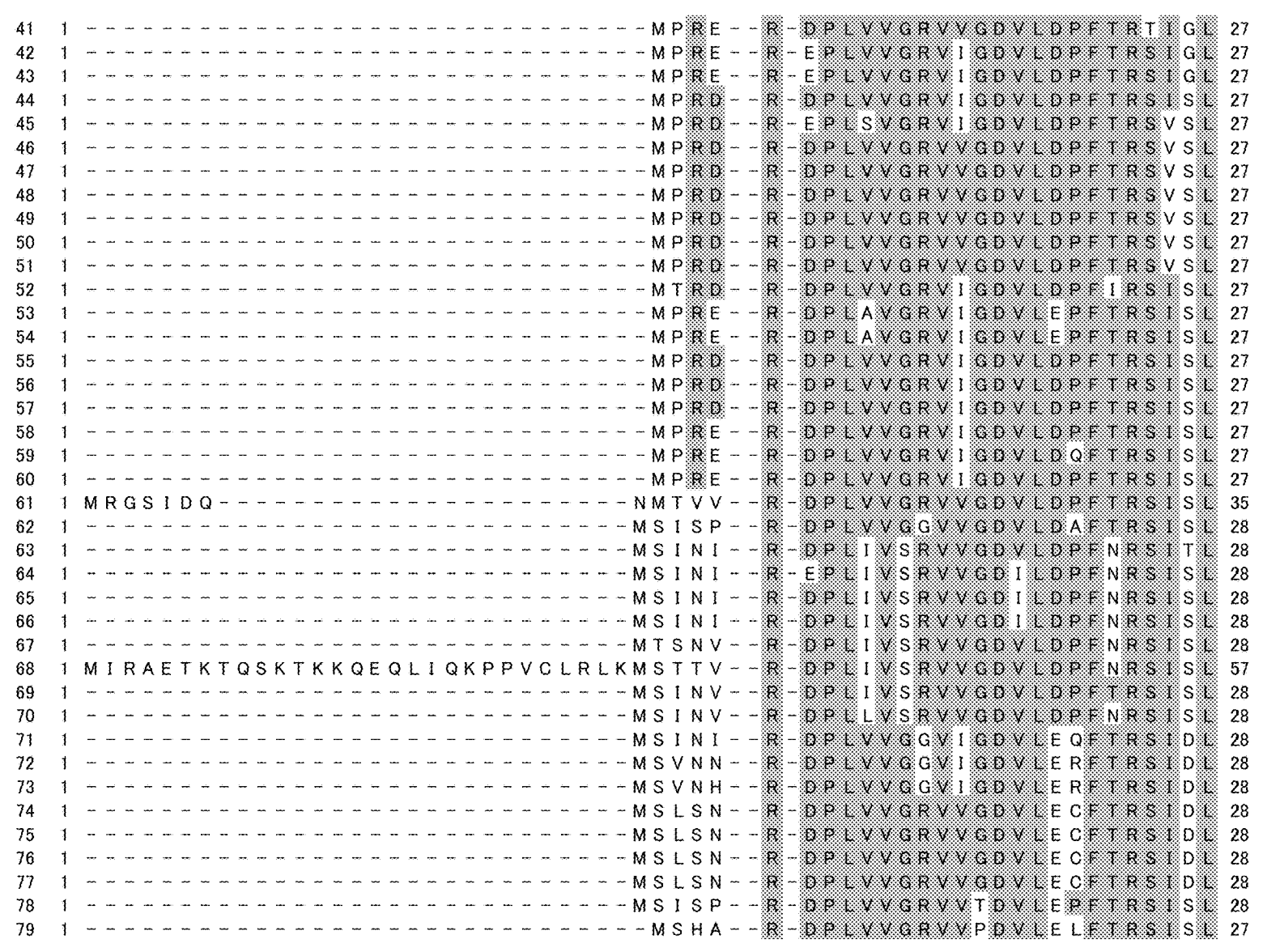
Figure 1E:
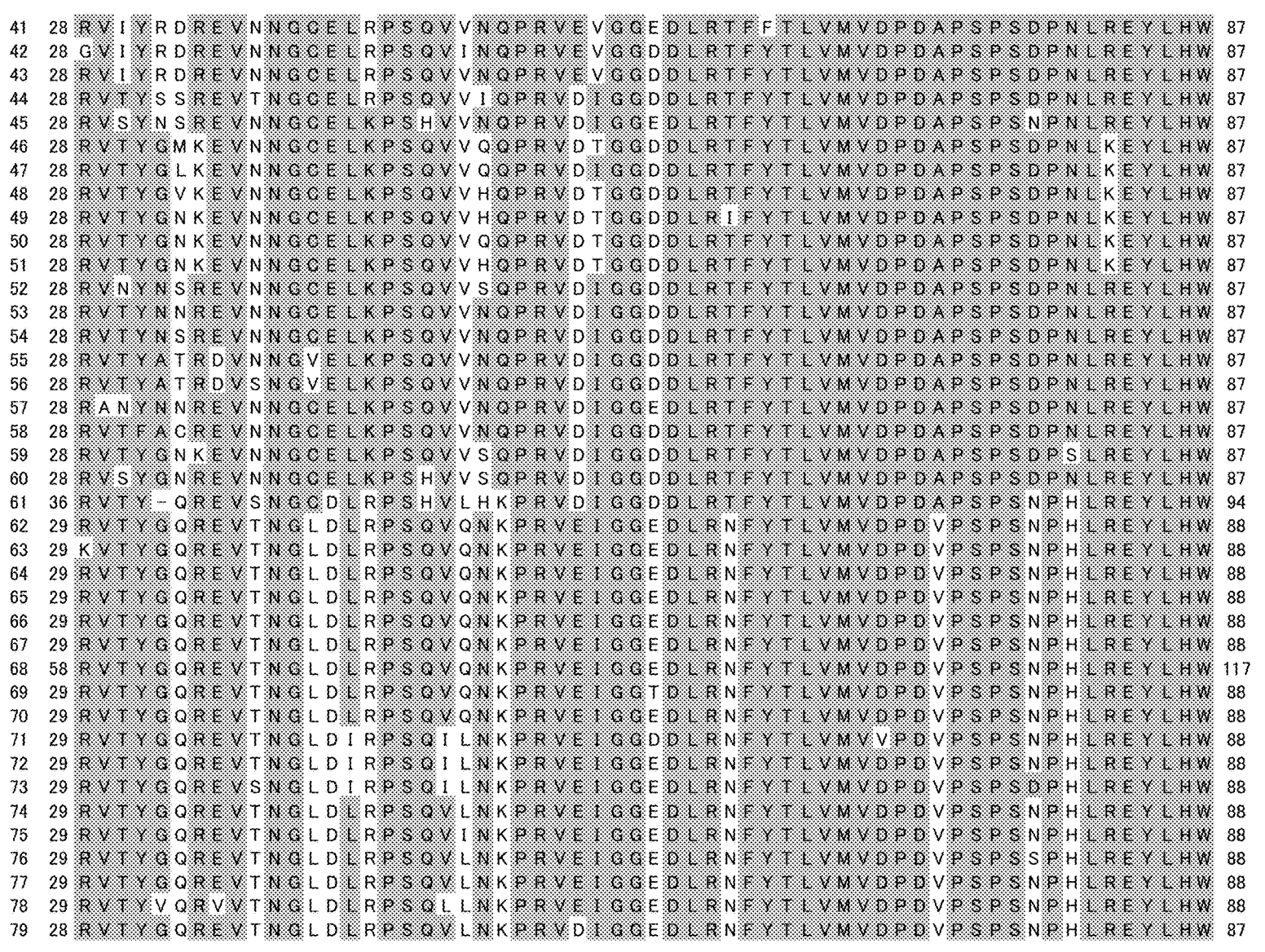
Figure 1F:
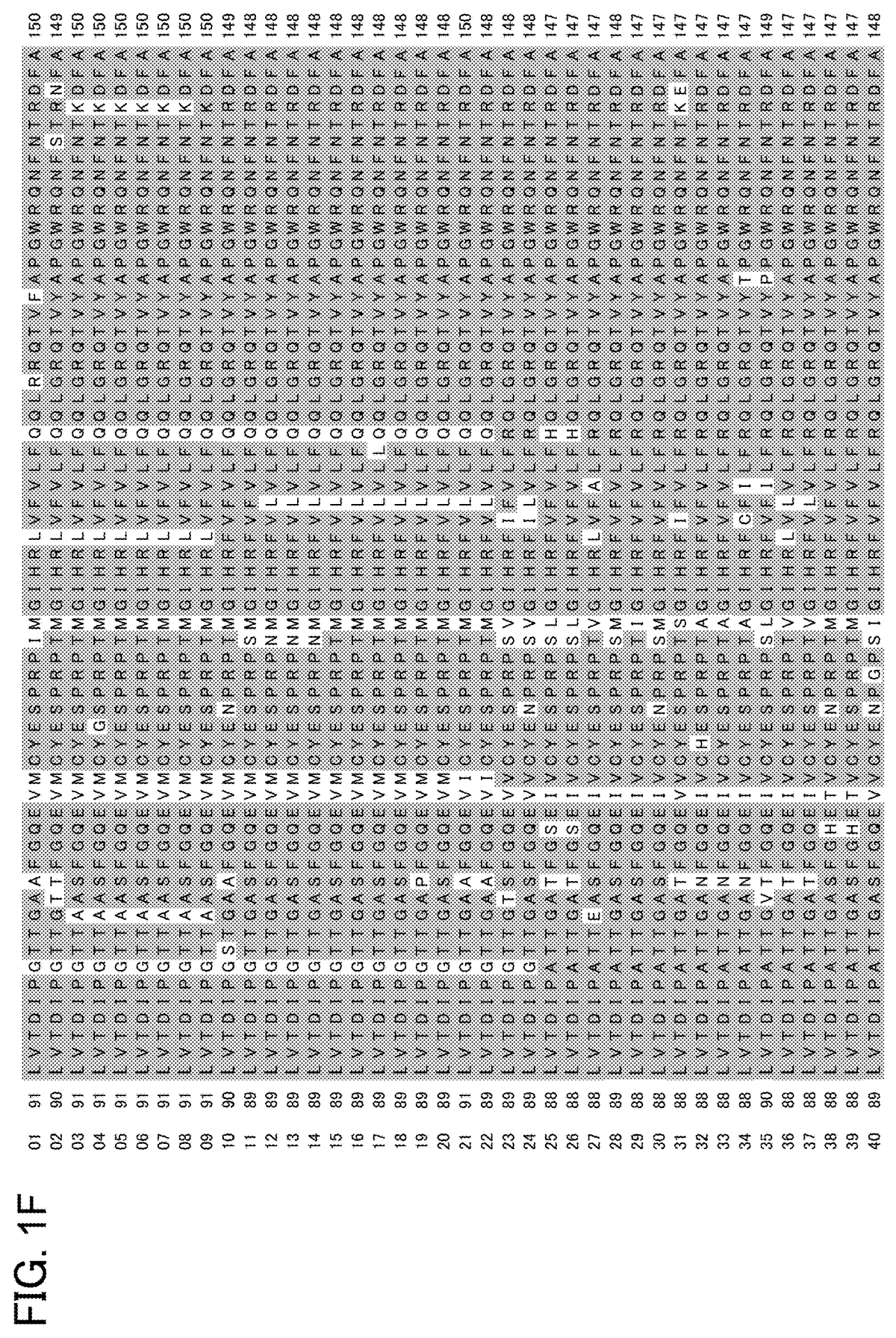
Figure 1G:
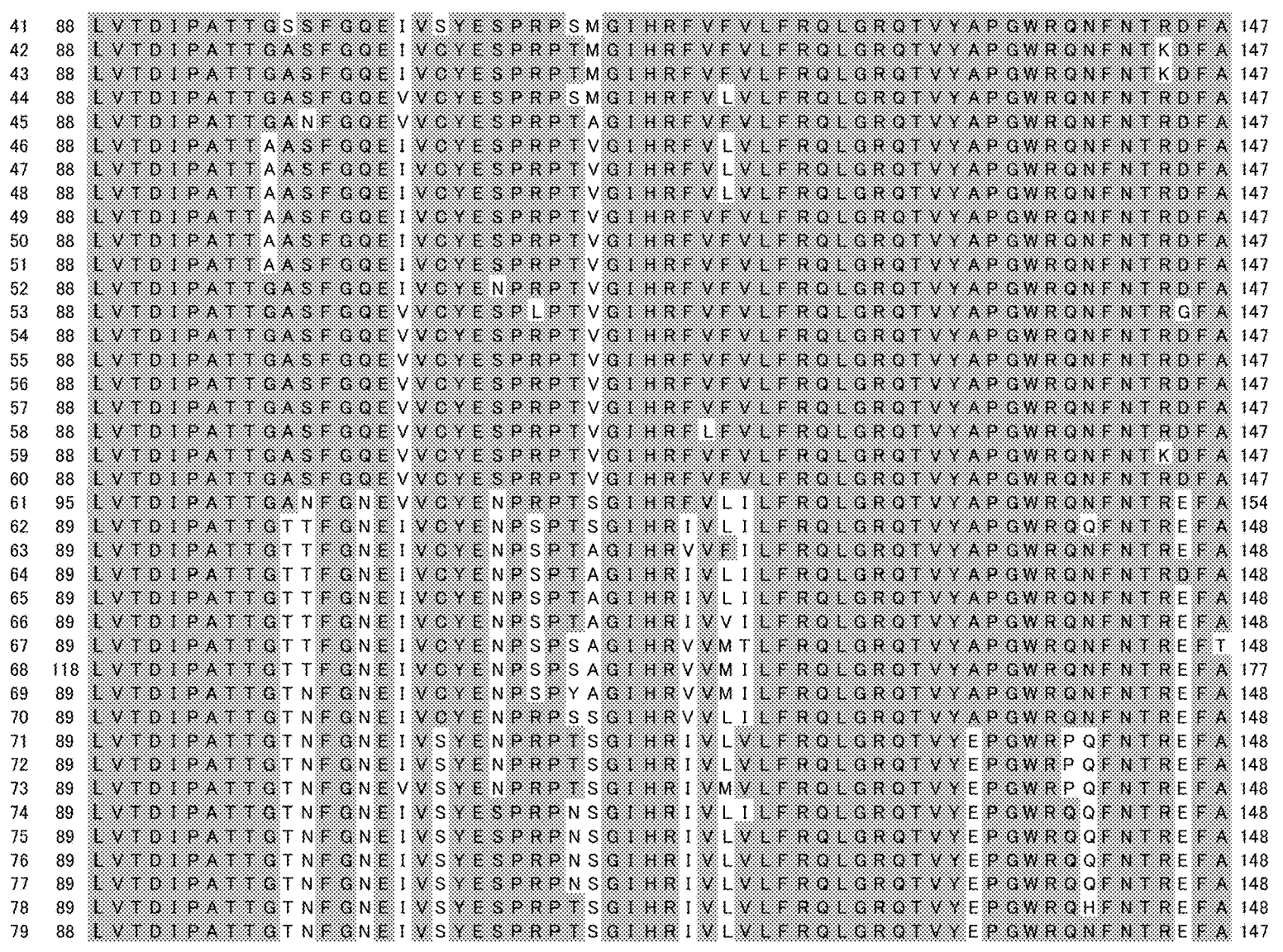
Figure 1I:
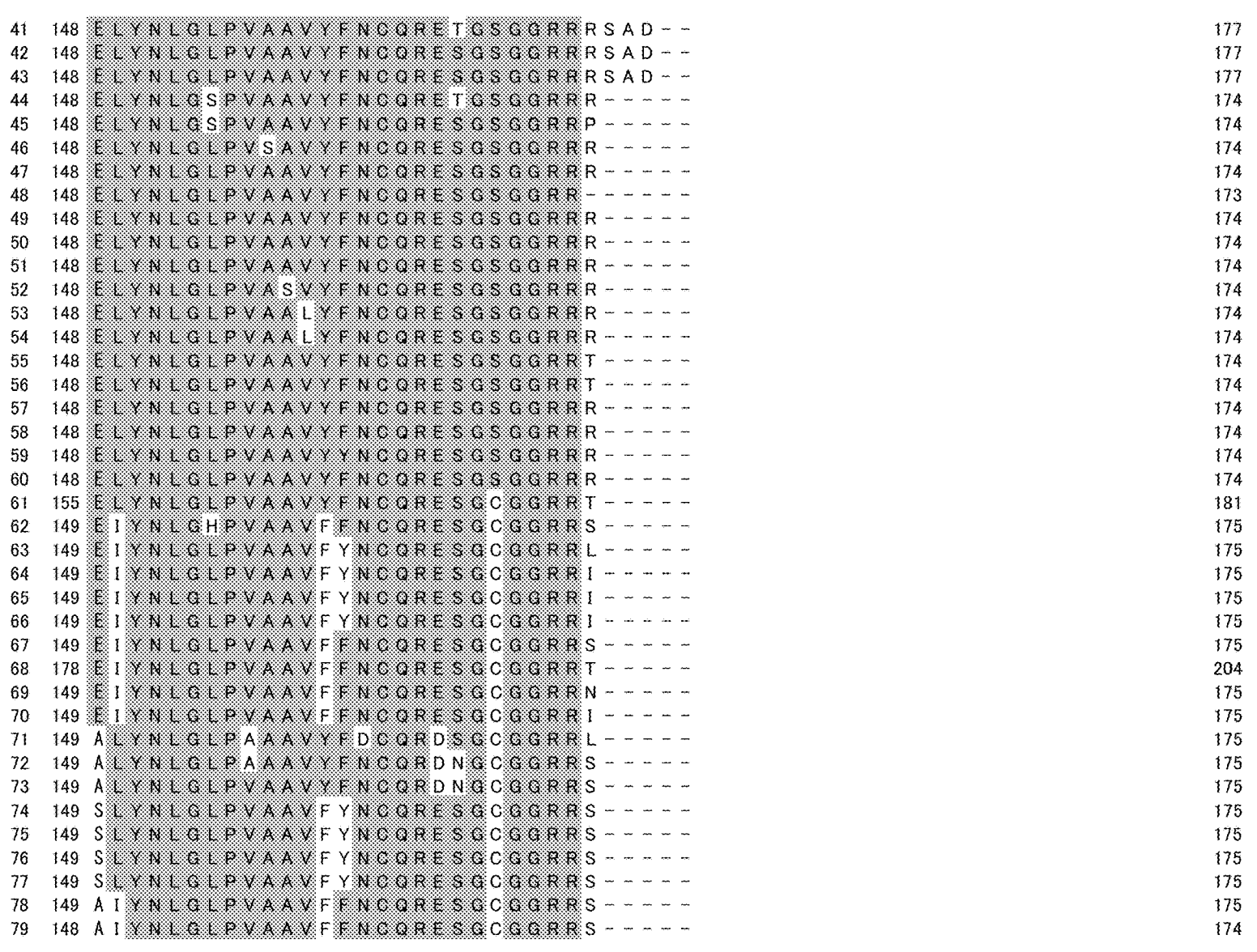

FIG. 1A is part of a chart showing the results of a homology analysis performed using the default MUSLE alignments settings of Genetyx Ver. 12.0.1 software on amino acid sequences obtained by BLAST as having high homology with the amino acid sequence of florigen proteins obtained based on the *Arabidopsis thaliana* FT protein and rice HD3a protein, the source plants and ID numbers of various amino acid sequences being shown in the chart;

FIGS. 1B-1I show the results of a homology analysis performed using the default MUSLE alignments settings of Genetyx Ver. 12.0.1 software on amino acid sequences obtained by BLAST as having high homology with the amino acid sequence of florigen proteins obtained based on the *Arabidopsis thaliana* FT protein and rice HD3a protein; in particular, FIGS. 1B, ID, 1F, and 1H show different parts of SEQ ID NOS: 13-52, and FIGS. 1C, 1E, 1G, and 1I show different parts of SEQ ID NOS: 53-91;

FIG. 2A shows BLAST analysis results for various amino acid sequences from FIGS. 1A to 1E (identity and similarity);

FIG. 2B shows another part of the BLAST analysis results of FIG. 2A;

FIG. 2C shows another part of the BLAST analysis results of FIG. 2A;

FIGS. 5A to 5C show tiling array analysis results for the nle mutant strain.

DETAILED DESCRIPTION OF INVENTION

Figure 3A:
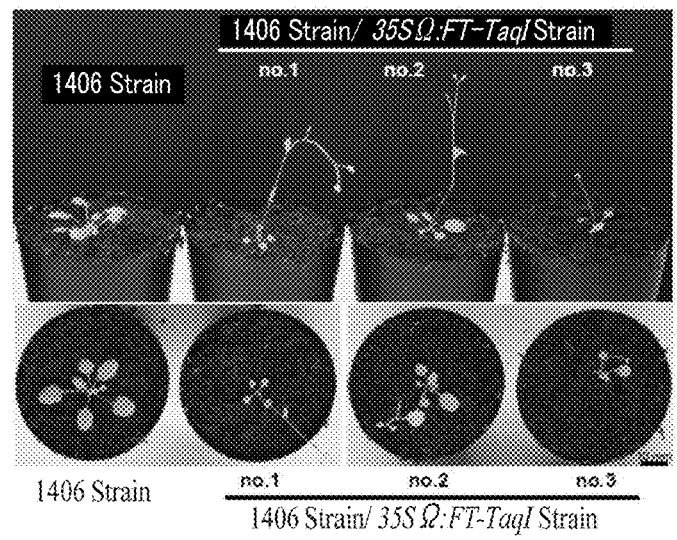
FIGS. 3A to 3C show the phenotypes of an (FIG. 3A) control strain (1406 strain) and a 1406 strain/pBI 35SΩ:FT-TaqI; the number of days required till flowering (FIG. 3B) and the number of rosette leaves at the time of flowering (FIG. 3C) were measured in order to measure the flowering times of the control strain (1406 strain) and 1406 strain/pBI 35SΩ:FT-TaqI; flowering was defined as the point at which the first flower stem reached 10 mm; all values are averages ±S.E; the different letters at the top of each bar graph indicate that significant differences were found by the Tukey-Kramer method after one-way analysis of variance (one-way ANOVA) ($p<0.01$)

The present Description relates to a technique for genome shuffling in plants. A polypeptide having intertissue migration activity and double-stranded DNA breakage activity (hereunder sometimes called "the polypeptide") can move through the tissue of a plant body based on its intertissue migration activity. Moreover, the polypeptide also has double-stranded DNA breakage activity, and can cause this double-stranded DNA breakage activity to act in tissue to which it has migrated. Consequently, with the polypeptide double-stranded DNA breakage activity can be made to act in a target tissue. By expressing such tissue-specific double-stranded DNA breakage activity, it is possible to reduce the effects on plant survival and longevity, and improve genome shuffling efficiency.

The polypeptide is suitable for transient application to plants. Harmful effects on plants can be reduced and genome shuffling efficiency improved by transient application. Moreover, by applying the polypeptide transiently to a plant it is possible to obtain a plant body that has undergone genome shuffling without having a gene such as a restriction enzyme gene introduced therein.

The polypeptide is suitable for application to tissue other than tissue for sexual reproduction or asexual reproduction. This is because as long as the intertissue migration activity of the polypeptide includes intertissue migration activity targeted at sexual or asexual reproductive tissue, the polypeptide itself does not need to be genetically expressed in reproductive tissue or directly introduced into reproductive tissue.

Various embodiments of the polypeptide and uses thereof are explained below. The plant body in the present Description is not particularly limited, but examples include dicotyledonous plants belonging to the Brassicaceae, Solanaceae, Leguminosae, Salicaceae and Myrtaceae, and some monocotyledonous plants belonging to the Gramineae and Palmaceae (see below).

Brassicaceae: *Arabidopsis thaliana, Brassica rapa, Brassica napus, Brassica oleracea* var. *capitata, Brassica rapa* var. *pekinensis, Brassica rapa* var. *chinensis, Brassica rapa* var. *rapa* L., *Brassica rapa* var. *hakabura, Brassica rapa* var. *lanciniifolia, Brassica rapa* var. *perviridis, Raphanus sativus, Wasabia japonica*, etc.

Solanaceae: *Nicotiana tabacum, Solanum melongena, Solaneum tuberosum, Lycopersicon lycopersicum, Capsicum annuum, Petunia*, etc.

Leguminosae: *Glycine max, Pisum sativum* L., *Vicia faba, Wisteria floribunda, Arachis hypogaea, Lotus corniculatus* var. *japonicus, Phaseolus vulgaris, Vigna angularis, Acacia*, etc.

Asteraceae: *Chrysanthemum morifolium, Helianthus annuus*, etc.

Palmaceae: *Elaeis guineensis, Elaeis oleifera, Cocos nucifera, Phoenix dactylifera, Copernicia*, etc.

Anacardiaceae: *Rhus succedanea, Anacardium occidentale, Toxicodendron vernicifluum, Mangifera indica, Pistacia vera*, etc.

Cucurbitaceae: *Cucurbita maxima, Cucurbita moschata, Cucurbita pepo, Cucumis sativus, Trichosanthes cucumeroides, Lagenaria siceraria* var. *gourda*, etc.

Rosaceae: *Amygdalus communis, Rosa, Fragaria, Prunus, Malus pumila* var. *domestica*, etc.

Caryophyllaceae: *Dianthus caryophyllus*, etc.

Salicaceae: *Populus trichocarpa, Populus nigra, Populus tremula*, etc.

Gramineae: *Zea mays, Oryza sativa, Hordeum vulgare, Triticum aestivum, Phyllostachys, Saccharum officinarum, Pennisetum purpureum, Erianthus ravennae, Miscanthus variegatum, Sorghum, Panicum*, etc.

Liliaceae: *Tulipa, Lilium*, etc.

Myrtaceae: *Eucalyptus camaldulensis, Eucalyptus grandis*, etc.

The plant body may be any that is derived from a plant, and may be in the form of a complete or almost complete plant body such as a seedling or the like provided with the organs or precursor organs of an individual plant such as a plant seedling, or plant cells or callus, or a part of an individual such as a seed, seedling, flower bud, leaf, stem, branch, root, meristem, lateral bud, flower bud, pollen, ovary, endosperm or embryo. It may also be in the form of a plant body for vegetative reproduction, such as a rootstock or scion for use in grafting, a cutting or leaf cutting for use in propagation by cutting, a stem for use in layering, or a rhizome, root, leaf, bulb, runner or propagule.

In the present Description, a "genome" may be chromosomal DNA in eukaryotic cells, or DNA existing as mitochondrial DNA or plastid DNA.

In the present Description, genome mutations encompass base substitutions, deletions, insertions, additions, translocations, inversions and creation of novel chromosomes in genome DNA, and epigenetic mutations caused by any of these.

Polypeptide

The polypeptide disclosed in the present Description may be provided with intertissue migration activity and double-stranded DNA breakage activity.

Double-stranded DNA Breakage Activity

The double-stranded DNA breakage activity of the polypeptide may be based on a polypeptide defining a double-stranded DNA breakage enzyme. That is, a polypeptide selected appropriately from polypeptides defining known double-stranded DNA breakage enzymes may be provided in part of the polypeptide as a first polypeptide region or in other words as a polypeptide region for double-stranded DNA breakage activity.

First Polypeptide Region: Polypeptide Region for Double-stranded DNA Breakage Activity A polypeptide of a double-stranded DNA breakage enzyme or a partial polypeptide that confers such activity may be applied as the first polypeptide region. A known so-called restriction enzyme may be used as such as double-stranded DNA breakage enzyme. The restriction enzyme may be selected after considering its recognition site, optimum temperature, number of amino acid residues and the like.

The cleavage site (recognition site) of the restriction enzyme applied to the first polypeptide region is not particularly limited. From the standpoint of genetic recombination efficiency, a double-stranded DNA breakage enzyme called a "frequent restriction enzyme" having a roughly 4-base to 6-base recognition site on the DNA double strand may be used for example.

For example a restriction enzyme having a 4-base or 5-base recognition site may be used. A restriction enzyme having a 4-base recognition site may also be used for example.

From the standpoint of the recognition site, examples are not particularly limited but include ApeKI, BsrI, BssKI, BstNI, BstUI, BtsCI, FatI, FauI, HinP1I, PhoI, PspGI, SmlI, TaqI, TfiI, TseI, Tsp45I and TspRI. Other examples include various known frequent restriction enzymes such as Sse9I, MseI, DpnI and CviAII.

There are no particular limitations on the optimal temperature of the restriction enzyme applied to the first polypeptide region. For example, a restriction enzyme from a thermophile may be used. A thermophile is a bacterium having an optimum growth temperature of at least 45° C. or a growth limit temperature of at least 55° C. Thermophiles are generally archaebacteria. Restriction enzymes from thermophiles may generally have deactivation temperatures of 80° C. or more. Moreover, restriction enzymes from thermophiles have optimum temperatures of roughly at least 50° C. and not more than 80° C.

A restriction enzyme from a thermophile has an optimum temperature for double-stranded DNA breakage activity, or in other words a temperature at which double-stranded DNA breakage enzyme activity is generally the highest (also called an incubation temperature), at a temperature range higher than the normal growth temperature of plants. Using such a restriction enzyme, the double-stranded DNA breakage activity of the polypeptide can be activated or increased or the activity can be reduced or the like at any timing and intensity by applying temperature treatment, this is convenient for causing the double-stranded DNA breakage activity of the polypeptide to act transiently. Moreover, by applying such a restriction enzyme its activity can be regulated by temperature. Furthermore, relatively gentle double-stranded DNA breakage activity can be obtained by using the restriction enzyme at a temperature lower than the optimum temperature.

A restriction enzyme with an optimum temperature of at least 50° C. and not more than 80° C. for double-stranded DNA breakage activity can be used as such a restriction enzyme. For example, the optimum temperature may be 50° C., 55° C., 60° C., 65° C. or 75° C. (catalog values in all cases). The optimum temperature of the restriction enzyme may be selected based on the catalogs and the like of various sales companies (catalog values) or the like. If the optimum temperature is less than 50° C., the double-stranded DNA breakage activity may be too strong. If the optimum temperature exceeds 80° C., the double-stranded DNA breakage activity may be too weak. The optimum temperature may be at least 55° C. for example, or at least 60° C. for example, or at least 62° C., or about 65° C. Moreover, the optimum temperature may be not more than 75° C. for example, or not more than 70° C. for example, or not more than 68° C. for example.

For example, a restriction enzyme may be selected appropriately from the following known restriction enzymes and applied to the polypeptide.

TABLE 1

| Optimum temperature ° C. | Restriction enzyme |
|---|---|
| 50 | APoI |
|  | BclI |
|  | BfuAI |
|  | BspQI |
|  | BssHII |
|  | BtsCI |
|  | Nt.BspQI |
|  | SfiI |
| 55 | BsiWI |
|  | BslI |
|  | BsmAI |
|  | BsmBI |
|  | BtsI |
|  | FatI |
|  | FauI |
|  | Nt.BstNBI |
|  | SmlI |
|  | Sse9I |
| 60 | BsaBI |
|  | BsaJI |
|  | BsaWI |
|  | BsiEI |
|  | BssKI |
|  | BstAPI |
|  | BstEII |
|  | BstNI |
|  | BstUI |
|  | BstYI |
|  | BtgZI |
|  | MwoI |
|  | AccIII(BspM) |
| 65 | BsiHKAI |
|  | BsmFI |
|  | BsmI |
|  | BsrDI |
|  | BsrI |
|  | BstBI |
|  | Nb.BsmI |
|  | Nb.BsrDI |
|  | PI-PspI |
|  | TaqI |
|  | TfiI |
|  | TseI |
|  | Tsp45I |
|  | Tsp509I |
|  | TspRI |
|  | Tth111I |
| 75 | ApeKI |
|  | PhoI |
|  | PspGI |
|  | TspMI |

Of those listed above, ApeKI, BsaBI, BsaJI, BsaWI, BsIEI, BslI, BsmBI, BsmI, BspQI, BsrDI, BsrI, BssKI, BstAPI, BstBI, BstNI, BstUI, BstYI, FatI, FauI, MwoI, Nb.BsmI, Nb.BsrDI, PspGI, SfiI, SmlI, TaqI, TfiI, TliI, TseI, Tsp45I, Tsp509I, TspMI, TspRI and Tth111I for example may be used from the standpoint of optimum temperature.

A restriction enzyme with an optimum temperature for double-stranded DNA breakage activity below 50° C. may also be used as the restriction enzyme. Moreover, a restriction enzyme with this optimum temperature below 45° C. may also be used.

An enzyme having an optimum temperature for double-stranded DNA breakage activity within the normal temperature range (cold restriction enzyme) may also be used as the restriction enzyme. The "normal temperature range" here means at least 15° C. and not more than 42° C. for example, or at least 15° C. and not more than 40° C. for example, or at least 25° C. and not more than 40° C. for example, or at least 25° C. and not more than 37° C. for example, or at least 30° C. and not more than 37° C. for example.

A cold restriction enzyme has an optimum temperature of roughly at least 25° C. and not more than 40° C. (typically, 25° C. or 37° C.). Moreover, a cold restriction enzyme can generally be deactivated by being incubated for 15 to 20 minutes at 60° C. to 80° C. The temperature at which enzyme activity is deactivated by 15 to 20 minutes of incubation is called the deactivation temperature. However, some cold restriction enzymes may have deactivation temperatures of at least 80° C.

With a cold restriction enzyme, DNA can be efficiently cleaved within cells while the adverse effects of the enzyme action conditions (especially temperature and the like) on the plant body can be avoided by adjusting the action conditions such as the amount (expressed amount) of the restriction enzyme and the timing, temperature and period of the enzyme action.

Moreover, because a cold restriction enzyme has some degree of double-stranded DNA breakage activity within the temperature range of the temperatures (growth temperatures) normally applied to the plant body, the intensity (level) of the enzyme action can be set with a high degree of freedom by adjusting the various action conditions.

A commercially available restriction enzyme with an optimum temperature of at least 25° C. and not more than 40° C. (typically 25° C. or 37° C.) may be used as the cold restriction enzyme. For example, a commercially available restriction enzyme with such an optimum temperature and a deactivation temperature of at least 60° C. and not more than 80° C. may be used.

A known restriction enzyme from a known non-thermophile may also be selected and used appropriately as a restriction enzyme from a non-thermophile.

Examples of such restriction enzymes are not particularly limited, but include AluI, HhaI, HinP1, MseI, MboI and HaeIII. The optimum temperatures of all of these are given as 37° C. Other examples include BfaI, BfuI, Bsh1236I, BsuRI, DpnI, DpnII, FspBI, HaeIII, Hin1II, Hin6I, HpaII, HpyCH41V, MspI, NlaIII, RsaI and Sau3AI. The restriction enzymes listed above all have optimum temperatures of about 37° C. Other examples include ApaI, BaeI, BspCNI, CviAII, CviQI, SmaI and SwaI. These restriction enzymes all have optimum temperatures of about 25° C.

The optimum temperatures for the activities of proteins such as restriction enzymes having double-stranded DNA breakage activity are described in the protocols obtained with the enzymes, and can also be based on the results of an enzyme reaction evaluation performed at various temperatures in the presence of a specific concentration of a specific substrate in buffer that is considered suitable for the enzyme.

For example, methods for measuring the optimum temperature of restriction enzymes are described in the document (Greene, P. J., Poonian, M. S., Nussbaum, A. L., Tobias, L., Garfin, D. E., Boyer, H. W. & Goodman, H. M. (1975), Restriction and modification of a self-complementary octanucleotide containing the Eco RI substrate. Journal of Molecular Biology, 99(2), 237-261). Specifically, cleavage of SV40 DNA ($^{37}$P labeled) by a restriction enzyme is quantitatively analyzed. That is, 5 µl of a restriction enzyme solution (0.05 M potassium phosphate buffer (pH 7.0), 0.02 M NaCl, 0.02% NP40, 0.1 mM EDTA, 0.7 mM f-mercaptoethanol, 0.7 µM restriction enzyme) is added to a total of 50 µl of a reaction solution (0.1 M Tris HCl (pH 7.5), 5 mM $MgCl_2$, 0.05 mM MgCl2, 0.05 M NaCl 1.6 µM SV40 DNA), and restriction enzyme treatment is performed for a suitable time of about several minutes at various temperatures (temperatures set at suitable temperature intervals between about 0° C. and 80° C.). 1% SDS is added to stop the reaction, and supercoil DNA (form I), open circle DNA (form II) and linear DNA (form III) are isolated by agarose electrophoresis. The radiation dose (cpm) of each form is measured, and the number of phosphodiester bonds (pmol) cleaved by restriction enzyme treatment is determined by the following formula. The phosphodiester bonds cleaved at each temperature can then be graphed, and a temperature near the peak value can be taken as the optimum temperature (for double-stranded DNA breakage activity) of the enzyme.

Phosphodiester bonds(pmol)=[2×(dose of form III (cpm)+dose of form II (cpm))/(total dose of forms I,II and III(cpm))]×amount of DNA(pmol)

The deactivation temperature of a protein such as a restriction enzyme having double-stranded DNA breakage activity can be determined for example by maintaining the enzyme at each temperature for about 15 to 20 minutes and measuring the activity before and after heat treatment. The temperature at which activity is no longer detected is the deactivation temperature.

To obtain double-stranded DNA breakage activity and intertissue migration activity with the polypeptide, it may be useful to appropriately adjust the size of the first polypeptide region. For example, according to Corbesier et al. (Science, 316, 1030-1033J. C.), Tamaki et al. (Science, 316, 1033-1036) and Mathieu et al. (Curr. Biol., 17, 1055-1060), it appears that when intertissue migration activity is based on the florigen protein FT, the associated protein is preferably no larger than 92 kDa. From this perspective, the restriction enzyme applied to the first polypeptide region is preferably no larger than 92 kDa. It may also be no larger than 80 kDa for example, or 70 kDa for example, or 60 kDa for example, or 55 kDa for example, or 50 kDa for example, or 45 kDa for example, or 40 kDa for example, or no larger than 35 kDa for example. From this perspective, examples of the restriction enzyme include TaqI (31.5 kDa, 263 amino acids), HinP1I (28.6 kDa, 247 amino acids) and MseI (20.7 kDa, 186 amino acids).

Intertissue Migration Activity The polypeptide has intertissue migration activity. Intertissue migration activity may be based on a polypeptide defining a protein having intertissue migration activity. Intertissue migration activity here means the activity of moving from one tissue of a plant body to another tissue other than that tissue. Seen from the tissue of origin, the other tissue (destination tissue) is a tissue or organ belonging to a different classification in the plant body. The origin tissue and destination tissue are not particularly limited, but for example the destination tissue or in other words the target tissue may be a reproductive tissue or organ or a precursor tissue or organ thereof. By targeting this tissue or organ, it is possible to selectively perform genome shuffling on a genome that will be transmitted to the next generation. Meanwhile, genome shuffling is suppressed and the effects on plant growth and survival are reduced in other tissues of the plant body.

Second Polypeptide Region: Polypeptide Region for Intertissue Migration Activity A polypeptide having intertissue migration activity or a partial polypeptide that contributes to that activity may be applied as the second polypeptide region. That is, a polypeptide having an intertissue migration activity suited to the objective may be selected from known intertissue migration activity polypeptides as a polypeptide having such intertissue migration activity.

An example of a protein having intertissue migration activity in plant bodies is a florigen protein.

Florigen protein are proteins that are widely distributed in plants (Wigge, P. A. (2011), FT, A Mobile Developmental Signal in Plants. Curr. Biol., 21, R374-R378). Florigen proteins are proteins that have the activity of moving between tissues in the direction of reproductive tissues or organs or reproductive precursor tissues or organs, and are also known as flowering hormones that induce flower bud differentiation in plant bodies (Wigge, P. A. et al. above). Flowering begins when a florigen protein that has been synthesized in leaves moves through the sieve tissue to the meristems, where it induces flower bud differentiation (Wigge, P. A. et al. above). A florigen protein may also have a function other than flower formation (flowering), such as asexual reproduction by induction of rhizome formation. For example, when the rice florigen protein (Hd3a) is overexpressed in potatoes it is known to induce tuber formation (Navarro et al., (2011), Control of flowering and storage organ formation in potato by Flowering Locus T., Nature., 478, 119-122). This points to the ability of florigen proteins to migrate to rhizomes.

An FT protein (Accession No. NP_176726.1) (SEQ ID NO:1) coded for by the Flowering Locus T gene (FT gene) (SEQ ID NO:2) in *Arabidopsis thaliana* in the Brassicaceae and an Hd3a protein (Accession No. BAO03005.1) (SEQ ID NO:3) coded for by the Hd3 gene (SEQ ID NO:4), a homolog of FT in rice, have been identified as florigen proteins. Based on the amino acid sequences of the FT protein and Hd3a protein, a person skilled in the art can use a known database such as BLAST to search for proteins having the same intertissue migration activity as these, and select them appropriately by evaluating the intertissue migration activity or the like.

The intertissue migration activity of such a protein can be evaluated easily by observing migration within the plant body using a fluorescent protein such as GFP as a label.

FIGS. 1A to 1I show the results of a homology analysis performed using the default MUSLE alignments settings of Genetyx Ver. 12.0.1 software on amino acid sequences obtained by BLAST as having high homology with the amino acid sequences of florigen proteins obtained based on the *Arabidopsis thaliana* FT protein and rice HD3a protein. FIG. 2 shows BLAST results for these amino acid sequences.

As shown in FIGS. 1A to 1I and FIG. 2A to 2C, the amino acid sequences of the extracted proteins have high amino acid sequence homology (identity and similarity) to the FT protein (amino acid sequence specified by No. 63 in FIG. 2B to 2C) and the Hd3a protein (amino acid sequence specified by No. 9 in FIG. 2A). For example, the proteins defined by the amino acid sequences shown in FIGS. 1A to 1I are all presumed to funct as florigen proteins. A person skilled in the art can select these proteins appropriately and use them as the protein.

In FIGS. 1B to 1I, amino acid residues that are identical to one another are shown in gray. Based on alignment, the following highly similar first to fifth motifs can be extracted based on the FT protein.

First Motif
Position 7 to position 20 (14AA) of SEQ ID NO:1
*Arabidopsis thaliana* (No. 63 (SEQ ID NO:1), here and below): D, P, L, I, V, S, R, V, V, G, D, V, L, D
Overall variations: D/E, P/T/S, L, I/V/S/A/L, V/I, S/G, R/G, V/I, V/I, G/T/P, D, V/I, L/I/V, D/E/N Second Motif
Position 39 to position 46 (8AA) of SEQ ID NO: 1
*Arabidopsis thaliana*: NGLDLRPS
Overall variations: N, G/S, L/S/V, D/E, L/F/I, R/K, P/H, S Third Motif
Position 51 to position 88 (38AA) of SEQ ID NO:1
*Arabidopsis thaliana*: KPRVEIGGEDLRNFYTLVMVD-PDVPSPSNPHLREYLHW
Overall variations: K/Q/H, P, R, V/I, E/D/V, I/V, G, G, E/D/N/T/P, D/E, L/M, R, N/T/S/I, F, Y/F, T, L, V, M, V/A, D/V, P, D, V/A, P, S, P, S, N/D/E/S, P, H/N/S/R/T, L, R/K/T, E, Y, L, H, W Fourth Motif
Position 89 to position 148 (60AA) of SEQ ID NO: 1
*Arabidopsis thaliana*:

LVTDIPATTGTTFGNEIVCYENPSPTAGIHRVVFILFRQLGRQTVYAP
GWRQNFNTREFA

Overall variations: L, V, T, D, I, P, A/G, T/S, T, G/A/E, T/A/S/V/T, T/N/S/A/P, F, G, N/Q/H/S, E, I/V, V/M/I, C/S, Y/H, E/G, N/S, P, S/R/L/G, P, T/S/Y/N//I, A/S/V/M/I/L, G, I, H, R, V/F/L/I, V/I/C/L, F/L/M, I/V/A, L, F/L, R/Q/H, Q, L, G/R, R, Q, T, V, Y/F, A/E/T/P, PGWR, Q/P, N/Q/H, F, N/S, T, R/K, E/D/G/N, F, A/T Fifth Motif
Position 149 to position 174 (26AA) of SEQ ID NO: 1
*Arabidopsis thaliana*: EIYNLGLPVAAVFYNCQRES-GCGGRR
Overall variations: E/S/A, I/L/V, Y, N, L/I, G, L/S/P/Q/H, P/A, V/I, A/S, A/S/T, V/L/A, F/Y, Y/F/C, N/D, C, Q, R, E/D, S/A/T/G/N/R, G, C/S/T, G, G, R, R A protein having at least the third to fifth motifs and also having the first and/or second motif out of the first to fifth motifs is preferred as the florigen protein. This protein may also have at least 75%, or preferably at least 80%, or more preferably at least 85%, or still more preferably at least 90%, or yet more preferably at least 95%, or most preferably at least 97%, or especially at least 98%, or more especially at least 99% identity overall with the amino acid sequence of the *Arabidopsis thaliana* florigen protein represented by SEQ ID NO:69, the amino acid sequence of the rice Hd3a protein, or any amino acid sequence shown in FIGS. 1A to 1I. Alternatively, it may have at least 85%, or preferably at least 90%, or more preferably at least 95%, or still more preferably at least 97%, or yet more preferably at least 98%, or most preferably at least 99% similarity.

These florigen proteins may also have at least 75% identity, or may have at least 80% identity with the amino acid sequence of the FT protein (SEQ ID NO: 1) or the amino acid sequence of the Hd3a protein (SEQ ID NO:3). For example, the degree of identity may be at least 85%, or at least 90%, or at least 91%, or at least 92%, or at least 93%, or at least 94%, or at least 95%, or at least 96%, or at least 97%, or at least 98%, or at least 99%. The amino acid sequence similarity may be at least 85%, or at least 90%, or at least 95% for example.

In the present Description, the identity or similarity of a nucleotide sequence or amino acid sequence is a relationship between two or more polynucleotides or two or more proteins, which is a known matter to those skilled in the art and is determined by comparing the sequences. "Identity" in this context means the degree of sequence invariance between protein or polynucleotide sequences as determined by alignment of the protein or polynucleotide sequences or in some cases by alignment among a series of such sequences. Similarity means the degree of correspondence between protein or polynucleotide sequences as determined by alignment of the protein or polynucleotide sequences or in some cases by alignment among a series of partial sequences. More specifically, it is determined by the degree of sequence identity and conservation (substitution that conserves the physiochemical properties of a specific amino acid or sequence in a sequence). In the BLAST sequence homology test results given below, similarity is called "Similarity". The methods of determining identity and similarity are preferably designed so as to obtain the longest possible alignment between corresponding sequences. Methods of determining identity and similarity are provided as publicly available programs. For example, they can be determined using the basic local alignment search tool (BLAST) program of Altschul et al. (see for example Altschul, SF, Gish W, Miller W, Myers E W, Lipman D J., J. Mol. Biol., 215: pp 403-410 (1990) and Altschul S F, Madden T L, Schaffer A A, Zhang J, Miller W, Lipman D J., Nucleic Acids Res. 25: pp 3389-3402 (1997)). The conditions when using software such as BLAST are not particularly limited, but the default settings are preferred.

The polypeptide may be obtained artificially as a fused protein. For example, the polypeptide can be obtained by chemical or genetic engineering methods based on the amino acid sequences of the polypeptides applied to the first polypeptide region and second polypeptide region.

These polypeptides may be provided as part of the polypeptide, without any particular limitations. For example, the first polypeptide region may be provided at the N-end or C-end of the polypeptide, or in another location. Similarly, the second polypeptide region may be provided at the N-end or C-end of the polypeptide, or in another location. Moreover, the polypeptide may be provided with one or two or more kinds of the first polypeptide region, or with one or two or more kinds of the second polypeptide region. Furthermore, the polypeptide may also be provided with a suitable polypeptide region for intercellular migration in plants as appropriate.

Use

By causing the polypeptide to be present in a plant body, it can then be delivered to a specific target tissue based on its intertissue migration activity. Genome shuffling can then be produced in the target tissue based on the double-stranded DNA breakage activity of the polypeptide. That is, the polypeptide is useful as a genome shuffling agent.

When the target tissue of the intertissue migration activity of the polypeptide is a reproductive tissue or organ or a reproductive precursor tissue or organ, genome shuffling can be produced effectively in a genome that is passed down to the next generation by sexual reproduction.

When the target tissue of the intertissue migration activity of the polypeptide is a root, stem, leaf, bulb or other (storage) organ rather than a reproductive tissue or organ for example, genome shuffling can be produced in a genome that is passed down to the next generation by asexual reproduction (vegetative reproduction). Asexual reproduction here encompasses known asexual reproduction of plant bodies using grafts, cuttings, layering, runners, bulbs, rhizomes, root division, propagules, tissue cultures and the like. As discussed above, florigen proteins are applicable to asexual reproduction because they can target tissue such as rhizome tissue rather than reproductive tissue.

The tissue in which genome shuffling occurs can be deliberately selected with the polypeptide. Consequently, it is possible to reduce the effects on plant survival (especially effects stemming from double-stranded DNA breakage activity). With the polypeptide, mutations and modifications can be induced in the next generation genome when the target tissue of the polypeptide is a tissue associated with reproduction or breeding, and it is thus possible to obtain a plant or plant population with a modified phenotype. On the other hand, when the target tissue is only expressed transiently in the growth stages of the plant body or only in the late or final stages of growth, genome shuffling can be produced only in that tissue, which can then be harvested to obtain a plant cell, tissue or organ suited to obtaining a next-generation plant.

Furthermore, the following advantages can be obtained when sexual reproductive tissue or precursor tissue thereof is targeted using a florigen protein or a part thereof as the second polypeptide region.

(1) Early flowering can be induced and flower bud formation promoted by causing the polypeptide to act inside plant body. As a result, it is possible to greatly reduce the time required to prepare a population (library) of next-generation plants (seeds) having different genotypes and/or phenotypes as a result of genome shuffling.

(2) Expression of the polypeptide can be induced by genetic engineering either transiently or in tissue or organs other than sexual reproductive tissue or organs so that only the polypeptide moves to a target tissue such as sexual reproductive tissue. It is thus possible to prepare a next-generation seed that has an induced genome mutation or modification but does not carry an exogenous gene, thereby eliminating the time required to remove the exogenous gene and creating a plant body with stable traits.

Polynucleotide

The present Description provides a polynucleotide coding for the polypeptide (hereunder sometimes called "the polynucleotide"). The polynucleotide itself is useful as a genome shuffling agent. Examples of the polynucleotide include single-stranded DNA, double-stranded DNA, single-stranded RNA or DNA/RNA hybrids and DNA/RNA chimeras. Thus, it can be any capable of coding for the amino acid sequence of the polypeptide as information. The polynucleotide may be in the form of single-stranded or double-stranded DNA or single-stranded or double-stranded RNA for example.

The polynucleotide may take the form of a construct such as an expression vector comprising a coding region coding for the amino acid sequence of the polypeptide together with a control region for causing expression of the polypeptide as a protein (polypeptide).

Expression Vector

The present Description provides an expression vector comprising the polynucleotide (hereunder sometimes called "the expression vector"). The expression vector is designed to cause expression of information encoded by the polynucleotide (the amino acid sequence of the polypeptide). In addition to the polynucleotide, the expression vector may also comprise one or two or more control regions for causing expression of the polypeptide. Examples of these control regions include a promoter, terminator, selection marker, enhancer and base sequence for enhancing translation efficiency. The expression vector may also comprise a region coding for a nuclear localization signal.

The promoter is not particularly limited as long as it can cause expression of the polypeptide in a plant body, and a known promoter may be used appropriately. Examples of this promoter include the cauliflower mosaic virus 35S promoter (CaMV35S), various actin gene promoters, various ubiquitin gene promoters, and the nopaline synthase gene promoter, tobacco PR1a gene promoter, tomato ribulose 1,5-bisphosphate carboxylase-oxidase small subunit gene promoter and napin gene promoter.

As discussed below, a promoter such as a SIG2 promoter from an *Arabidopsis thaliana* sigma factor (AtSIG2) having a lower expression intensity than the 35S promoter is desirable in some cases as a low expression type constitutive promoter for causing constant expression of the polypeptide at a low level. Otherwise, the inducible promoters discussed below such as the *Arabidopsis thaliana* HSP18.2 promoter may also be useful as low expression type constitutive promoters for causing expression of the polypeptide because they can sometimes induce controlled expression of gene at a temperature lower than the induction temperature.

An inducible promoter may also be used as the promoter. With an inducible promoter, the polypeptide can be made to act through specific expression induction in a plant body. The action of the polypeptide can thus be expressed with deliberate timing. Such inducible promoters include inducible promoters that are induced by external conditions such as chemical substances and their concentrations, heat, osmotic pressure and the like as well as site-specific promoters and time-specific promoters. These various inducible promoters may be selected appropriately from known promoters such as DEX inducible promoters and the HSP18.2 promoter.

A site-specific promoter, time-specific promoter or the like may also be used as the promoter. The polypeptide can be expressed and its activity obtained with deliberate timing or in a target site by inducing expression of the polypeptide site-specifically or time-specifically. Induction can also be stopped, or the action of the polypeptide can be largely reduced or stopped by the passage of a specific period of time. When using an inducible promoter, temperature or a chemical substance or the like is supplied appropriately to the plant body according to the type of promoter.

The activity of the polypeptide is also affected when the expression intensity of the polypeptide is controlled with control elements such as promoters and terminators. Thus, the expression intensity of the polypeptide when obtained using such a promoter or terminator used is also taken into consideration when selecting the promoter and the like.

The terminator is not especially limited as long as it functions as a transcription termination site, and a known terminator may be used. Specifically, a nopaline synthase gene transcription termination region (Nos terminator), a cauliflower mosaic virus 35S transcription termination region (CaM V35S terminator) or the like can be used by preference. Of these, the Nos terminator is especially desirable.

In addition, known elements may be selected appropriately and used as selection markers and base sequences for enhancing translation efficiency. The method for constructing the expression vector is not particularly limited, and the necessary elements may be introduced into an appropriately selected host vector. The expression vector may also have a T-DNA region.

For example, various conventional known vectors for plants may be used as host vectors for the expression vector used to cause expression the protein in the cells of a plant body. Examples of virus vectors include plant virus vectors such as tobacco mosaic virus (TMV), plum pox virus (IPPV), potato virus X (PVX), alfalfa mosaic virus (AIMV), cucumber mosaic virus (CMV), cowpea mosaic virus (CPMV) and zucchini yellow mosaic virus (ZYMV). When the vector is introduced by a method using *Agrobacterium*, a pBI binary vector may be desirable in addition to the plant virus vectors listed above. Specific examples of pBI binary vectors include pBIG, pBIN19, pBI101, pBI121 and pBI1221. A vector of a known transient gene expression system may also be used.

A vector designed to cause expression of the polypeptide in a plant body can be constructed by a person skilled in the art by conventional known techniques suited to the type of plant body and the transformation methods. A vector suited to the target plant cells may be obtained appropriately, and a suitable promoter, terminator, enhancer and the like may be selected appropriately and used to construct the desired expression cassette as necessary.

In preparing the expression vector, a person skilled in the art may apply standard recombinant DNA techniques such as methods using restriction enzymes and DNA ligase (see for example Molecular Cloning, Third Edition, 1.84, Cold Spring Harbor Laboratory Press, New York) to various recombination operations depending on the type of plant body and the intended conditions for, for example, expressing the polypeptide.

Because the polynucleotide and expression vector code for the polypeptide, they are useful as genome shuffling agents in the same way as the polypeptide. The polynucleotide and expression vector may be introduced into a plant body by a known gene introduction method such as a gene introduction method using an appropriate *Agrobacterium* or virus, to obtain the function of the polypeptide by causing it to be synthesized.

Genome Shuffling Method

The genome shuffling method disclosed in the present Description (hereunder sometimes called "the shuffling method") may have a step of introducing the polypeptide into a plant body, and causing its intertissue migration activity and double-stranded DNA breakage activity to act in the plant body. With the shuffling method, double-stranded DNA breakage activity can be effected in a target tissue defined by the intertissue migration activity, and genome shuffling can be accomplished in the target tissue.

Several embodiments are possible for introducing the polypeptide into a plant body. In the first embodiment, the polynucleotide or expression vector coding for the polypeptide is introduced and made to be expressed in a plant body. In the second embodiment, the polypeptide is supplied directly to a plant body.

First Embodiment for Introducing Polypeptide of Invention

In the first embodiment, the polynucleotide (such as DNA) or the expression vector coding for the polypeptide is introduced into a plant body to thereby cause expression of the polypeptide. Various known methods may be adopted for introducing the expression vector or the like into a plant body in order to cause expression of the polypeptide in the plant body. For example, the expression vector may be introduced into the plant body by a known transfonrmation method in plants, such as the PEG method, electroporation method, particle gun method or plant virus method. Various *Agrobacterium* methods are also used, such as infecting cells or tissue with *Agrobacterium* or infecting flowers with *Agrobacterium* by the floral dip method or floral spray method.

The polypeptide may also be expressed transiently using an *Agrobacterium* or plant virus vector for a known transient gene expression system. The polynucleotide may also be incorporated into a chromosome.

When using an expression vector or the like, the plant body used for introduction may be a whole plant body, or may be selected appropriately from various cells, tissues, organs and the like including plant cells or callus, seedlings, leaves, flower buds, seeds, meristem, lateral buds, flower buds, pollen, ovaries, endosperm and embryos, according to the introduction method or the like.

*Agrobacterium* methods are also advantageous because the plant body can be efficiently regenerated by using the flower dip method or flower spray method.

When using the expression vector, the optimum temperature for double-stranded DNA breakage activity (which is defined by the polypeptide region for DNA breakage activity in the polypeptide), the promoter used and the growth conditions of the plant body and the like are taken into consideration for causing expression of the polypeptide. This is because genome shuffling efficiency is reduced when the double-stranded DNA breakage activity is too strong and there is too much damage to the plant body. Consequently, the expression intensity and expression timing of the polypeptide are preferably controlled based on the characteristics of the promoter, and the optimum temperature for the double-stranded DNA breakage activity of the polypeptide is preferably considered when setting the growth temperature of the transformed plant.

Conventional known methods may be applied as the methods for regenerating an individual plant body from various plant bodies such as transformed plant cells, tissue, organs and seeds.

Second Embodiment for Introducing Polypeptide of Invention

In the second embodiment, the polypeptide is introduced directly into a plant body by coating, spraying, dipping, injection, electroporation or the like. The method for introducing the polypeptide into the plant body is not particularly limited, and an appropriate embodiment may be adopted. To supply the polypeptide directly to a plant body, for example the polypeptide may be dissolved in water or an aqueous medium such as a buffer solution and supplied in that form to all or part of the plant body. The polypeptide can be efficiently introduced into the plant body in this way.

More specifically, a liquid containing the polypeptide may be brought into contact with the plant body by coating, dipping, mixing or the like, or injected directly into the plant tissue. The supply temperature and conditions are not particularly limited, but the temperature is preferably not the optimum temperature for the double-stranded DNA breakage activity of the polypeptide. For example, when the optimum temperature for double-stranded DNA breakage activity is about 37° C., the supply temperature is preferably not more than 30° C., or more preferably not more than 25° C. An embodiment in which the polypeptide is supplied directly is useful because it does not require causing expression of DNA or the like coding for the polypeptide, and the polypeptide can be applied to any site as needed.

When the polypeptide is introduced directly into a plant body, the plant body into which it is introduced is not particularly limited. For example, a protoplast, plant cells or callus may be used as the plant body.

Embodiments for Effecting Activity of Polypeptide of Invention in Plant Body

Next, embodiments for effecting the activity of the polypeptide in a plant body will be explained. The embodiments for effecting the intertissue migration activity and double-stranded DNA breakage activity of the polypeptide in a plant body are not particularly limited, and may be set appropriately so as to produce the intended intertissue migration activity and double-stranded DNA breakage activity and achieve an appropriate level of genome shuffling.

For example, in the shuffling method, a first embodiment may be an embodiment in which the intertissue migration activity and double-stranded DNA breakage activity of the polypeptide are made to act effectively. As a second embodiment, the double-stranded DNA breakage activity in particular may be made to act almost constantly and constitutively. As a third embodiment, the double-stranded DNA breakage activity may be made to act or increased deliberately and/or transiently.

First Embodiment for Effecting Activity of Polypeptide of Invention

To exploit the double-stranded DNA breakage activity and intertissue migration activity of the polypeptide most advantageously, in one embodiment the polypeptide is introduced into a tissue or organ other than a reproductive tissue or organ, and is then made to migrate based on its intertissue migration activity to a reproductive tissue or organ or precursor thereof, and a genome to be inherited by the next generation is then shuffled at that location based on the double-stranded DNA breakage activity of the polypeptide.

For example, when the plant body is bred and cultivated by sexual reproduction in such an embodiment, the polypeptide is directly introduced or introduced by transient expression into a tissue or organ not associated with sexual reproduction, such as a leaf, stem (excluding the stem tip, which is a reproductive precursor tissue) or root. A known transient expression system (for example, techniques available from GENEWARE, magnICON or *Medicago*) that is applicable to plants may be used for transient expression, or a known inducible expression system may be applied. In this embodiment, the polypeptide can be synthesized in a plant body without the need to select a recombinant plant. The polypeptide then migrates by intertissue migration activity to sexual reproductive tissue, and its double-stranded DNA breakage activity is made to act in that tissue to effect genome shuffling. If the polypeptide is only introduced into a site other than a reproductive site of the plant body, a seed or other (non-recombinant) breeding material for sexual reproduction can be obtained directly.

When the plant body is bred and cultivated by asexual reproduction for example, the polypeptide is directly introduced or transiently expressed in a tissue or organ that is not a breeding material for the target asexual reproduction. Even in this embodiment, the polypeptide is synthesized in a plant body without the need to select a recombinant plant, and various kinds of (non-recombinant) breeding material for asexual reproduction for example can be obtained directly as above with the polypeptide.

The first embodiment is suitable for obtaining a diverse next-generation population of a plant body by sexual reproduction, and is also broadly useful for obtaining a next-generation population by asexual reproduction.

Regarding mode of action of the double-stranded DNA breakage activity of the polypeptide in the first embodiment in particular, this activity may be made to act constitutively or transiently by appropriately applying the first embodiment and the second embodiment below.

Second Embodiment for Effecting Activity of Polypeptide of Invention

When the activity of the polypeptide, and particularly its double-stranded DNA breakage activity, is made to act almost constantly and constitutively, various embodiments are possible for example considering the possible damage to the plant body from the double-stranded DNA breakage activity. In all cases, the double-stranded DNA breakage activity is made to act in such a way that it is controlled at a fixed level of intensity or less.

(1) For example, a polypeptide obtained by applying a thermophilic restriction enzyme to a polypeptide region for double-stranded DNA breakage activity is introduced into a plant body either directly or using the expression vector or the like. The plant body is then grown at a suitable growth temperature for the plant. In general, the growth temperature of the plant is lower than the optimum temperature of the thermophilic restriction enzyme. The intertissue migration activity and double-stranded DNA breakage activity of the polypeptide are thus made to act almost constantly and constitutively after the polypeptide is introduced. The growth temperature is selected appropriately according to the type of plant body or in light of the double-stranded DNA breakage activity to be effected by the polypeptide, but considering the possible growth temperatures of the plant body it may be at least 4° C., or at least 18° C. and not more than 30° C. for example. Moreover, the lower limit may be 19° C. or more, or 20° C. or more for example, or 21° C. or more for example, and the upper limit may be 28° C. or less, or 25° C. or less for example, or 24° C. or less for example, or 23° C. or less for example.

(2) Alternatively, for example a polypeptide obtained by applying a cold restriction enzyme to a polypeptide region for double-stranded DNA breakage activity is introduced into a plant body either directly or using the expression vector or the like. The plant body is then growth at a growth temperature at or below the optimum temperature of the cold restriction enzyme. In this way, intertissue migration activity and double-stranded DNA breakage activity are made to act more or less continuously after the polypeptide is introduced.

The growth temperature is selected appropriately according to the type of plant body or in light of the double-stranded DNA breakage activity to be effected by the polypeptide, but considering the possible growth temperatures of the plant body, it may be at least 4° C., or for example at least 18° C. and not more than 30° C. Moreover, the lower limit may be 19° C. or more, or 20° C. or more for example, or 21° C. or more for example, and the upper limit may be 28° C. or less, or 25° C. or less for example, or 24° C. or less for example, or 23° C. or less for example.

Depending on the plant body to be used and the type of cold restriction enzyme or the like, a cold restriction enzyme may be useful even though in general the temperature difference between the optimum temperature of a thermophilic restriction enzyme and the suitable growth temperature of a plant body is not greater than the thermophilic restriction enzyme.

The promoter of the expression vector used in the first embodiment may be a constitutive promoter or an inducible promoter. The constitutive promoter may be a high expression vector such as the cauliflower mosaic virus 35S promoter, a promoter such as the SIG2 promoter with an expression intensity lower than that of the cauliflower mosaic virus 35S promoter, or a promoter such as the HSP18.2 promoter that produces a low level of expression at a temperature below the induction temperature.

Using a constitutive promoter, the polypeptide is synthesized continuously and the activity of the polypeptide tends to be continuous whether the promoter is a low expression promoter or high expression promoter. Using an inducible promoter, because the polypeptide is only synthesized under induction, the activity of the polypeptide can be produced continuously by either controlling the induction conditions so that a sufficient quantity is synthesized by transient induction, or by controlling the induction conditions so that the polypeptide is synthesized continuously. When the polypeptide is introduced directly, a sufficiently quantity of the polypeptide may be introduced at one time, or it may be introduced continuously.

The growth temperature used in this embodiment is intended to be a temperature in a constant-temperature artificial environment, not in a natural environment with season changes and daytime variation. The time of applying this embodiment to a plant body is not particularly limited, but may be for example the entire period of plant cultivation excluding periods of special temperature treatment such as vernalization treatment and the like.

Third Embodiment for Effecting Activity of Polypeptide of Invention

Several embodiments are possible for transiently effecting or enhancing the activity of the polypeptide and its double-stranded DNA breakage activity in particular.

(1) For example, the polypeptide is introduced into a plant body either directly or with the expression vector or the like. As in the first embodiment, the polypeptide is introduced in such a way that it is continuously present in the plant body. The plant is then deliberately grown for a specific period of time at any stage of plant growth at a temperature which is higher than the growth temperature and which is a high growth temperature closer to the optimum temperature of a restriction enzyme applied to the polypeptide for double-stranded DNA breakage activity in the polypeptide in order to effect or enhance the double-stranded DNA breakage activity. This serves to effect or enhance the intertissue migration activity and double-stranded DNA breakage activity of the polypeptide for a specific period of time.

For example, when the restriction enzyme is derived from a thermophile, a temperature (mild condition) lower than the optimum temperature of the thermophilic restriction enzyme is adopted as the growth temperature. This may be about at least 15° C. and not more than 25° C. lower than the optimum temperature for example. More preferably, activation is performed at a temperature near the lower limit at which the double-stranded DNA breakage activity of the polypeptide can be expressed. Given 100% as the activity at the optimum temperature for example, a temperature near the lower limit at which the double-stranded DNA breakage activity of the polypeptide can be expressed may be a temperature at which this activity is about at least 5% and not more than 30%, or preferably about at least 5% and not more than 20%.

For example, this growth temperature depends on the type of the polypeptide and plant body, but may be at least 18° C. and not more than 45° C. The lower limit is more preferably 20° C. or more, or still more preferably 22° C. or more, or yet more preferably 25° C. or more, or most preferably 30° C. or more, or especially 35° C. or more. The upper limit is preferably 45° C. or less, or more preferably 42° C. or less, or still more preferably 40° C. or less, or yet more preferably 37° C. or less, or most preferably 35° C. or less. At this action temperature, temperature damage to the plant body can be suppressed and efficient genome shuffling efficiency ensured.

The period during which this growth temperature is applied depends on the type of the polypeptide and the type and growth temperature of the plant body, but may be about 30 minutes to 1 hour, or a relatively long time of at least 2 hours for example, or at least 3 hours for example, or at least 4 hours for example, or at least 6 hours for example, or at least 12 hours for example, or at least 24 hours for example, or at least 36 hours for example, or at least 48 hours for example, or at least 60 hours for example, or at least 72 hours for example.

When the restriction enzyme is a cold restriction enzyme for example, the growth temperature may be within a temperature range including the normal temperature ranges in the various embodiments explained above relative to the optimum temperature of the cold restriction enzyme. The lower limit is 10° C. or more for example, or 15° C. or more for example, or 20° C. or more for example, or 25° C. or more for example. The upper limit is 47° C. or less for example, or 45° C. or less for example, or 42° C. or less for example. The range is at least 10° C. and not more than 47° C. for example, or at least 10° C. and not more than 45° C. for example, or at least 15° C. and not more than 45° C. for example, or at least 20° C. and not more than 42° C. for example, or at least 25° C. and not more than 42° C. for example.

The period during which this growth temperature is applied depends on the growth temperature conditions and the optimum temperature of the protein, but may be for example about several minutes to 1 hour. It may also be at least 10 minutes and not more than 50 minutes for example, or at least 15 minutes and not more than 45 minutes for example. It may also be at least 1 hour and not more than 10 hours for example, or at least 1 hour and not more than 6 hours for example, or at least 1 hour and not more than 4 hours for example, or at least 1 hour and not more than 3 hours for example.

(2) The polypeptide is also introduced transiently into a plant body for example either directly or with the expression vector or the like. That is, the polypeptide is either introduced directly so that it exists transiently in the plant body, or in such a way that it can be synthesized by transiently applying the induction conditions of an inducible promoter. The plant is grown for a specific period of time at a high growth temperature closer to the optimum temperature of a restriction enzyme applied to the polypeptide for double-stranded DNA breakage activity in the polypeptide, either at the same time as the transient introduction or during a specific period when the polypeptide is present in the plant body. The intertissue migration activity and double-stranded DNA breakage activity of the polypeptide can thus be produced or enhanced for the intended period of time. In this case, the growth temperature is restored to the original growth temperature after a specific period of time.

The embodiments explained above for causing the activity of the polypeptide are examples, and the invention is not limited thereby. The various conditions for causing the desired activity can be determined appropriately by a person skilled in the art after considering the type and amount of the restriction enzyme or the like having double-stranded DNA breakage activity that is applied to the polypeptide (or the expression intensity set by various control factors when using an expression vector), the type of plant, the growth condition of the plant, the genome shuffling effect and the like.

The genome shuffling effect can be determined by evaluation methods using reporter genes or by known chromosome evaluation techniques or the like. The growth condition of the plant body (growth delay or suppression, decreased survival rates) may also be used as a marker of the genome shuffling effect. This is because growth delay or suppression or decreased survival rates are observed when double-stranded DNA breakage activity has occurred and a genome shuffling effect is presumed.

The genome shuffling effect can also be evaluated based on an increase in the expressed amounts of genes such as the BRCA1 gene associated with DNA repair in plants, and on the level of homologous recombination using a GUS reporter gene.

With such genome shuffling methods, it is possible to reduce cell damage and efficiently grow one or two or more plant bodies (populations) having various mutations produced by genome shuffling, and to obtain a seed or other reproductive material. The reproductive material can then be cultivated or the like, and its phenotype and genotype can be analyzed to obtain a plant body having an advantageous mutation.

By using the polypeptide such as a florigen protein having intertissue migration activity, it is possible to obtain a plant body through genome shuffling without genetic recombination. The growth of the plant body can also be accelerated.

The genome shuffling method may also be implemented as a method of producing a plant body or population thereof having genome mutations, with or without genetic recombination. Moreover, the genome shuffling method may also be implemented as a method of producing a breeding material for sexual or asexual reproduction, with or without genetic recombination.

The present Description provides a plant body carrying the polypeptide or expressably carrying a polynucleotide coding for the polypeptide. The present Description also provides a plant body or population thereof having a genome mutation not produced by genetic recombination. Furthermore, the present Description provides a breeding material having a genome mutation not produced by genetic recombination.

EXAMPLES

Specific examples of the disclosures of the present Description are explained below. The examples below are for purposes of explaining the disclosures, and do not limit their scope.

Example 1

Preparation of Construct for Obtaining Plant Body Expressing Polypeptide Coding for Florigen Protein (FT) and Restriction Enzyme (TaqI)

To prepare the constructs pBI 35SΩ:FT-Taq and pBI HSP18.2:FT-TaqI, PCR amplification was performed using the primers XhoI-HSP18.2-F: 5'-actcgagtctggtggtttcaact-tggg-3' (SEQ ID NO:5) and HSP18.2-SalI-BamHI-R: 5'-aggatccgtcgactgttcgttgcttttcgggag-3' (SEQ ID NO:6) with the *Arabidopsis thaliana* (Col-0) genome as the template, and a DNA fragment containing the HSP18.2 promoter region was isolated. This DNA fragment was cloned to a pBI 101N2 vector (Sugimoto et al. (2014), J. Exp. Bot., 65, 5385-5400) to obtain pBI HSP18.2:GUS.

Next, PCR amplification was performed using the primers ApaI-NdeI-SalI-FT-F: 5'-agggccccatatggtcgacatgtc-tataaatataagagaccctc-3' (SEQ ID NO:7) and FT-KpnI-R: 5'-aggtaccaagtcttcttcctccgcage-3' (SEQ ID NO:8) with the *Arabidopsis thaliana* (Col-0) cDNA as the template, and a DNA fragment of a FT ORF was isolated. This DNA fragment was cloned to a pGEM (registered trademark)-T Easy vector (Promega) to obtain pGEM FT. PCR amplification was then performed with the primers KpnI-G-TaqI-F: 5'-aggtaccggaggtggaggtgcaatggcccctacacaagccca-3' (SEQ ID NO:9) and TaqI-SacI-R: 5'-agagctctgtacctcacgggccggt-gagggc-3' (SEQ ID NO: 10), and a TaqI genome DNA fragment was isolated. This DNA fragment was cloned to a pGEM (registered trademark)-T Easy vector to obtain pGEM TaqI.

Next, the pGEM FT was treated with ApaI and KpnI, and the resulting DNA fragment containing the FT ORF was cloned to pGEM TaqI that had been treated with ApaI and KpnI, to obtain pGEM FT-TaqI. Using pGEM FT-TaqI as the template, PCR amplification was performed with the primers SalI-FT-F: 5'-aattactatttacaattacagtcgacatgtctataaatataagagaccctc-3' (SEQ ID NO: 11) and KpnI-BsrGI-R: 5'-agccgggcggccgctttacttgtacatgtacctcacgggccggtgagggc-3' (SEQ ID NO: 12), and the resulting DNA fragment containing a FT-TaqI ORF was cloned to pBI 35SΩ:AtPP2CFI that had been treated with BsrGI and SalI (Sugimoto et al. (2014), Overexpression of a novel *Arabidopsis* PP2C isoform, AtPP2CF1, enhances plant biomass production by increasing inflorescence stem growth. J. Exp. Bot., 65, 5385-5400) using an In-Fusion (registered trademark) Dry-Down PCR Cloning Kit w/Cloning Enhancer (Clontech) (In-Fusion reaction) to obtain pBI 35SΩ:FT-TaqI. pGEM FT-TaqI was also treated with SacI and SalI, and the resulting DNA fragment containing the FT-TaqI ORF was cloned to pBI HSP18.2:GUS that had been treated with SacI and SalI, to obtain pBI HSP18.2:FT-TaqI.

Example 2

Preparation of *Arabidopsis Thaliana* Transformants

The vectors described above were transformed by the Floral-dip method (Clough, S. J. et al., Plant J., 16 (1998), 735-743) into a wild strain (Col-0) or 1406 strain (Endo, M. et al., EMBO J., 25, 5579-5590) of *Arabidopsis thaliana*. The 1406 strain is a strain obtained from the Col-0 strain by introducing a modified GUS reporter gene in which part of the β-glucuronidase (GUS) gene consists of gene fragments divided in two so as to overlap each other and arranged in direct orientation. The modified GUS reporter gene is not itself able to produce functional GUS, but when homologous recombination occurs within the modified GUS reporter gene it is converted into the normal GUS gene, and becomes capable of producing functional GUS. Selection of $T_1$ plants was performed in MS medium containing kanamycin (final concentration 30 μg/mL) and carbenicillin (final concentration 100 μg/mL). This was then potted with Super Mix A (Sakata Seed).

Example 3

Observation of 1406 Strain/pBI 35SΩ:FT-TaqI Phenotype

Seeds of the control strain (1406 strain) and 35SΩ:FT-TaqI were vernalized for 3 days. They were then sown in Super Mix A (Sakata Seed), and grown under long-day conditions (16 hours light/8 hours dark, about 50 μmol m$^{-2}$ s$^{-1}$ white fluorescent light) in an artificial climate chamber (22° C., humidity about 60%). The time required for the first flower stem to reach 10 mm and the number of leaves at that time were measured, with the results shown in FIGS. 3A to 3C.

A fused protein was prepared comprising a florigen protein linked to a restriction enzyme, using an *Arabidopsis thaliana* florigen protein (FT, At1g65480) as the florigen protein and TaqI as the restriction enzyme. The fused protein was called FT-TaqI.

The FT protein (Wigge, P. A. (2011), FT, A Mobile Developmental Signal in Plants. Curr. Biol., 21, R374-R378) is synthesized in leaf tissue, moves through the sieve tissue to the meristems, and induces flower bud formation (induces flowering).

Figure 3B:
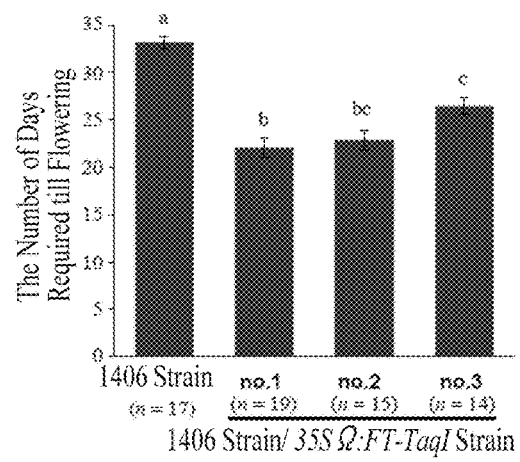
Figure 3C:
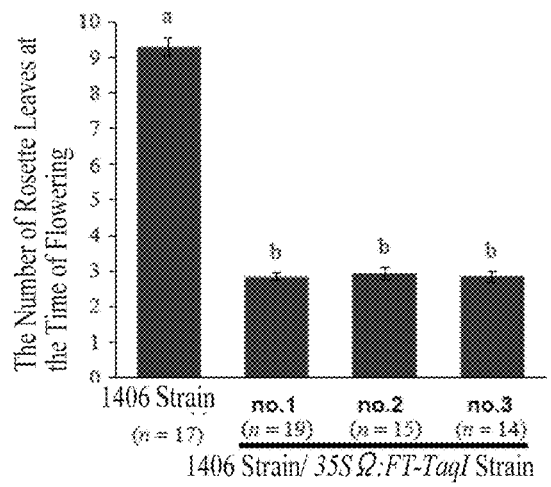
Figure 4A:
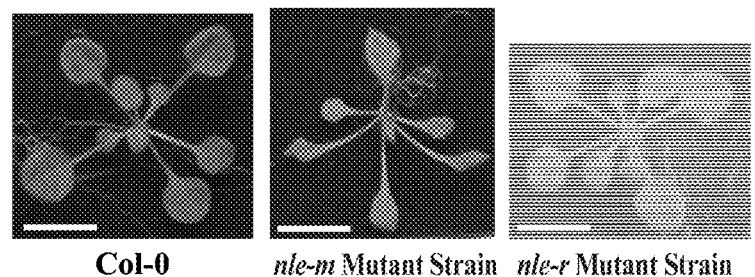
FIGS. 4A to 4D show the phenotypes of an nle mutant strain.
Figure 4B:
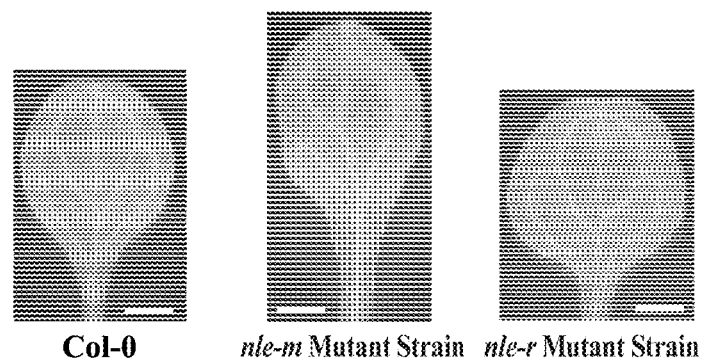
Figure 4C:
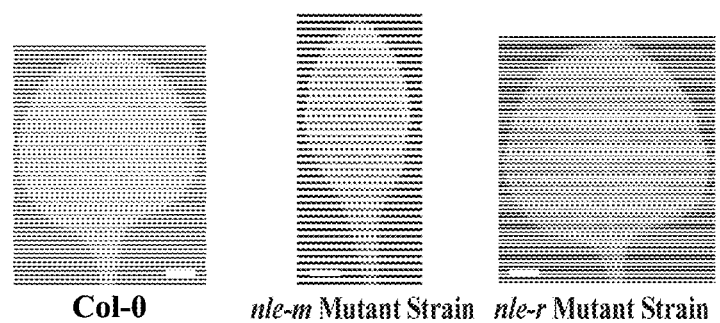
Figure 4D:
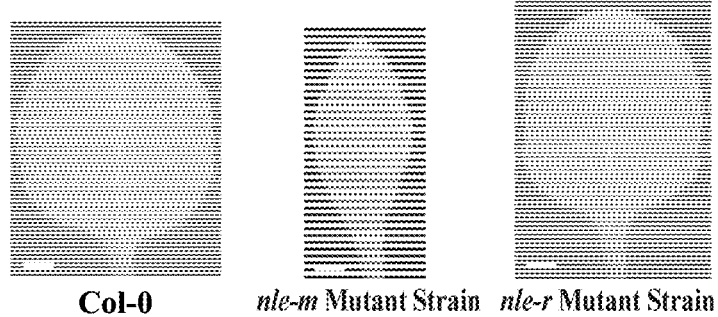

FIG. 3A is a photograph showing the control strain (1406 strain) and 1406 strain/35SΩ:FT-TaqI strain 24 days after sowing. The 1406 strain has not bolted, while the 1406 strain/35SΩ:FT-TaqI strain has bolted and has elongated flower stems. Flowering was defined as the point at which the first flower stem reached 10 mm, and the time taken to this point and the number of rosette leaves were measured. In comparison with the control strain (1406 strain), the 1406 strain/35SΩ:FT-TaqI strain took 7 to 10 days fewer to flower, and the number of rosette leaves was about 6 fewer (FIGS. 3B and 3C). This shows that the 1406 strain/35SΩ:FT-TaqI strain is an early bloomer in terms of both growth time and developmental stage. It can be seen from this that FT-TaqI functions in the same way as a florigen protein, and can induce flowering.

Example 4

Isolation of Nle Mutant Strain from Col-0/pBI HSP18.2:FT-TaqI

The Col-0 into with the introduced pBI HSP18.2:FT-TaqI prepared in Example 2 was sown on MS medium (containing 1% sucrose) (Gellan gum, final concentration 0.5%), and vernalized for 3 days. This was then transferred to an artificial climate chamber (22° C., humidity about 60%) and grown under long-day conditions (16 hours light/8 hours dark, about 50 μmol m$^{-2}$ s$^{-1}$ white fluorescent light). After 20 to 26 days of growth (including the vernalization period), the plant body was potted with Super Mix A, and cultivated until seeds formed. A narrow leaf (nle) mutant strain was isolated from the $T_2$ plants. Photographs of this mutant strain are shown in FIG. 3A.

FIGS. 4A to 4D are photographs of a plant body of the mutant strain 21 days after sowing. As shown in FIGS. 4A to 4D, in comparison with the wild strain (Col-0) the nle mutant strain developed long, thin rosette leaves. This shows that a plant body with a different phenotype can be created in the next generation by causing FT-TaqI to be expressed in a plant body.

Moreover, a strain exhibiting the same phenotype as the nle mutant strain and a strain reverting to the same phenotype as the wild strain were both isolated from a population of $F_1$ plants obtained by self-crossing the nle mutant strain and a population of $F_1$ plants obtained by crossing the wild strain with the nle mutant strain (FIGS. 4A to 4D). The strain exhibiting the same phenotype as the nle mutant strain was called narrow leaf-mutant (nle-m), while the strain reverting to the phenotype of the wild strain was called narrow leaf-revertant (nle-r). The genetic characteristics of this nle mutant strain indicate that it retained the causal mutation of the nle mutant strain in a hetero form.

Example 5

Specifying Causal Mutation of Nle Mutant Strain

A gene map was prepared for purposes of specifying the causal mutation of the nle mutant strain. $F_1$ seeds were obtained from a plant body obtained by crossing the nle mutant strain (background Col-0) with a wild strain (Ler). A population of $F_2$ plants obtained by self-crosslinking $F_1$ plants exhibiting the nle mutant phenotype was used as a mapping population. When the karyotype was determined at an arbitrary position on each chromosome using a $F_2$ strain exhibiting the nle-r phenotype (wild strain phenotype), the nle mutant could not be mapped on any chromosome.

However, when the karyotype was determined using an $F_2$ strain exhibiting the nle-m phenotype with the DNA markers shown in Table 2 below, the Ler homo karyotype was not detected with the markers Chr.3_10.4 Mb, Chr.3_23.0 Mb and Chr.5_1.0 Mb on the third chromosome out of the DNA markers used in analysis. This result indicates that these genome regions may have been duplicated in the nle-m mutant strain.

TABLE 2

DNA markers of nle-m mutant causal region

| | Variety of DNA marker* | | Chr. | SEQ ID NO: | Primer sequence | Restriction enzyme | Fragment size (bp) to be compared |
|---|---|---|---|---|---|---|---|
| Chr.3_10.3Mb | C | | Chr.3 10,361,447-10,361,964 | 92 | 5'-ccatgatccgaa gagactat-3' | TaqI | Col-0: 270 Ler: 324 |
| | | | | 93 | 5'-atgttgagtact gcctttag-3' | | |
| Chr.3_23.0Mb | S | | Chr.3 23,031,050-23,031,192 | 94 | 5'-atggagaagctt acactgatc-3' | — | Col-0: 143 Ler: 123 |
| | | | | 95 | 5'-tggatttcttcc tctcttcac-3' | | |
| Chr.5_1.0Mb | C | | Chr.5 979,897-980,465 | 96 | 5'-acttactcggtg cgtttctgttg-3' | RsaI | Col-0: 568 Ler: 378 |
| | | | | 97 | 5'-atacatccccct cgactccaatta-3' | | |

*C: CAPS (Cleaved Amplified Polymorphic Sequences) marker; S: SSLP (Simple Sequence Length Polymorphism) marker Tiling array analysis (chromosome copy number analysis) was performed to investigate this possibility. An *Arabidopsis thaliana* tiling array was designed using an Agilent eArray system. An At_tiling_400K_v3.2 was designed comprising 381,815 60-mer probes arranged with an average spatial resolution of about 314 nt on the *Arabidopsis thaliana* genome. Similarly, an At_tiling_180K_v4 was designed comprising 177,170 60-mer probes arranged with an average spatial resolution of about 677 nt on the *Arabidopsis thaliana* genome. The tiling arrays were designed in accordance with the Agilent protocols. The tiling arrays were scanned with an Agilent G2565CA Microarray Scanner (Agilent). The fluorescent signal was extracted and quantified using Feature Extraction software. The relative level was determined by the formula (Relative level=$\text{Log}_{10}$ ($\text{Cy5}_{sample}/\text{Cy3}_{control}$)), and the average value of the relative levels of 20 continuous probes on the chromosome was determined. The tiling array analysis results for the nle mutant strain are shown in FIGS. 5A to 5C.

As shown in FIGS. 5A to 5C, while the nle-r mutant strain had the same number of chromosome copies as the wild type for all chromosomes, the nle-m strain was confirmed to have a partial copy number increase (duplication) of chromosomes in the lower arm of chromosome 3 and the upper arm of chromosome 5. This result matched the result of the gene map for the nle mutant. Consequently, it appears that genome reorganization (in this case duplication) induced by FT-TaqI in the nle-m mutant strain is associated with the phenotype of narrow leaves.

Sequence Table Free Text

SEQ ID NOS:5 to 12: Primers

Sequence List

The invention claimed is:

1. A polypeptide comprising:
a first polypeptide region having restriction enzyme activity, and
a second polypeptide region having intertissue migration activity,
wherein the second polypeptide region has either at least 95% sequence identity with the amino acid sequence of SEQ ID NO:1 or 100% sequence identity with the amino acid sequence of SEQ ID NO:3.

2. A genome shuffling agent containing the polypeptide according to claim 1.

3. A polynucleotide coding for the polypeptide according to claim 1.

4. A genome shuffling agent containing the polynucleotide according to claim 3.

5. An expression vector comprising the polynucleotide according to claim 3.

6. A plant body having the polypeptide according to claim 1 or a polynucleotide coding for the polypeptide.

7. A method for genome shuffling in plants, comprising a step of introducing the polypeptide according to claim 1 into a plant body, and causing the intertissue migration activity and the double-stranded DNA breakage activity to act within the plant body.

8. The polypeptide according to claim 1, wherein the first polypeptide region is a restriction enzyme having a 4-base or 5-base recognition site and an optimum temperature of 50° C. or higher.

9. The polypeptide according to claim 1, wherein the first polypeptide region is a restriction enzyme having a 4-base recognition site and an optimum temperature of 50° C. or higher.

10. The polypeptide according to claim 1, wherein the first polypeptide region is a restriction enzyme having a 4-base or 5-base recognition site and an optimum temperature of 65° C. or higher.

11. The polypeptide according to claim 1, wherein the first polypeptide region is a restriction enzyme having a 4-base recognition site and an optimum temperature of 65° C. or higher.

12. A polypeptide comprising:
a first polypeptide region having restriction enzyme activity, and
a second polypeptide region having intertissue migration activity, wherein the second polypeptide region has either at least 85% sequence identity with the amino acid sequence of SEQ ID NO:1 or at least 95% sequence identity with the amino acid sequence of SEQ ID NO:3, and comprising the following motifs:
(i) a third motif which has the 38 amino acid residues from position 51 to position 88 of SEQ ID NO: 1 or position 53 to position 90 of SEQ ID NO:3, with the following permitted variations for each respective amino acid residue, in order:
K/Q/H, P, R, V/I, E/D/V, I/V, G, G, E/D/N/T/P, D/E, L/M, R, N/T/S/I, F, Y/F, T, L, V, M, V/A, D/V, P, D, V/A, P, S, P, S, N/D/E/S, P, H/N/S/R/T, L, R/K/T, E, Y, L, H, W;
(ii) a fourth motif, which has the 60 amino acid residues from position 89 to position 148 of SEQ ID NO:1 or position 91 to position 150 of SEQ ID NO:3,
with the following permitted variations for each respective amino acid residue, in order:
L, V, T, D, I, P, A/G, T/S, T, G/A/E, T/A/S/N/T, T/N/S/ A/P, F, G, N/Q/H/S, E, I/V, V/M/I, C/S, Y/H, E/G, N/S, P, S/R/L/G, P, T/S/Y/N/I, A/S/V/M/I/L, G, I, H, R, V/F/L/I, V/I/C/L, F/L/M, I/V/A, L, F/L, R/Q/H, Q, L, G/R, R, Q, T, V, Y/F, A/E/T/P, P, G, W, R, Q/P, N/Q/H, F, N/S, T, R/K, E/D/G/N, F, A/T; and
(iii) a fifth motif, which has the 26 amino acid residues from position 149 to position 174 of SEQ ID NO: 1 or position 151 to position 176 of SEQ ID NO:3, with the following permitted variations for each respective amino acid residue, in order:
E/S/A, I/L/V, Y, N, L/I, G, L/S/P/Q/H, P/A, V/I, A/S, A/S/T, V/L/A, F/Y, Y/F/C, N/D, C, Q, R, E/D, S/A/T/ G/N/R, G, C/S/T, G, G, R, R.

* * * * *